US011717419B2

(12) United States Patent
Altarac et al.

(10) Patent No.: US 11,717,419 B2
(45) Date of Patent: Aug. 8, 2023

(54) EXPANDABLE INTERBODY SPACER

(71) Applicant: NeuroStructures, Inc., Irvine, CA (US)

(72) Inventors: Moti Altarac, Irvine, CA (US); Joey Reglos, Irvine, CA (US)

(73) Assignee: Neurostructures, Inc., Irvine, CA (US)

(*) Notice: Subject to any disclaimer, the term of this patent is extended or adjusted under 35 U.S.C. 154(b) by 232 days.

(21) Appl. No.: 17/117,965

(22) Filed: Dec. 10, 2020

(65) Prior Publication Data
US 2022/0183854 A1 Jun. 16, 2022

(51) Int. Cl.
*A61F 2/44* (2006.01)
*A61F 2/46* (2006.01)
*A61F 2/30* (2006.01)

(52) U.S. Cl.
CPC .......... *A61F 2/447* (2013.01); *A61F 2/30749* (2013.01); *A61F 2/4611* (2013.01); *A61F 2/30728* (2013.01); *A61F 2002/30301* (2013.01); *A61F 2002/30405* (2013.01); *A61F 2002/30507* (2013.01); *A61F 2002/30523* (2013.01); *A61F 2002/30565* (2013.01); *A61F 2002/30617* (2013.01); *A61F 2002/4615* (2013.01)

(58) Field of Classification Search
CPC .......... A61F 2/4455–447; A61F 2/4611; A61F 2/30749; A61F 2/30728; A61F 2002/30301; A61F 2002/30405; A61F 2002/30507; A61F 2002/30523; A61F 2002/30565; A61F 2002/30617; A61F 2002/4615
USPC ........................ 623/17.11–17.16; 606/99–100
See application file for complete search history.

(56) References Cited

U.S. PATENT DOCUMENTS

| | | |
|---|---|---|
| 3,554,075 A | 1/1971 | Johnson |
| 3,741,205 A | 6/1973 | Markolf et al. |
| 5,085,660 A | 2/1992 | Lin |
| 5,364,399 A | 11/1994 | Lowery et al. |
| 5,423,826 A | 6/1995 | Coates et al. |
| 5,549,612 A | 8/1996 | Yapp et al. |
| 5,616,142 A | 4/1997 | Yuan et al. |
| 5,616,144 A | 4/1997 | Yapp et al. |

(Continued)

FOREIGN PATENT DOCUMENTS

| | | |
|---|---|---|
| EP | 1520545 B1 | 11/2006 |
| EP | 1429675 B1 | 10/2007 |

(Continued)

*Primary Examiner* — Jessica Weiss
(74) *Attorney, Agent, or Firm* — Lukas IP; Rimas T. Lukas

(57) ABSTRACT

An expandable interbody spacer for the spine is provided. The spacer includes upper and lower endplates simultaneously movable with respect to a housing along an axis transverse to a longitudinal axis to increase or decrease the height of the spacer selectably along both an anterior side and a posterior side for uniform expansion/contraction of the endplates or only along the anterior side for angular expansion/contraction of the endplates. A spacer deployment instrument is provided that is selectable to effect uniform or angular expansion/contraction. When uniform expansion/contraction is selected a gear on an anterior rod is engaged with a gear on a posterior rod to simultaneously rotate both rods in opposite directions. Opposite threads on actuators of the spacer effect translation of the actuators in the same direction along the longitudinal axis.

19 Claims, 36 Drawing Sheets

(56) References Cited

U.S. PATENT DOCUMENTS

| | | |
|---|---|---|
| 5,676,483 A | 10/1997 | Koubek |
| 5,725,588 A | 3/1998 | Errico et al. |
| 6,045,552 A | 4/2000 | Zucherman et al. |
| 6,070,294 A | 6/2000 | Perkins et al. |
| 6,139,550 A | 10/2000 | Michelson |
| 6,258,089 B1 | 7/2001 | Campbell et al. |
| 6,261,291 B1 | 7/2001 | Talaber et al. |
| 6,398,783 B1 | 6/2002 | Michelson |
| 6,527,776 B1 | 3/2003 | Michelson |
| 6,599,290 B2 | 7/2003 | Bailey et al. |
| 6,602,255 B1 | 8/2003 | Campbell et al. |
| 6,605,090 B1 | 8/2003 | Trieu et al. |
| 6,626,907 B2 | 9/2003 | Campbell et al. |
| 6,629,998 B1 | 10/2003 | Lin |
| 6,652,525 B1 | 11/2003 | Assaker et al. |
| 6,695,846 B2 | 2/2004 | Richelsoph et al. |
| 6,723,126 B1 * | 4/2004 | Berry ................ A61F 2/4611 606/247 |
| 6,743,256 B2 | 6/2004 | Mason |
| 6,755,833 B1 | 6/2004 | Paul et al. |
| 6,793,658 B2 | 9/2004 | LeHuec et al. |
| 6,849,093 B2 | 2/2005 | Michelson |
| 6,926,718 B1 | 8/2005 | Michelson |
| 6,936,051 B2 | 8/2005 | Michelson |
| 6,964,664 B2 | 11/2005 | Freid et al. |
| 7,008,426 B2 | 3/2006 | Paul |
| 7,070,599 B2 | 7/2006 | Paul |
| 7,175,623 B2 | 2/2007 | Thramann et al. |
| 7,186,254 B2 | 3/2007 | Dinh et al. |
| 7,204,837 B2 | 4/2007 | Paul |
| 7,220,263 B2 | 5/2007 | Cordaro |
| 7,255,699 B2 | 8/2007 | Paul |
| 7,273,481 B2 | 9/2007 | Lombardo et al. |
| 7,276,070 B2 | 10/2007 | Muckter |
| 7,278,997 B1 | 10/2007 | Mueller et al. |
| 7,288,094 B2 | 10/2007 | Lindemann et al. |
| 7,288,095 B2 | 10/2007 | Baynham et al. |
| 7,291,152 B2 | 11/2007 | Abdou |
| 7,306,605 B2 | 12/2007 | Ross |
| 7,318,825 B2 | 1/2008 | Butler et al. |
| 7,322,984 B2 | 1/2008 | Doubler et al. |
| 7,438,715 B2 | 10/2008 | Doubler et al. |
| 7,452,370 B2 | 11/2008 | Anderson |
| 7,468,069 B2 | 12/2008 | Baynham et al. |
| 7,524,325 B2 | 4/2009 | Khalili |
| 7,601,170 B2 | 10/2009 | Winslow et al. |
| 7,651,517 B2 | 1/2010 | Konieczynski et al. |
| 7,662,154 B2 | 2/2010 | Ribeiro |
| 7,662,174 B2 | 2/2010 | Doubler et al. |
| 7,686,806 B2 | 3/2010 | Rhyne |
| 7,704,255 B2 | 4/2010 | Michelson |
| 7,740,630 B2 | 6/2010 | Michelson |
| 7,740,649 B2 | 6/2010 | Mosca et al. |
| 7,803,157 B2 | 9/2010 | Michelson |
| 7,811,285 B2 | 10/2010 | Michelson |
| 7,815,666 B2 | 10/2010 | Baynham et al. |
| 7,824,432 B2 | 11/2010 | Michelson |
| 7,857,839 B2 | 12/2010 | Duong et al. |
| 7,887,547 B2 | 2/2011 | Campbell et al. |
| 7,909,859 B2 | 3/2011 | Mosca et al. |
| 7,963,981 B2 | 6/2011 | Binder et al. |
| 7,985,242 B2 | 7/2011 | Forton et al. |
| 8,048,075 B2 | 11/2011 | Michelson |
| 8,057,522 B2 | 11/2011 | Rothman et al. |
| RE43,008 E | 12/2011 | Talaber et al. |
| 8,128,668 B2 | 3/2012 | Paul |
| 8,206,293 B2 | 6/2012 | Reglos et al. |
| 8,221,476 B2 | 7/2012 | Paul |
| 8,236,033 B2 | 8/2012 | Paul |
| 8,236,034 B2 | 8/2012 | Binder et al. |
| 8,394,145 B2 | 3/2013 | Weiman |
| 8,398,713 B2 | 3/2013 | Weiman |
| 8,419,777 B2 | 4/2013 | Walker et al. |
| 8,439,924 B1 | 5/2013 | McBride et al. |
| 8,460,308 B2 | 6/2013 | Marino et al. |
| 8,480,747 B2 | 7/2013 | Melkent et al. |
| 8,562,655 B2 | 10/2013 | Butler |
| 8,562,656 B2 | 10/2013 | Humphreys |
| 8,591,556 B2 | 11/2013 | Hansell et al. |
| 8,652,182 B1 | 2/2014 | Walker et al. |
| 8,668,723 B2 | 3/2014 | Altarac et al. |
| 8,845,731 B2 | 9/2014 | Weiman |
| 8,845,734 B2 | 9/2014 | Weiman |
| 8,852,279 B2 | 10/2014 | Weiman |
| 8,888,854 B2 | 11/2014 | Glerum et al. |
| 9,125,757 B2 | 9/2015 | Weiman |
| 9,204,972 B2 | 12/2015 | Weiman et al. |
| 9,204,974 B2 | 12/2015 | Glerum et al. |
| 9,233,007 B2 | 1/2016 | Sungarian et al. |
| 9,326,861 B2 | 5/2016 | Iott et al. |
| 9,381,093 B1 | 7/2016 | Morris et al. |
| 9,402,739 B2 | 8/2016 | Weiman et al. |
| 9,480,579 B2 | 11/2016 | Davenport et al. |
| 9,554,918 B2 | 1/2017 | Weiman |
| 9,561,116 B2 | 2/2017 | Weiman et al. |
| 9,743,958 B2 | 8/2017 | Ishii et al. |
| 9,770,343 B2 | 9/2017 | Weiman |
| 9,782,265 B2 | 10/2017 | Weiman et al. |
| 9,788,970 B2 | 10/2017 | Reimels |
| 9,801,734 B1 | 10/2017 | Stein et al. |
| 9,833,336 B2 | 12/2017 | Davenport et al. |
| 9,855,151 B2 | 1/2018 | Weiman |
| 9,867,715 B2 | 1/2018 | McLaughlin et al. |
| 9,907,673 B2 | 3/2018 | Weiman et al. |
| 9,913,726 B2 | 3/2018 | Weiman |
| 9,925,062 B2 | 3/2018 | Glerum et al. |
| 9,962,271 B2 | 5/2018 | Glerum |
| 9,968,462 B2 | 5/2018 | Weiman |
| 10,004,607 B2 | 6/2018 | Weiman et al. |
| 10,010,430 B2 | 7/2018 | Glerum et al. |
| 10,016,224 B2 | 7/2018 | Altarac et al. |
| 10,016,282 B2 | 7/2018 | Seifert et al. |
| 10,022,241 B2 | 7/2018 | Faulhaber et al. |
| 10,028,842 B2 | 7/2018 | Gray et al. |
| 10,052,213 B2 | 8/2018 | Glerum et al. |
| 10,052,215 B2 | 8/2018 | Hessler et al. |
| 10,080,669 B2 | 9/2018 | Davenport et al. |
| 10,085,849 B2 | 10/2018 | Weiman et al. |
| 10,117,754 B2 | 11/2018 | Davenport et al. |
| 10,137,001 B2 | 11/2018 | Weiman |
| 10,137,009 B2 | 11/2018 | Weiman et al. |
| 10,143,569 B2 | 12/2018 | Weiman et al. |
| 10,154,912 B2 | 12/2018 | Glerum |
| 10,219,913 B2 | 3/2019 | Matthews et al. |
| 10,219,914 B2 | 3/2019 | Faulhaber |
| 10,226,358 B2 | 3/2019 | Glerum |
| 10,226,359 B2 | 3/2019 | Glerum et al. |
| 10,265,190 B2 | 4/2019 | Faulhaber |
| 10,278,830 B1 | 5/2019 | Walker et al. |
| 10,299,934 B2 | 5/2019 | Seifert et al. |
| 10,314,719 B2 | 6/2019 | Hessler et al. |
| 10,327,917 B2 | 6/2019 | Glerum et al. |
| 10,350,081 B2 | 7/2019 | Seifert et al. |
| 10,350,085 B2 | 7/2019 | Glerum et al. |
| 10,369,000 B2 | 8/2019 | McLaughlin et al. |
| 10,369,002 B2 | 8/2019 | Rhoda et al. |
| 10,369,004 B2 | 8/2019 | Faulhaber |
| 10,376,377 B2 | 8/2019 | Seifert et al. |
| 10,390,962 B2 | 8/2019 | Weiman |
| 10,470,894 B2 | 11/2019 | Foley et al. |
| 10,492,928 B2 | 12/2019 | Himmelberger et al. |
| 10,500,057 B2 | 12/2019 | McLaughlin et al. |
| 10,524,924 B2 | 1/2020 | Davenport et al. |
| 10,548,743 B2 | 2/2020 | Faulhaber |
| 10,617,533 B2 | 4/2020 | Glerum et al. |
| 10,624,761 B2 | 4/2020 | Davenport et al. |
| 10,639,166 B2 | 5/2020 | Weiman et al. |
| 2002/0120270 A1 | 8/2002 | Tried et al. |
| 2003/0060828 A1 | 3/2003 | Michelson |
| 2003/0093082 A1 | 5/2003 | Campbell et al. |
| 2003/0105462 A1 | 6/2003 | Haider |
| 2003/0105466 A1 | 6/2003 | Ralph et al. |
| 2003/0105467 A1 | 6/2003 | Ralph et al. |
| 2003/0125739 A1 | 7/2003 | Bagga et al. |

(56) References Cited

U.S. PATENT DOCUMENTS

| | | |
|---|---|---|
| 2003/0135216 A1 | 7/2003 | Sevrain |
| 2003/0153920 A1 | 8/2003 | Ralph et al. |
| 2003/0171753 A1 | 9/2003 | Collins et al. |
| 2003/0181912 A1 | 9/2003 | Michelson |
| 2003/0187440 A1 | 10/2003 | Richelsoph et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0229348 A1 | 12/2003 | Sevrain |
| 2003/0236528 A1 | 12/2003 | Thramann |
| 2004/0006343 A1 | 1/2004 | Sevrain |
| 2004/0015169 A1 | 1/2004 | Gause |
| 2004/0019353 A1 | 1/2004 | Freid et al. |
| 2004/0024081 A1 | 2/2004 | Trieu et al. |
| 2004/0030336 A1 | 2/2004 | Khanna |
| 2004/0034352 A1 | 2/2004 | Needham et al. |
| 2004/0039387 A1 | 2/2004 | Gause et al. |
| 2004/0049279 A1 | 3/2004 | Sevrain |
| 2004/0068319 A1 | 4/2004 | Cordaro |
| 2004/0087945 A1 | 5/2004 | Ralph et al. |
| 2004/0087951 A1 | 5/2004 | Khalili |
| 2004/0092929 A1 | 5/2004 | Zindrick |
| 2004/0092947 A1 | 5/2004 | Foley |
| 2004/0097925 A1 | 5/2004 | Boehm, Jr. et al. |
| 2004/0097934 A1 | 5/2004 | Farris et al. |
| 2004/0097935 A1 | 5/2004 | Richelsoph et al. |
| 2004/0097938 A1 | 5/2004 | Alleyne |
| 2004/0097950 A1 | 5/2004 | Foley et al. |
| 2004/0106924 A1 | 6/2004 | Ralph et al. |
| 2004/0122426 A1 | 6/2004 | Michelson |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0133205 A1 | 7/2004 | Thramann et al. |
| 2004/0153088 A1 | 8/2004 | Ralph et al. |
| 2004/0158246 A1 | 8/2004 | Assaker et al. |
| 2004/0177847 A1 | 9/2004 | Foley et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204710 A1 | 10/2004 | Patel et al. |
| 2004/0204712 A1 | 10/2004 | Kolb et al. |
| 2004/0204713 A1 | 10/2004 | Abdou |
| 2004/0210314 A1 | 10/2004 | Michelson |
| 2004/0215192 A1 | 10/2004 | Justis et al. |
| 2004/0215195 A1 | 10/2004 | Shipp et al. |
| 2004/0220571 A1 | 11/2004 | Assaker et al. |
| 2004/0220572 A1 | 11/2004 | Michelson |
| 2004/0225290 A1 | 11/2004 | Ferree |
| 2004/0236333 A1 | 11/2004 | Lin |
| 2004/0236334 A1 | 11/2004 | Michelson |
| 2004/0236335 A1 | 11/2004 | Michelson |
| 2004/0243128 A1 | 12/2004 | Howland |
| 2004/0260306 A1 | 12/2004 | Fallin et al. |
| 2005/0015092 A1 | 1/2005 | Rathbun et al. |
| 2005/0015093 A1 | 1/2005 | Suh et al. |
| 2005/0027296 A1 | 2/2005 | Thramann et al. |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0038436 A1 | 2/2005 | Michelson |
| 2005/0043732 A1 | 2/2005 | Dalton |
| 2005/0059970 A1 | 3/2005 | Kolb |
| 2005/0059971 A1 | 3/2005 | Michelson |
| 2005/0075633 A1 | 4/2005 | Ross |
| 2005/0085816 A1 | 4/2005 | Michelson |
| 2005/0137597 A1 | 6/2005 | Butler et al. |
| 2005/0149021 A1 | 7/2005 | Tozzi |
| 2005/0149026 A1 | 7/2005 | Butler et al. |
| 2005/0149027 A1 | 7/2005 | Campbell et al. |
| 2005/0171551 A1 | 8/2005 | Sukovich et al. |
| 2005/0177160 A1 | 8/2005 | Baynham et al. |
| 2005/0177161 A1 | 8/2005 | Baynham et al. |
| 2005/0177163 A1 | 8/2005 | Abdou |
| 2005/0187551 A1 | 8/2005 | Orbay et al. |
| 2005/0187552 A1 | 8/2005 | Michelson |
| 2005/0187553 A1 | 8/2005 | Grabowski et al. |
| 2005/0187554 A1 | 8/2005 | Michelson |
| 2005/0192576 A1 | 9/2005 | Michelson |
| 2005/0208095 A1 | 9/2005 | Hunter et al. |
| 2005/0209593 A1 | 9/2005 | Kolb |
| 2005/0216005 A1 | 9/2005 | Howland |
| 2005/0216009 A1 | 9/2005 | Michelson |
| 2005/0216010 A1 | 9/2005 | Michelson |
| 2005/0228386 A1 | 10/2005 | Ziolo et al. |
| 2005/0234455 A1 | 10/2005 | Binder et al. |
| 2005/0261690 A1 | 11/2005 | Binder et al. |
| 2005/0273105 A1 | 12/2005 | Konieczynski et al. |
| 2005/0277930 A1 | 12/2005 | Parsons |
| 2005/0277938 A1 | 12/2005 | Parsons |
| 2005/0283152 A1 | 12/2005 | Lindemann et al. |
| 2006/0009845 A1 | 1/2006 | Chin |
| 2006/0030852 A1 | 2/2006 | Sevrain |
| 2006/0079961 A1 | 4/2006 | Michelson |
| 2006/0082015 A1 | 4/2006 | Happonen et al. |
| 2006/0085001 A1 | 4/2006 | Michelson |
| 2006/0149251 A1 | 7/2006 | Ziolo et al. |
| 2006/0149256 A1 | 7/2006 | Wagner et al. |
| 2006/0155298 A1 | 7/2006 | Mueller et al. |
| 2006/0161157 A1 | 7/2006 | Mosca et al. |
| 2006/0167456 A1 | 7/2006 | Johnston et al. |
| 2006/0189997 A1 | 8/2006 | Guenther et al. |
| 2006/0200134 A1 | 9/2006 | Freid et al. |
| 2006/0200146 A1 | 9/2006 | Doubler et al. |
| 2006/0200147 A1 | 9/2006 | Ensign et al. |
| 2006/0229620 A1 | 10/2006 | Rothman et al. |
| 2006/0235405 A1 | 10/2006 | Hawkes |
| 2006/0241611 A1 | 10/2006 | Castro |
| 2006/0241616 A1 | 10/2006 | Konieczynski et al. |
| 2006/0276792 A1 | 12/2006 | Ensign et al. |
| 2006/0287653 A1 | 12/2006 | Rhyne |
| 2007/0083203 A1 | 4/2007 | Ribeiro |
| 2007/0123884 A1 | 5/2007 | Abdou |
| 2007/0167954 A1 | 7/2007 | Sicvol et al. |
| 2007/0185489 A1 | 8/2007 | Abdou |
| 2007/0203492 A1 | 8/2007 | Needham et al. |
| 2007/0213728 A1 | 9/2007 | Lindemann et al. |
| 2007/0213729 A1 | 9/2007 | Lindemann et al. |
| 2007/0213820 A1 | 9/2007 | Magerl et al. |
| 2007/0213828 A1 | 9/2007 | Trieu et al. |
| 2007/0225707 A1 | 9/2007 | Wisnewski et al. |
| 2007/0225717 A1 | 9/2007 | Hawkes |
| 2007/0225718 A1 | 9/2007 | Ensign |
| 2007/0233070 A1 | 10/2007 | Young |
| 2007/0233072 A1 | 10/2007 | Dickinson et al. |
| 2007/0233107 A1 | 10/2007 | Zielinski |
| 2007/0233108 A1 | 10/2007 | Stalcup et al. |
| 2007/0233110 A1 | 10/2007 | Muhanna et al. |
| 2007/0233117 A1 | 10/2007 | Butler et al. |
| 2007/0233118 A1 | 10/2007 | McLain |
| 2007/0233119 A1 | 10/2007 | Markworth |
| 2007/0233120 A1 | 10/2007 | Thramann et al. |
| 2007/0239158 A1 | 10/2007 | Trieu et al. |
| 2007/0270851 A1 | 11/2007 | Erickson et al. |
| 2007/0270965 A1 | 11/2007 | Ferguson |
| 2007/0276371 A1 | 11/2007 | Baynham et al. |
| 2007/0276405 A1 | 11/2007 | Huebner et al. |
| 2008/0021470 A1 | 1/2008 | Ross |
| 2008/0051794 A1 | 2/2008 | Dec et al. |
| 2008/0065082 A1* | 3/2008 | Chang ............... A61B 17/1659 606/85 |
| 2008/0208260 A1 | 8/2008 | Truckai et al. |
| 2008/0208262 A1 | 8/2008 | Butler et al. |
| 2008/0208263 A1 | 8/2008 | Butler et al. |
| 2008/0208341 A1 | 8/2008 | McCormack et al. |
| 2008/0215097 A1 | 9/2008 | Ensign et al. |
| 2008/0228226 A1 | 9/2008 | Shamie |
| 2008/0228230 A1 | 9/2008 | Ferree |
| 2008/0234680 A1 | 9/2008 | Zaiser et al. |
| 2008/0234681 A1 | 9/2008 | Baynham |
| 2008/0234689 A1 | 9/2008 | Melkent et al. |
| 2008/0234748 A1 | 9/2008 | Wallenstein et al. |

(56) References Cited

U.S. PATENT DOCUMENTS

| | | |
|---|---|---|
| 2008/0234749 A1 | 9/2008 | Forstein |
| 2008/0234750 A1 | 9/2008 | Woods et al. |
| 2008/0234751 A1 | 9/2008 | McClintock |
| 2008/0234752 A1 | 9/2008 | Dahners |
| 2008/0234753 A1 | 9/2008 | Trieu |
| 2008/0234755 A1 | 9/2008 | Henderson et al. |
| 2008/0269806 A1 | 10/2008 | Zhang et al. |
| 2008/0287999 A1 | 11/2008 | Markworth |
| 2008/0288001 A1 | 11/2008 | Cawley et al. |
| 2009/0105831 A1 | 4/2009 | Jones et al. |
| 2009/0131988 A1 | 5/2009 | Bush, Jr. et al. |
| 2009/0149888 A1 | 6/2009 | Abdelgany |
| 2009/0171397 A1 | 7/2009 | Rothman et al. |
| 2009/0177237 A1 | 7/2009 | Zucherman et al. |
| 2009/0177239 A1 | 7/2009 | Castro |
| 2009/0182341 A1 | 7/2009 | Link et al. |
| 2009/0182383 A1 | 7/2009 | Prybyla et al. |
| 2009/0187218 A1 | 7/2009 | Schaffhausen |
| 2009/0192549 A1 | 7/2009 | Sanders et al. |
| 2009/0210008 A1 | 8/2009 | Butler et al. |
| 2009/0222049 A1 | 9/2009 | Frigg et al. |
| 2009/0259226 A1 | 10/2009 | Michelson |
| 2009/0270926 A1 | 10/2009 | Hawkes |
| 2010/0016901 A1 | 1/2010 | Robinson |
| 2010/0042159 A1 | 2/2010 | Butler |
| 2010/0049256 A1 | 2/2010 | Jeon et al. |
| 2010/0057206 A1 | 3/2010 | Duffield et al. |
| 2010/0069968 A1 | 3/2010 | Assaker et al. |
| 2010/0145459 A1 | 6/2010 | McDonough et al. |
| 2010/0234897 A1 | 9/2010 | Fisher et al. |
| 2010/0312279 A1 | 12/2010 | Gephart et al. |
| 2010/0312346 A1 | 12/2010 | Kueenzi et al. |
| 2011/0054528 A1 | 3/2011 | Michelson |
| 2011/0106159 A1 | 5/2011 | Nazeck |
| 2011/0118784 A1 | 5/2011 | Baynham et al. |
| 2011/0190770 A1 | 8/2011 | Suh |
| 2011/0213421 A1 | 9/2011 | Binder et al. |
| 2011/0230885 A1 | 9/2011 | Weiner et al. |
| 2011/0270311 A1 | 11/2011 | Assaker et al. |
| 2011/0313477 A1 | 12/2011 | McLean et al. |
| 2012/0059475 A1* | 3/2012 | Weiman .................. A61F 2/447 623/17.16 |
| 2012/0065734 A1 | 3/2012 | Barrett et al. |
| 2012/0109208 A1 | 5/2012 | Justis et al. |
| 2012/0179259 A1 | 7/2012 | McDonough et al. |
| 2012/0245690 A1 | 9/2012 | Cowan, Jr. et al. |
| 2012/0277870 A1 | 11/2012 | Wolters et al. |
| 2013/0023936 A1 | 1/2013 | Altarac et al. |
| 2013/0046345 A1 | 2/2013 | Jones et al. |
| 2013/0053895 A1 | 2/2013 | Stoll et al. |
| 2013/0060294 A1 | 3/2013 | Donahue |
| 2013/0184767 A1 | 7/2013 | Kaufman et al. |
| 2013/0197588 A1 | 8/2013 | Abdou |
| 2013/0204306 A1 | 8/2013 | Walker et al. |
| 2013/0245705 A1 | 9/2013 | McBride et al. |
| 2013/0261679 A1 | 10/2013 | McBride et al. |
| 2013/0331892 A1 | 12/2013 | Peterson et al. |
| 2013/0345814 A1 | 12/2013 | Walkenhorst et al. |
| 2014/0142632 A1 | 5/2014 | Keyer et al. |
| 2014/0148860 A1 | 5/2014 | Rinner |
| 2014/0277145 A1 | 9/2014 | Reitblat et al. |
| 2014/0277206 A1 | 9/2014 | Reitblat et al. |
| 2014/0288653 A1 | 9/2014 | Chen |
| 2014/0343678 A1 | 11/2014 | Suddaby et al. |
| 2015/0039035 A1 | 2/2015 | Kruger |
| 2015/0094772 A1 | 4/2015 | Black et al. |
| 2016/0022317 A1 | 1/2016 | Kraus |
| 2016/0128746 A1 | 5/2016 | Dunaway |
| 2017/0367842 A1 | 12/2017 | Predick et al. |
| 2017/0367844 A1 | 12/2017 | Eisen et al. |
| 2018/0000606 A1* | 1/2018 | Hessler ................ A61F 2/30771 |
| 2018/0318099 A1 | 11/2018 | Altarac et al. |
| 2019/0000644 A1 | 1/2019 | Moore et al. |
| 2019/0133779 A1 | 5/2019 | McLaughlin et al. |
| 2019/0269521 A1 | 9/2019 | Shoshtaev |
| 2019/0298524 A1 | 10/2019 | Lauf et al. |
| 2020/0383797 A1 | 12/2020 | Predick et al. |
| 2021/0121299 A1 | 4/2021 | Hyder |

FOREIGN PATENT DOCUMENTS

| | | |
|---|---|---|
| EP | 1841376 A2 | 10/2007 |
| EP | 1847229 A2 | 10/2007 |
| FR | 2948553 A1 | 2/2011 |
| KR | 20080105505 A | 12/2008 |
| WO | 2006076422 A2 | 7/2006 |
| WO | 2006138291 A2 | 12/2006 |
| WO | 2007037774 A1 | 4/2007 |
| WO | 2007056516 A2 | 5/2007 |
| WO | 2007101266 A1 | 9/2007 |
| WO | 2007103081 A2 | 9/2007 |
| WO | 2007121080 A2 | 10/2007 |
| WO | 2006138291 B1 | 11/2007 |
| WO | 2007134199 A2 | 11/2007 |
| WO | 2009089395 A2 | 7/2009 |
| WO | 2009091770 A1 | 7/2009 |
| WO | 2009091775 A2 | 7/2009 |
| WO | WO-2019022976 A1 * | 1/2019 ........... A61F 2/4455 |

* cited by examiner

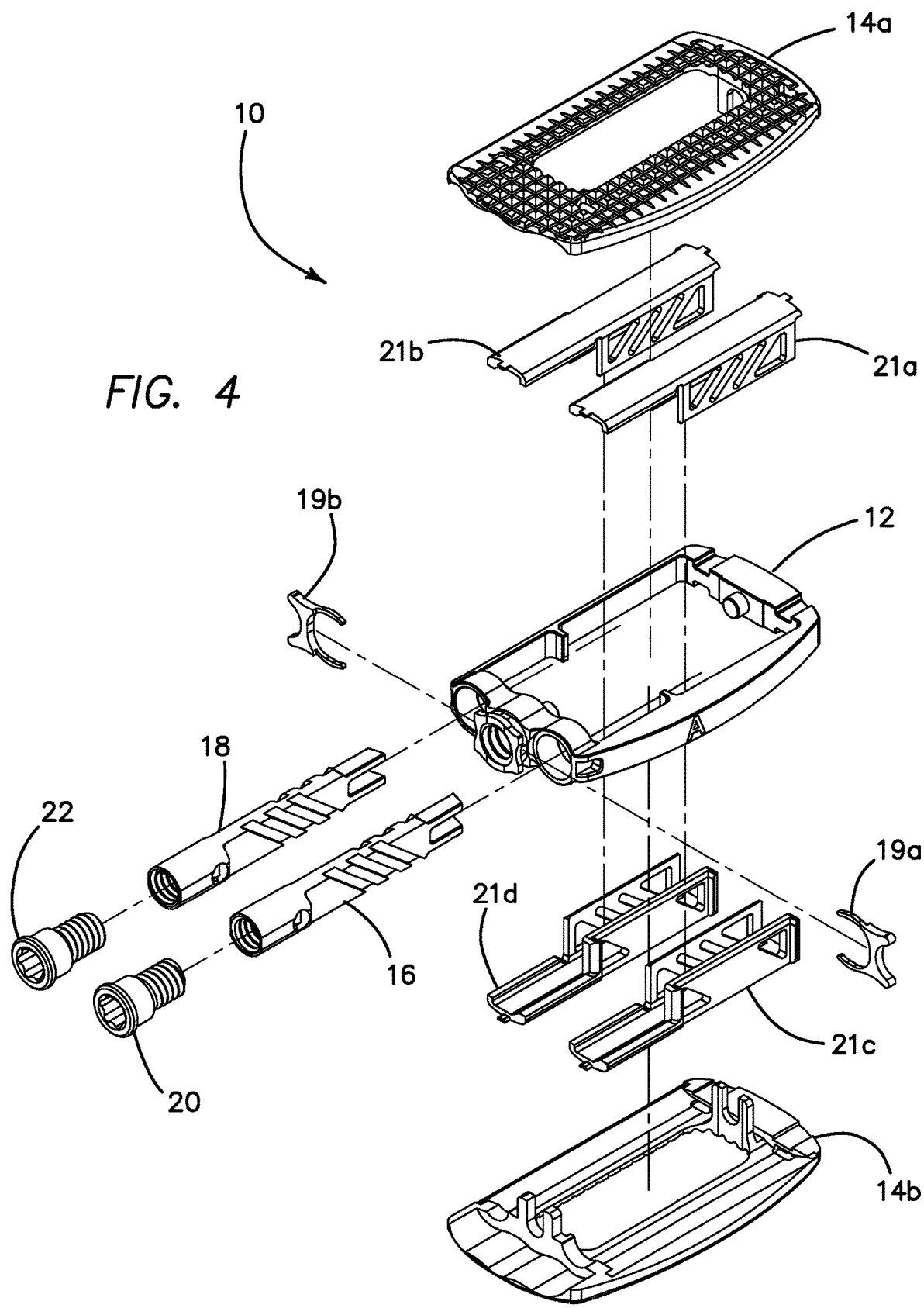

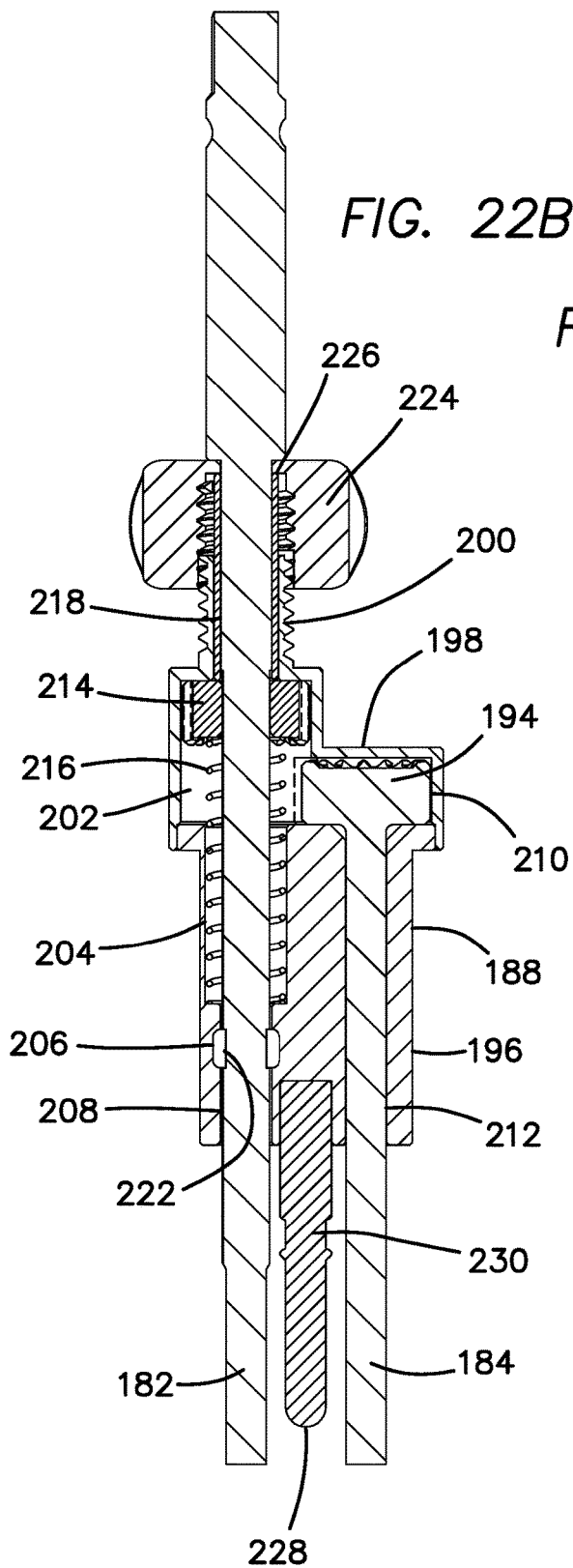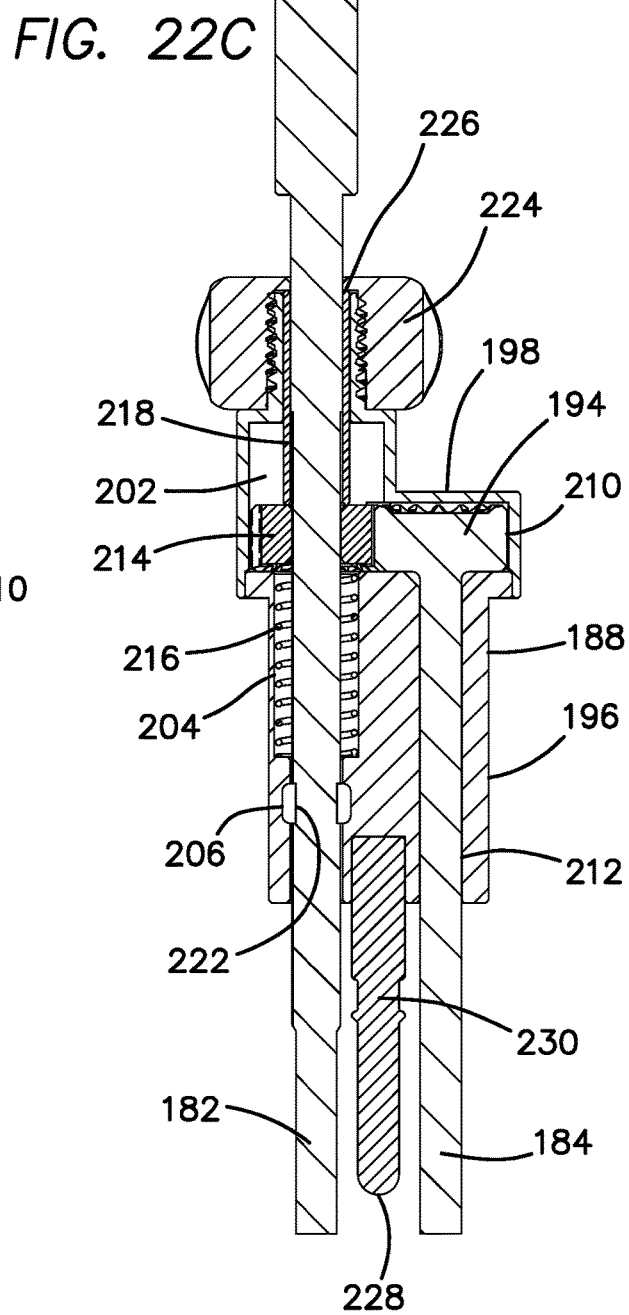

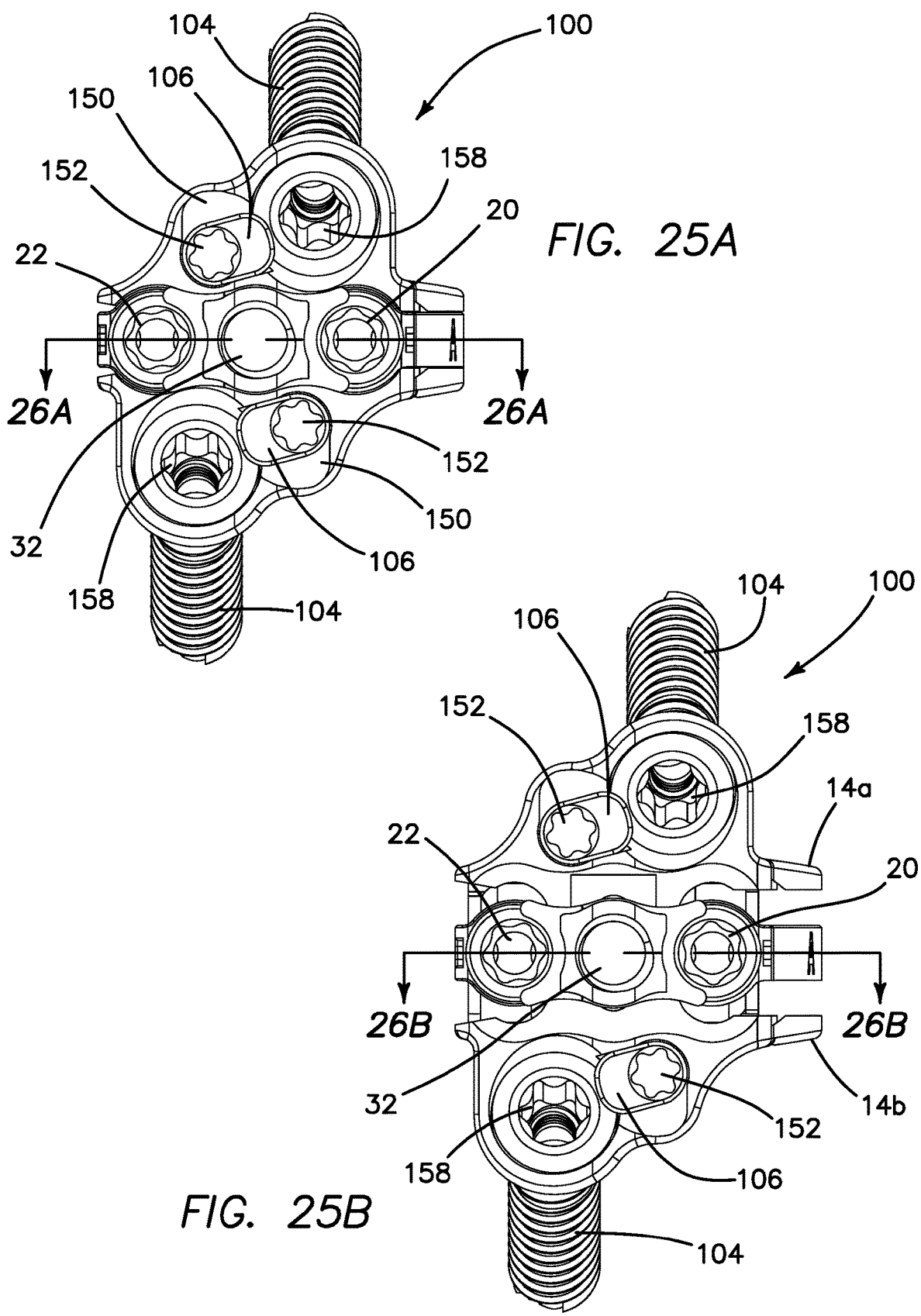

EXPANDABLE INTERBODY SPACER

FIELD OF THE INVENTION

This application relates generally to spinal implants, and in particular, expandable intervertebral spacers and instruments.

BACKGROUND OF THE INVENTION

Back pain can be caused by a variety of factors including but not limited to the rupture or degeneration of one or more intervertebral discs due to degenerative disc disease, spondylolisthesis, deformative disorders, trauma, tumors and the like. In such cases, pain typically results from compression or irritation of spinal nerve roots arising from reduced spacing between adjacent vertebrae, a damaged disc and or misalignment of the spine resulting from the injury or degeneration.

Common forms of treating such pain include various types of surgical procedures in which a damaged disc may be partially or totally excised. After the disc space is prepared, one or more implants are inserted between the adjacent vertebrae in an effort to restore the natural spacing and alignment between the vertebrae, so as to relieve the compression, irritation or pressure on the spinal nerve or nerves and, thereby, eliminate or significantly reduce the pain that the patient is experiencing. Typically, one or more implants are used together with substances that encourage bone ingrowth to facilitate fusion between adjacent vertebrae and achieve immobilization of adjacent bones. Surgeons insert these intervertebral devices to adjunctively facilitate bone fusion in between and into the contiguous involved vertebrae. This fusion creates a new solid bone mass and provides weight bearing support between adjacent vertebral bodies which acts to hold the spinal segment at an appropriate biomechanically restored height as well as to stop motion in a segment of the spine and alleviate pain.

In a posterior lumbar interbody fusion (PLIF) surgery, spinal fusion is achieved in the lower back by inserting an implant such as a cage and typically graft material to encourage bone ingrowth directly into the disc space between adjacent vertebrae. The surgical approach for PLIF is from the back of the patient, posterior to the spinal column. An anterior lumbar interbody fusion (ALIF) surgical procedure is similar to the PLIF procedure except that in the ALIF procedure, the disc space is fused by approaching the spine through the abdomen from an anterior approach instead of from a posterior approach. Another fusion procedure is called a transforaminal lumbar interbody fusion (TLIF) which involves a posterior and lateral approach to the disc space. To gain access to the disc space, the facet joint may be removed whereby access is gained via the nerve foramen. In an extreme lateral interbody fusion (XLIF), the disc space is accessed from small incisions on the patient's side.

In the typical procedures described above, the adjacent vertebrae must be distracted apart by a substantial amount in order to allow the surgeon to advance the implant with relatively little resistance along the delivery path. Also, the surgeon must typically release the implant at least once as the implant is being delivered along the delivery path and align and position the implant at the target position of implantation, typically in the anterior aspect of the disc space. If static spacers having a fixed height are employed, the right-sized spacer is selected from a plurality of spacers. Sometimes the selected static spacer must be interchanged for one of a different height during the procedure. Expandable spacers provide several advantages over static spacers. For example, expandable spacers may be more easily inserted in their low-profile configuration and then mechanically expanded into their high-profile configuration when in the right position. Another advantage of some expandable spacers is that the degree of expansion easily can be adjusted in-situ according to the specific anatomy of the patient. Generally, expandable spacers avoid the need to stock multiple sizes, and to remove and replace spacers during the procedure.

There is a need to provide an expandable spacer that is capable of customized expansion given a wide variability in patient anatomy at each vertebral level that meets the surgeon's demands for providing the best stabilization solutions. Sometimes uniform parallel expansion of the spacer is required. Sometimes only distal/anterior or proximal/posterior angulation of the spacer is required and sometimes a combination of distal or proximal angulation together with parallel expansion is required. Therefore, there is a need to provide a new and improved expandable interbody spacer that is versatile in both angulation and parallel expansion, easy to position, deploy from a low-profile to a high-profile configuration, angulate as well as expand uniformly. This invention, as described in the detailed description, sets forth an improved interbody spacer that meets these needs.

SUMMARY OF THE INVENTION

According to one aspect of the invention, an expandable interbody spacer for the spine is provided. The expandable interbody spacer includes a housing, an upper endplate having an upper contact surface, and a lower endplate having a lower contact surface. The spacer includes an upper anterior expander connected to the upper endplate. The upper anterior expander has at least one lower ramp. The spacer includes a lower anterior expander connected to the lower endplate. The lower anterior expander has at least one upper ramp. The spacer includes an upper posterior expander connected to the upper endplate. The upper posterior expander has at least one lower ramp. The spacer includes a lower posterior expander connected to the lower endplate. The lower posterior expander has at least one upper ramp. The spacer includes an anterior actuator including at least one upper ramp portion for engaging the at least one lower ramp of the upper anterior expander and at least one lower ramp portion for engaging the at least one upper ramp of the lower anterior expander. The anterior actuator has a threaded bore. The spacer includes a posterior actuator including at least one upper ramp portion for engaging the at least one lower ramp of the upper posterior expander and at least one lower ramp portion for engaging the at least one upper ramp of the lower posterior expander. The posterior actuator has a threaded bore. The spacer includes an anterior drive screw threadably engaged with the threaded bore of the anterior actuator. The anterior drive screw is laterally and longitudinally fixed and rotatable with respect to the housing. Rotation of the anterior drive screw causes the anterior actuator to move along the longitudinal axis causing the at least one lower ramp of the upper anterior expander to slide against the at least one upper ramp portion of the anterior actuator to cause the upper anterior expander and connected upper endplate to move along an axis transverse to the longitudinal axis. Also, with longitudinal translation of the anterior actuator, the at least one upper ramp of the lower anterior expander slides against the at least one lower ramp portion of the anterior actuator to cause the lower anterior expander and connected lower endplate to move along an axis transverse to the longitudinal axis. The spacer includes a posterior drive screw threadably engaged with the threaded bore of the posterior actuator. The posterior drive screw is laterally and longitudinally fixed and rotatable with respect to the housing. Rotation of the posterior drive screw causes the posterior actuator to move along the longitudinal axis and the at least one lower ramp of the upper posterior expander to slide against the at least one upper ramp portion of the posterior actuator to cause the upper posterior expander and connected upper endplate to move along an axis transverse to the longitudinal axis and the at least one upper ramp of the lower posterior expander to slide against the at least one lower ramp portion of the posterior actuator to cause the lower anterior expander and connected lower endplate to move along an axis transverse to the longitudinal axis.

According to another aspect of the invention, an instrument for an expandable interbody spacer is provided. The instrument includes a housing having an anterior gear chamber interconnected to a posterior gear chamber. The instrument includes an anterior rod extending from a proximal end to a distal end and rotatably connected to the housing. The anterior rod has a spacer-engaging tip at the distal end and a handle at the proximal end. The instrument includes a posterior rod extending from a proximal end to a distal end and spaced apart from the anterior rod. The posterior rod is rotatably connected to the housing. The posterior rod has a spacer-engaging tip at the distal end aligned with the spacer-engaging tip of the anterior rod. The instrument includes a posterior gear fixed to the proximal end of the posterior rod and located inside the posterior gear chamber. The instrument includes an anterior gear connected concentrically to the anterior rod. The anterior gear is located inside the anterior gear chamber and movable longitudinally with respect to the anterior rod. The instrument includes an actuator configured to move the anterior gear along the anterior rod between a disengaged position in which the anterior gear is disengaged from the posterior gear and an engaged position in which the anterior gear is engaged with the posterior gear. Rotation of the handle causes rotation of both the anterior rod and the posterior rod when in the engaged position.

According to another aspect of the invention, an expandable spacer and instrument system is provided. The spacer includes an upper endplate and a lower endplate on either side of a housing. The spacer includes an anterior drive screw longitudinally fixed to the housing and threadingly connected to an anterior actuator located along the anterior side. Rotation of the anterior drive screw moves the anterior actuator along the longitudinal axis which moves the upper endplate and lower endplate along an axis transverse to the longitudinal axis to increase or decrease a height of the spacer along the anterior side. The spacer includes a posterior drive screw longitudinally fixed to the housing and threadingly connected to a posterior actuator along the posterior side such that rotation of the posterior drive screw moves the posterior actuator along the longitudinal axis which moves the upper endplate and lower endplate along the axis transverse to the longitudinal axis to increase or decrease a height of the spacer along the posterior side. The instrument includes an anterior rod connected to an instrument housing. The anterior rod has a handle at a proximal end and a tip at a distal end for engaging the anterior drive screw of the spacer. Rotation of the anterior rod in a first direction rotates the anterior drive screw in the first direction. The instrument includes an anterior gear connected to and rotatable with the anterior rod. The instrument includes a posterior rod connected to the instrument housing. A posterior gear is connected to the posterior rod. The anterior gear is movable with respect to the anterior rod to engage or disengage the posterior gear. When the anterior gear is engaged with the posterior gear, rotation of the anterior rod in a first direction rotates the anterior gear in the first direction and the posterior gear and posterior rod in a second direction opposite to the first direction to increase the distance between the endplates along both the anterior and posterior sides. When the anterior gear is not engaged with the posterior gear, rotation of the anterior rod in a first direction rotates the anterior gear in the first direction to increase the distance between the endplates along only the anterior side to angulate the endplates.

According to another aspect of the invention, a method for an interbody spacer for the spine is provided. The method includes the step of providing a spacer having an anterior actuator along an anterior side of the spacer and a posterior actuator along the posterior side. The spacer includes upper and lower endplates connected to the anterior and posterior actuators via anterior and posterior, upper and lower expanders such that the expanders ramp against respective ramp portions on the actuators. The method includes the step of providing an instrument having a driver with an anterior rod and a posterior rod extending from and rotatable with respect to a housing. An anterior gear is provided concentrically around the anterior rod such that the anterior gear is movable longitudinally with respect to the anterior rod and the anterior gear is rotatable together with the anterior rod. A posterior gear is provided concentrically fixed around the posterior rod. The method includes the step of connecting the anterior rod to the anterior actuator and the posterior rod to the posterior actuator. The method includes the step of moving the anterior gear into engagement with the posterior gear. The method includes the step of rotating the anterior rod, when the anterior gear is engaged with the posterior gear, in a first direction causing the posterior rod to rotate in a second direction opposite to the first direction causing the anterior and posterior actuators to translate in a longitudinal direction and the endplates to move in a direction transverse to the longitudinal direction to increase the distance between the upper and lower endplates uniformly across the midline into expansion. The method includes the step of rotating the anterior rod in the second direction causing the posterior rod to rotate in the first direction causing the anterior and posterior actuators to translate in a longitudinal direction and the endplates to move in a direction transverse to the longitudinal direction to decrease the distance between the upper and lower endplates uniformly across the midline. The method includes the step of moving the anterior gear out of engagement with the posterior gear and rotating the anterior rod in the first direction to cause the anterior actuator to translate in a longitudinal direction causing the upper and lower endplates to move in a direction transverse to the longitudinal direction to increase the distance between the upper and lower endplates uniformly across the midline only along the anterior side of the spacer. The method includes the step of rotating the anterior rod in the second direction when the anterior gear is disengaged to translate the anterior actuator in a longitudinal direction causing the upper and lower endplates to move in a direction transverse to the longitudinal direction to decrease the distance between the upper and lower endplates uniformly across the midline only along the anterior side of the spacer.

BRIEF DESCRIPTION OF THE DRAWINGS

FIG. 4 is an exploded view of the expandable interbody spacer of FIG. 1.

FIG. 22B is a partial cross-sectional view of a driver in a configuration for anterior actuation/angulation according to the present invention.

FIG. 22C is a partial cross-sectional view of a driver in a configuration for anterior and posterior actuation/parallel expansion according to the present invention.

FIG. 25A is a proximal end elevational view of a stand-alone expandable spacer in a low-profile, unexpanded configuration according to the present invention.

FIG. 25B is a proximal end elevational view of a stand-alone expandable interbody spacer in parallel expansion according to the present invention.

DETAILED DESCRIPTION OF THE INVENTION

Figure 1:
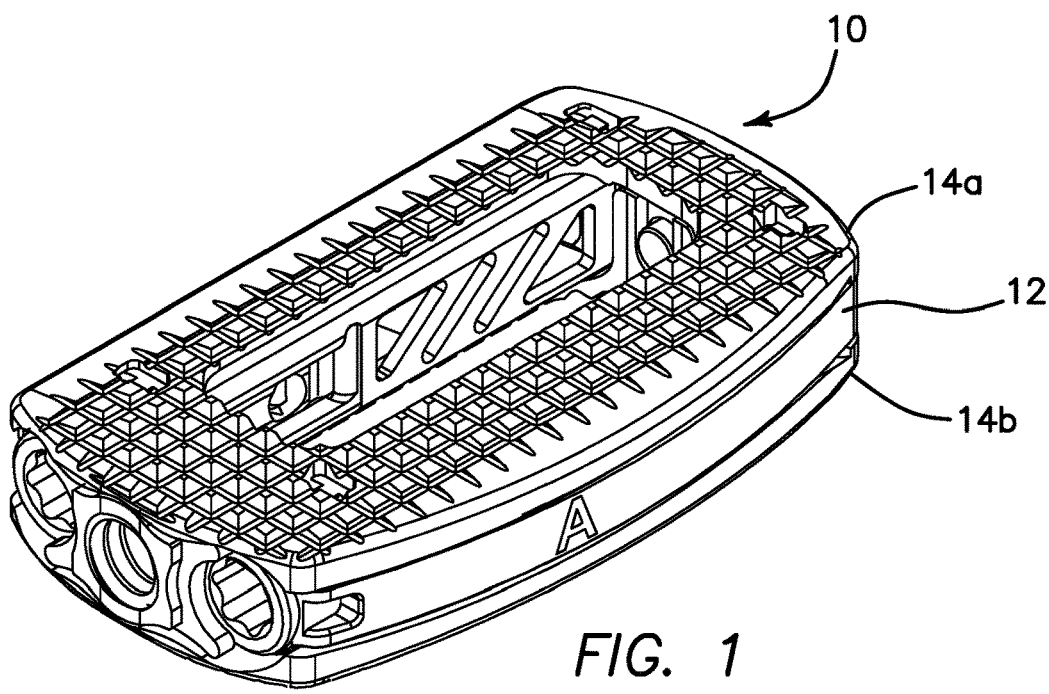
FIG. 1 is a front top perspective view of an expandable interbody spacer in its low-profile configuration according to the present invention.
Figure 2:
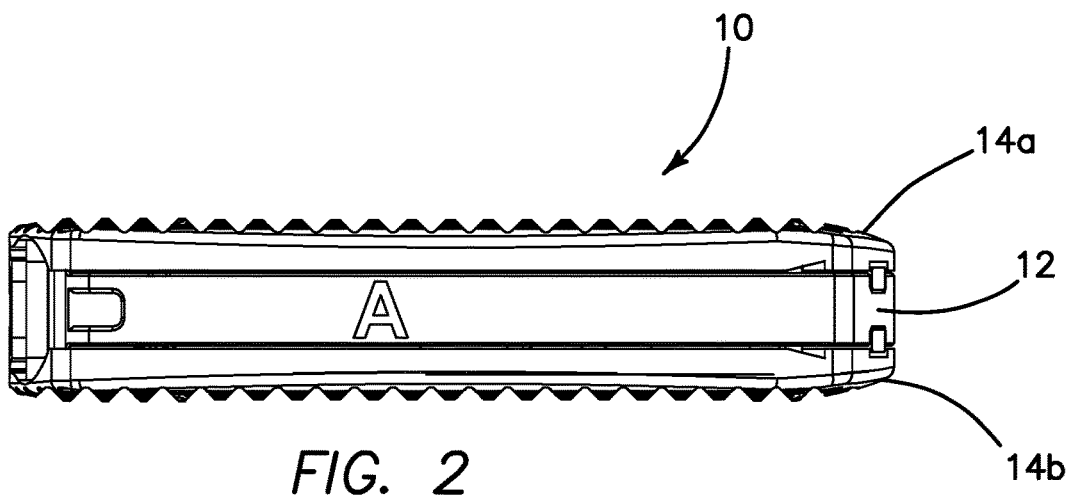
FIG. 2 is an anterior side elevational view of the expandable interbody spacer of FIG. 1.
Figure 3:
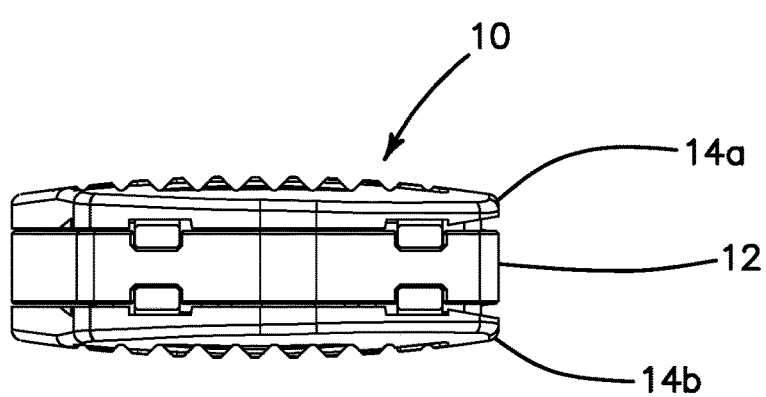
FIG. 3 is a distal end elevational view of the expandable interbody spacer of FIG. 1.

An expandable interbody spacer that is movable from an unexpanded configuration into a variety of expanded configurations including uniform parallel expansion and anterior-only angulation is described below. FIGS. 1-3 depict an expandable interbody spacer 10 in an unexpanded configuration. The spacer 10 is typically used to stabilize or fuse vertebral bodies in the lumbar or other region of the spine. With particular reference to the exploded view of FIG. 4, the expandable interbody spacer 10 includes a housing 12, upper and lower endplates 14a, 14b, an anterior actuator 16, a posterior actuator 18, an anterior drive screw 20, and a posterior drive screw 22, two upper expanders 21a, 21b and two lower expanders 21c, 21d, an anterior actuator retainer 19a and a posterior actuator retainer 19b. The expandable interbody spacer 10 is insertable into the disc space between two adjacent vertebral bodies while in an unexpanded state illustrated in FIGS. 1-3. Generally, the unexpanded state is characterized by a low-profile configuration in which the height of the spacer 10 is the lowest and the endplates 14a, 14b are parallel and not angled to each other. Once inserted and properly positioned inside the disc space, both upper and lower endplates 14 are expanded in height on both upper and lower sides of the housing 12 into an expanded state. The spacer 10 has a number of possible expanded states. The expanded states include uniform expansion and anterior-only angular expansion. In the expanded state characterized by uniform expansion, the endplates 14a, 14b are moved away from the housing 12 to increase the distance between the endplates 14 as both upper and lower endplates move away from each other simultaneously in a uniform manner. Uniform expansion, of course, may be parallel or angular. In anterior-only angular expansion, the height of the spacer 10 at the anterior end is greater than the height of the spacer 10 at the posterior end as the upper and lower endplates move away from each other simultaneously only along the anterior side of the spacer leaving the posterior side in a low-profile, unexpanded condition and, thereby, creating an overall angulated or wedge-like profile for the spacer when viewed along the longitudinal axis. The expanded states are effected by a unique instrument 23 that selectably rotates only the anterior drive screw 20 or both the anterior drive screw 20 and the posterior drive screw 22. Rotation of the anterior and posterior screws 20, 22 moves the anterior actuator 16 and posterior actuator 18, respectively, along the longitudinal axis to wedge the upper and lower expanders 21 and attached upper and lower endplates 14 in a direction along an axis transverse to the longitudinal axis into one of the expanded states. Reverse rotation returns the spacer towards its collapsed configuration.

Figure 5A:
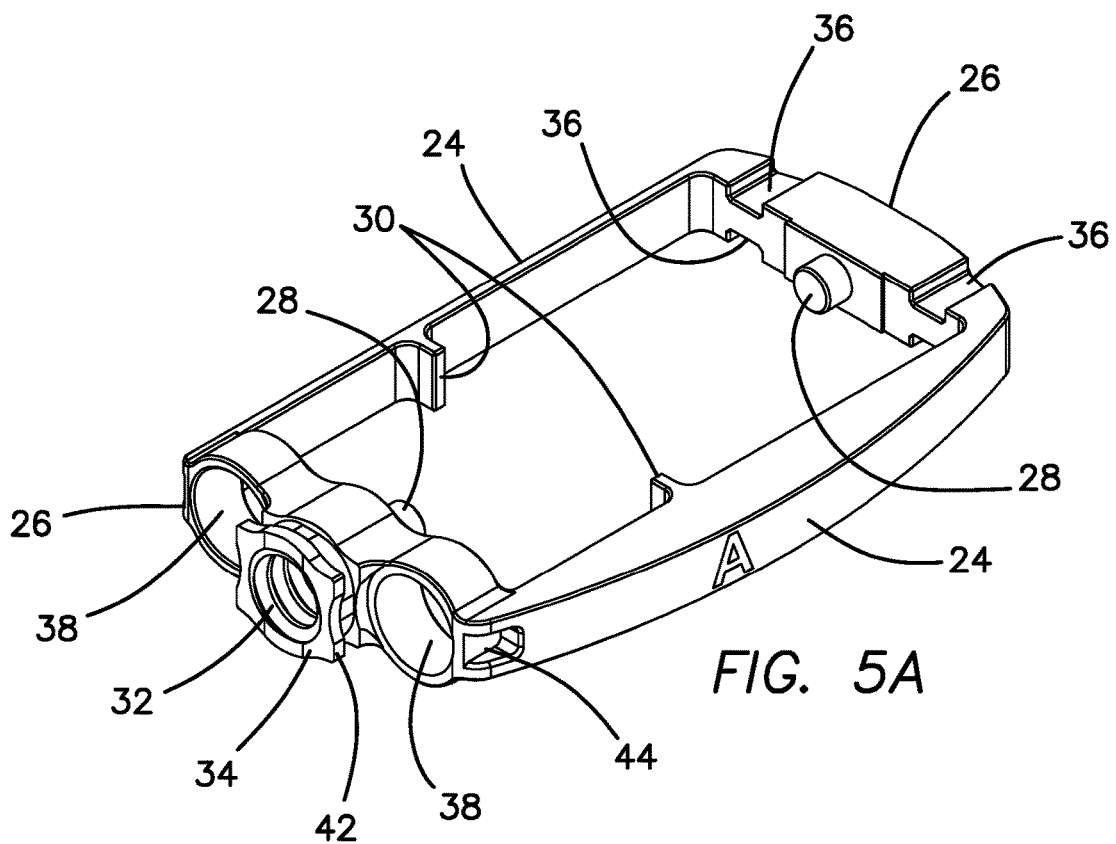
FIG. 5A is a proximal end, top perspective view of a housing of the expandable interbody spacer according to the present invention.
Figure 5B:
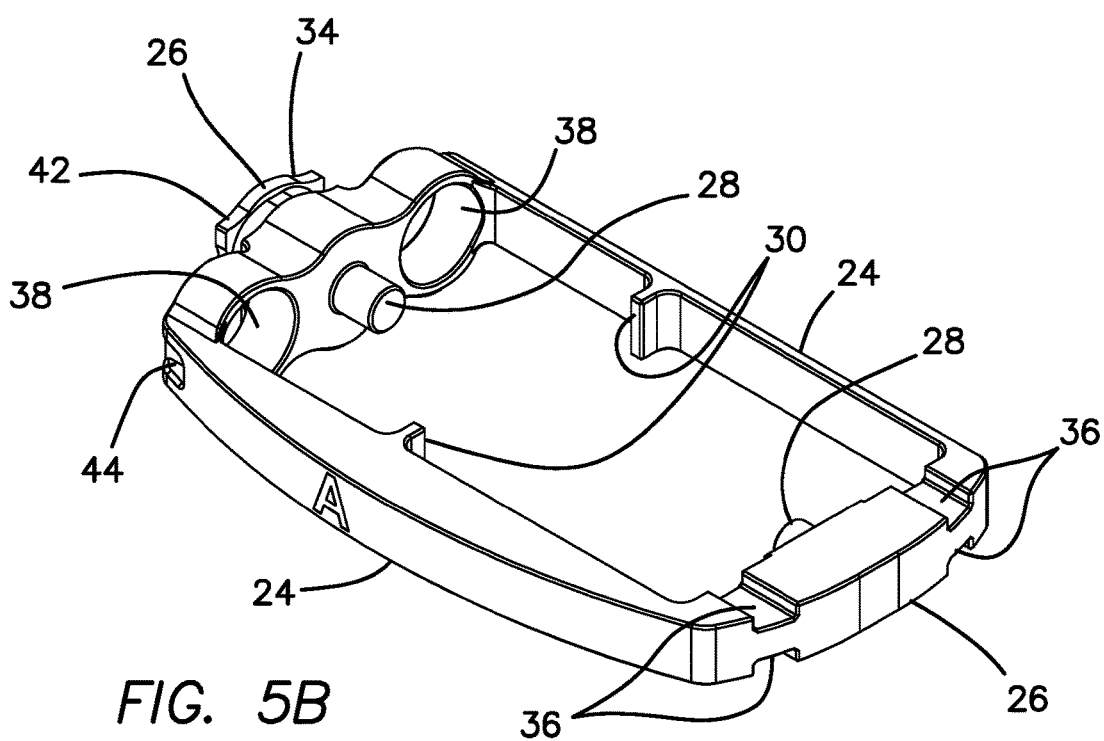
FIG. 5B is a distal end, top perspective view of the housing of FIG. 5A.
Figure 5C:
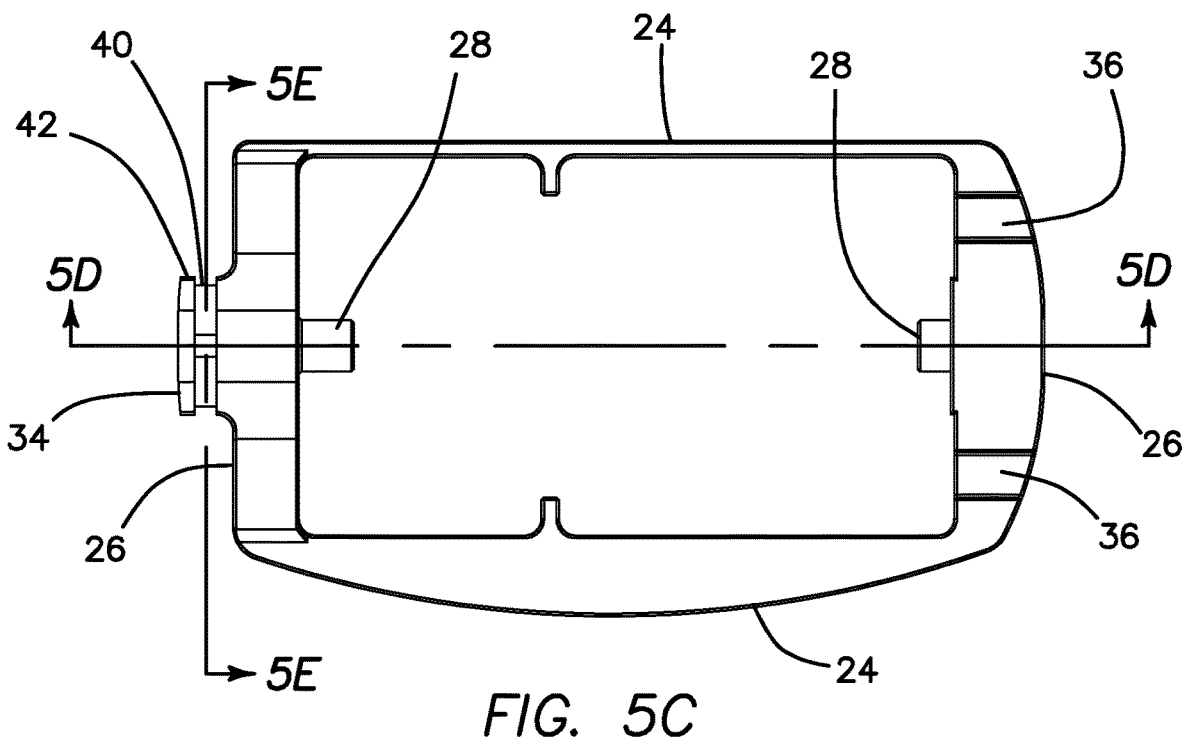
FIG. 5C is a top view of the housing of FIG. 5A.
Figure 5D:
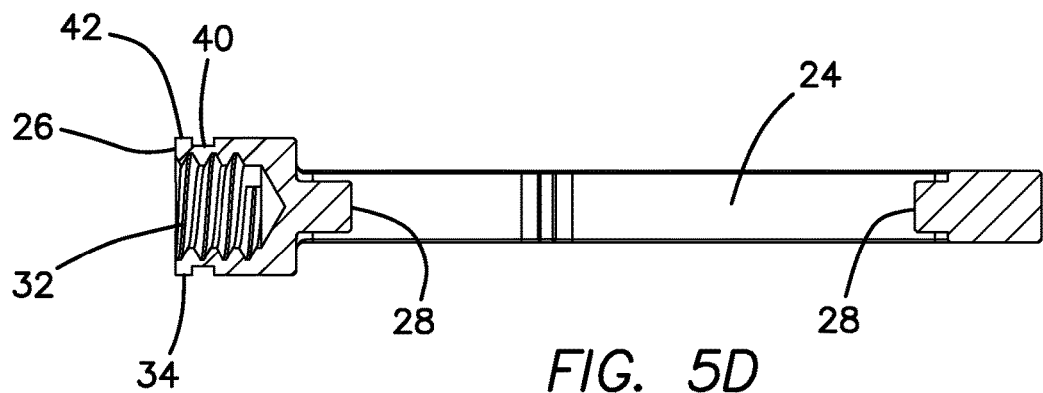
FIG. 5D is a cross-sectional view taken along line 5D-5D of the housing of FIG. 5C.
Figure 5E:
FIG. 5E is a cross-sectional view taken along line 5E-5E of the housing of FIG. 5C.
Figure 6A:
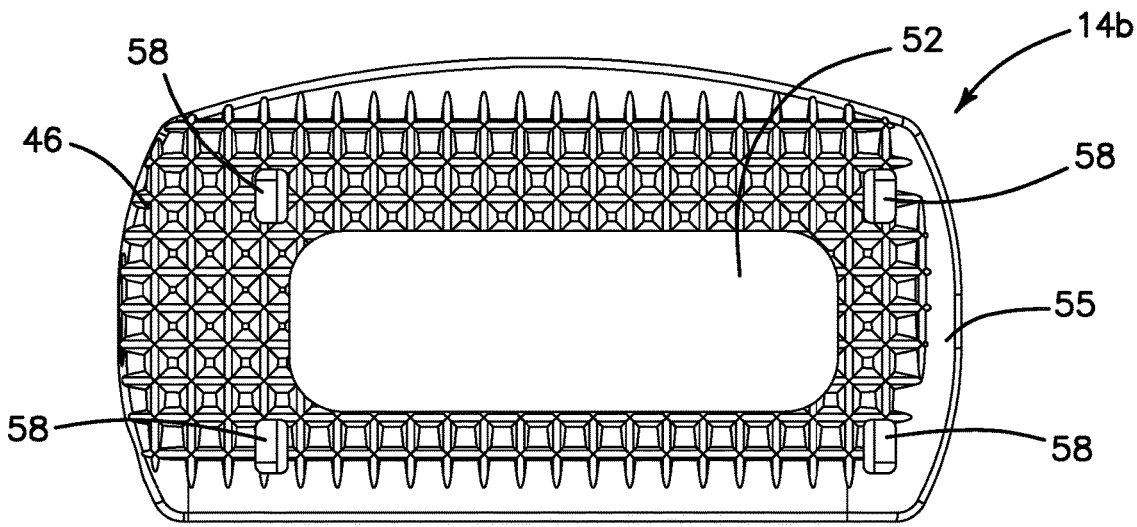
FIG. 6A is a top view of a lower endplate of the expandable interbody spacer according to the present invention.
Figure 6B:
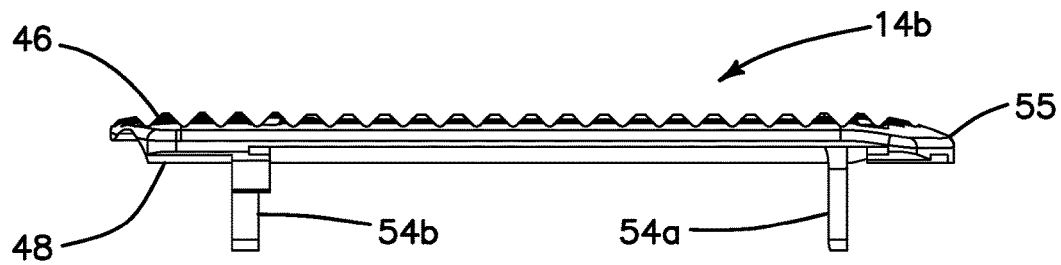
FIG. 6B is a posterior side elevational view of the endplate of FIG. 6A.
Figure 6C:
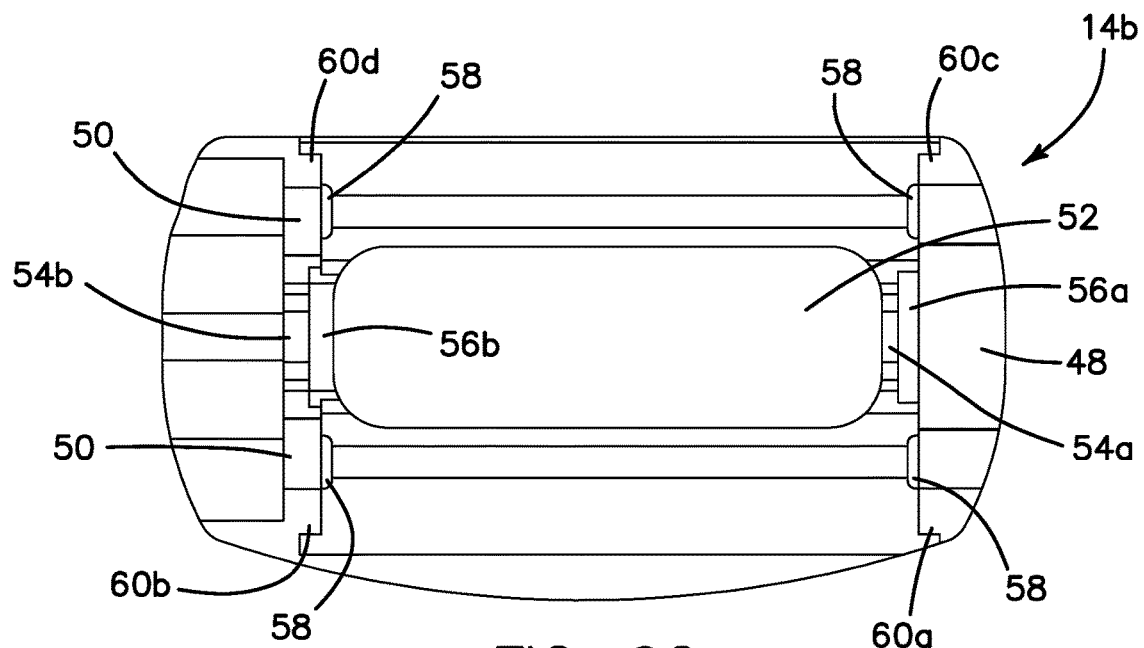
FIG. 6C is a bottom view of the endplate of FIG. 6A.
Figure 6D:
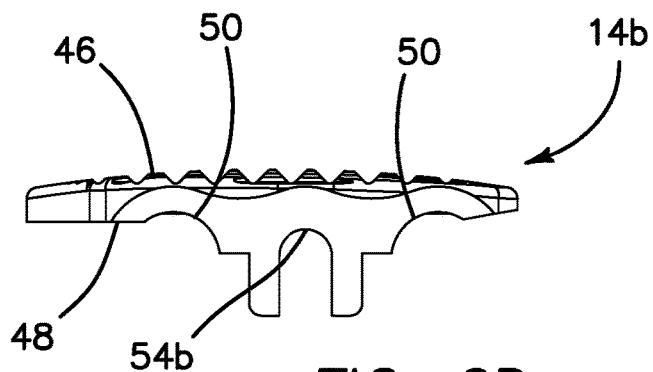
FIG. 6D is a proximal end elevational view of the endplate of FIG. 6A.
Figure 6E:
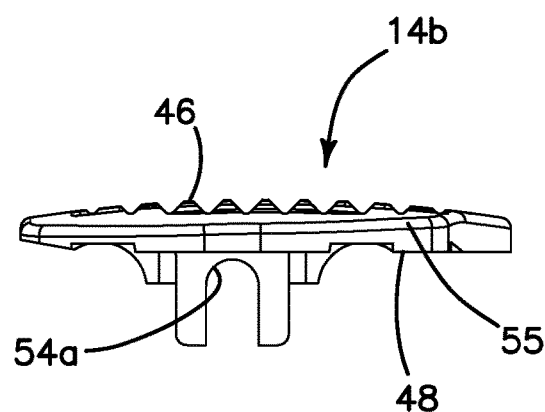
FIG. 6E is a distal end elevational view of the endplate of FIG. 6A.
Figure 7D:
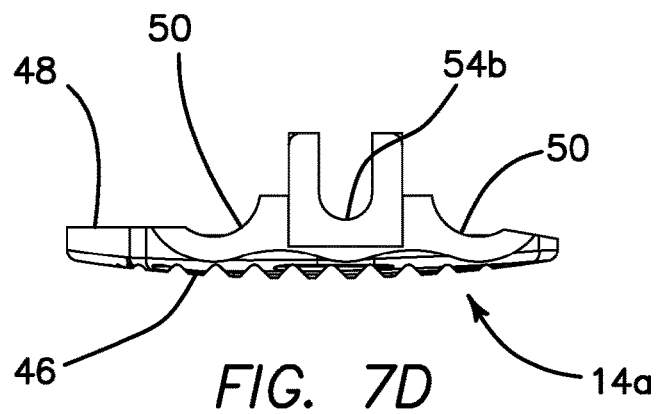
FIG. 7D is a proximal end elevational view of the endplate of FIG. 7A.
Figure 7E:
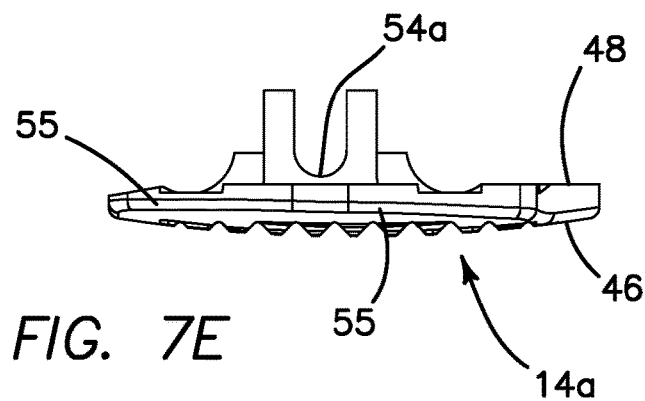
FIG. 7E is a distal end elevational view of the endplate of FIG. 7A.
Figure 7A:
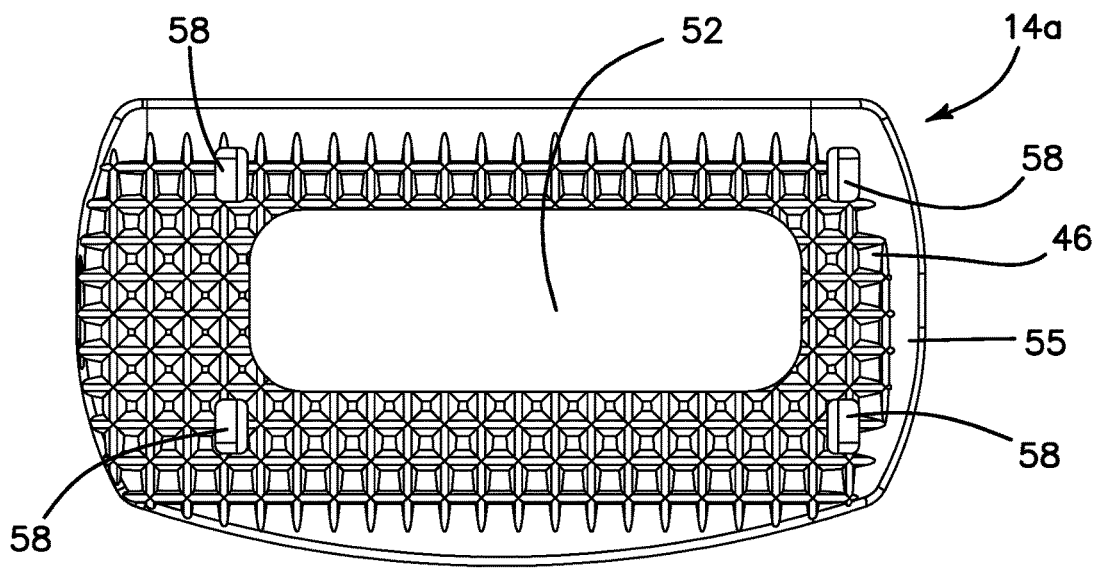
FIG. 7A is a top view of an upper endplate of the expandable interbody spacer according to the present invention.
Figure 7B:
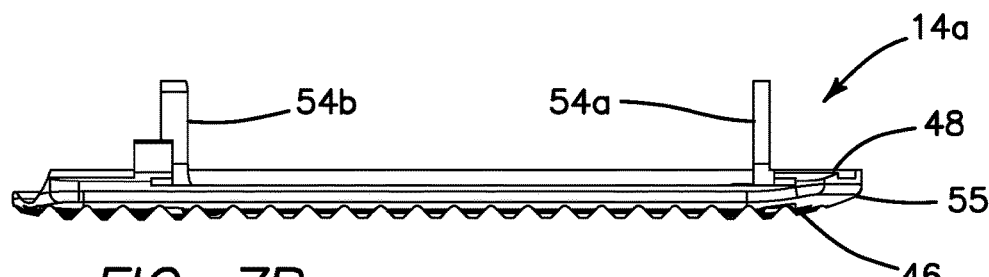
FIG. 7B is an anterior side elevational view of the endplate of FIG. 7A.
Figure 7C:
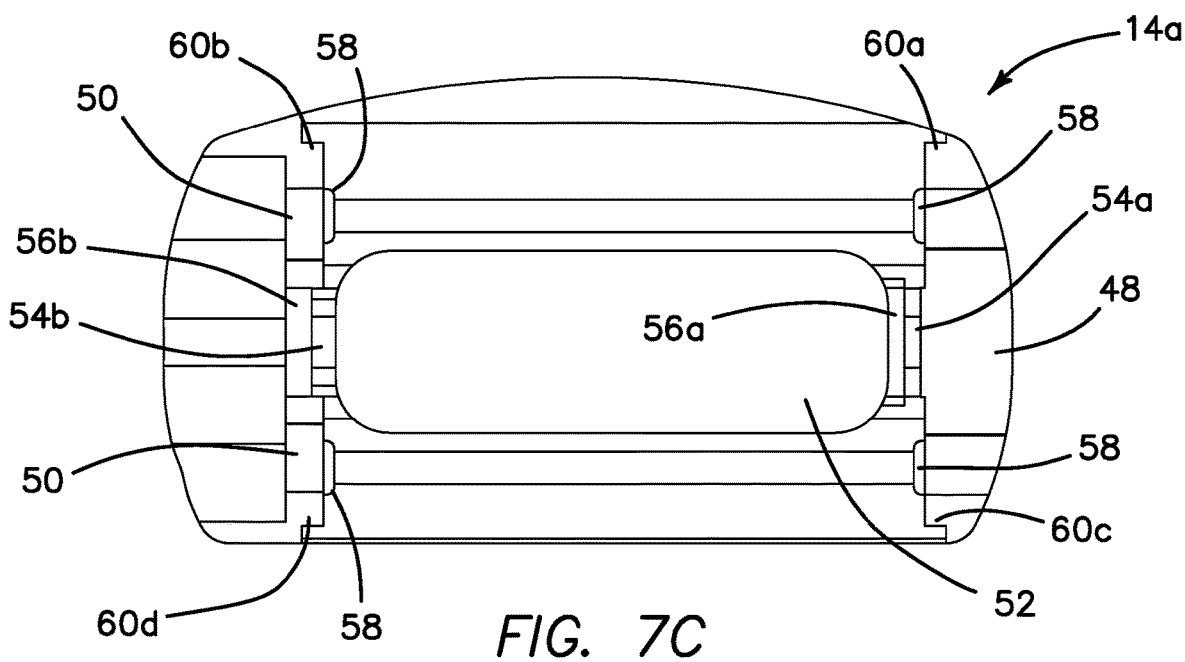
FIG. 7C is a bottom view of the endplate of FIG. 7A.

Turning now to FIGS. 5A-5E, the housing 12 will now be described in greater detail. The housing 12 includes two opposite sidewalls 24 interconnected by two opposite endwalls 26 that together define an open interior of the housing 12. A guidepost 28 is formed on the inner surface of each of the endwalls 26 and opposite from each other at the midline. The guideposts 28 are sized and configured to be seated within saddles 54 formed on the upper and lower endplates 14 to align and guide the endplates 14 with respect to the housing 12. The sidewalls 24 are substantially parallel to each other and of equal length with the anterior sidewall 24 bowing outwardly compared to the posterior sidewall 24. The endwalls 26 are substantially parallel to each other and approximately of equal length. Both the sidewalls and endwalls 26 define a rectangular-shaped housing 12 having a top end and bottom end that open to the interior of the housing 12. The top end and the bottom end are substantially parallel to each other and the sidewalls 24 have a constant height. The outer surface of the distal endwall 26 is slightly outwardly curved. The distal endwall 26 includes a pair of grooves 36 on the top end aligned with a pair of grooves 36 on the bottom end of the distal endwall 26. The grooves 36 are sized and configured to receive the distal prongs 89 of the anterior and posterior actuators 16, 18. The proximal endwall 26 includes a collar 34 extending proximally and defining a threaded rear opening 32 that opens into the housing 12. The threaded rear opening 32 is sized and configured to threadingly engage with the instrument 23, in particular, an inserter 160 for connecting the spacer 10 to the instrument 123. The threaded rear opening 32 is circular and the collar 34 has a non-circular outer surface defining a neck 40 as shown in FIG. 5E. The shape of the non-circular outer surface of the neck 40 corresponds to at least part of the shape of the retainer fingers 142 such that the retainer fingers 142 snap around the neck 40. The neck 40 of the collar 34 is located beneath a circumferentially flange 42. The length of the neck 40 is at least approximately twice the thickness of the retainer fingers 142 because both an anterior retainer 19a and a posterior retainer 19b snap around the neck 40 of the collar 34 in overlapping fashion. The height of proximal endwall 26 is greater than the height of the distal endwall 26. The proximal endwall 26 further includes two non-threaded circular openings 38 sized and configured to receive the proximal ends of the anterior and drive screws 20, 22. The anterior and posterior sidewalls 24 include notches 44 for engaging the instrument 23. The inner surface of each sidewall 24 includes a rib 30 extending in toward the longitudinal axis. The ribs 30 serves to constrain the expanders 21 in the pocket of the housing 12 so that the expanders 21 can only move in a direction transverse to the longitudinal axis towards the end plates 14.

Turning to FIGS. 6A-6E, the lower endplate 14b will now be described. The lower endplate 14b is connected to the housing 12 via expanders 21, anterior and posterior actuators 16, 18, anterior and posterior drive screws 20, 22 and retainers 19. The lower endplate 14b has a bone-engaging surface 46 and an interior surface 48 opposite from the bone-engaging surface 46. The bone-engaging surface 46 includes a plurality of tooth-like ridges. The ridges have pointed peaks to engage and increase the purchase on the adjacent vertebra between which the spacer 10 is located. The ridges may further be angled to help hold and directionally prevent migration of the spacer 10 relative to the adjacent vertebrae when implanted within the intervertebral space. The lower endplate 14b further includes a leading surface 55 that does not have tooth-like projections. The leading surface 55 is slightly angled to form a leading ramp-like surface at the distal end for easier penetration and distraction of the disc space as the spacer 10 is inserted. The lower endplate 14b includes at least one endplate opening 52 extending between the bone-engaging surface 46 and the interior surface 48 and opening to the interior of the housing 12. The endplate opening 52 reduces the weight of the spacer 10 and permits bone ingrowth to take place into the endplate 14. A family of bone graft materials, such as autograft, bone morphogenic protein (BMP), bone marrow aspirate, concentrate, stem cells and the like, may be placed inside the endplate openings 52 and into the interior of the housing 12 to promote bone growth into the spacer 10. The bone-engaging surface 46 of the upper and lower endplates 14a, 14b are substantially flat and parallel to each other when in the collapsed, low-profile unexpanded state as well as when in parallel expansion. The endplate 14b has a width and a length that is approximately equal to the overall width and length of the spacer 10 and approximately equal to the width and length of the housing 12. The lower endplate 14b includes a first U-shaped saddle 54a extending from the interior surface 48 for seating the guidepost 28 at the distal end of the housing 12 and a second U-shaped saddle 54b extending from the interior surface 48 for seating the guidepost 28 at the proximal end of the housing 12. A first saddle-receiving location 56a is formed adjacent and distal to the first saddle 54a on the lower end endplate 14b. A second saddle-receiving location 56b is formed adjacent and distal to the second saddle 54b on the lower endplate 14b. The first and second saddle-receiving locations 56a, 56b of the lower endplate 14b are sized and configured to receive the first and second saddles 54a, 54b of the upper endplate 14a, respectively. The first and second saddles 54a, 54b of the lower endplate 14b are offset from the first and second saddles 54a, 54b of the upper endplate 14a such that they overlap adjacent to each other along the longitudinal axis of the spacer 10. The interior surface 48 includes a concavity 50 on each side of the second saddle 54b. Each concavity 50 is sized and configured to accommodate and allow passage of the cylindrical proximal end of the anterior/posterior actuator 16, 18 to provide for a low-profile collapsed configuration. The interior surface 48 is slightly concave to accommodate the expanders 21. The lower endplate 14b includes four small apertures 58 extending through the lower endplate 14b from the bone-engaging surface 46 to the interior surface 48. The lower endplate 14b includes four slots 60a, 60b, 60c, 60d sized and configured to receive the projections 72 of the two lower expanders 21c, 21d in order to connect the lower endplate 14b to the lower expanders 21c, 21d. Two slots 60a, 60b are on the anterior side of the spacer 10. The slots 60 are elongated and extend from near the anterior edge of the lower endplate 14b toward the longitudinal axis to overlap with the small apertures 58 such that each slot 60 is in communication with the apertures 58. The depth of each slot 60 is approximately equal to the length of each projection 72 on the expander 21. The lower expander 21c is connected to the lower endplate 14b by aligning the projections 72 on both ends of the expander 21c with the entryway into slots 60a, 60b along the anterior side of the lower endplate 14b. The expander 21c is moved laterally into the slots 60a, 60b toward the longitudinal axis such that the projections reside generally in the location of the apertures 58. Two slots 60c, 60d are on the posterior side of the spacer 10. The slots 60 are elongated and extend from near the posterior edge of the lower endplate 14b toward the longitudinal axis to overlap with small apertures 58. The lower expander 21d is connected to the lower endplate 14b by aligning the projections 72 on both ends of the expander 21d with the entryway into slots 60d, 60d along the posterior side of the lower endplate 14b. The lower expander 21d is moved laterally into the slots 60c, 60d toward the longitudinal axis such that the projections reside generally in the location of the apertures 58.

Turning to FIGS. 7A-7E, the upper endplate 14a will now be described. The upper endplate 14a is connected to the housing 12 via expanders 21a, 21b, anterior and posterior actuators 16, 18, anterior and posterior drive screws 20, 22 and retainers 19. The upper endplate 14a has a bone-engaging surface 46 and an interior surface 48 opposite from the bone-engaging surface 46. The bone-engaging surface 46 includes a plurality of tooth-like ridges. The ridges have pointed peaks to engage and increase the purchase on the adjacent vertebra between which the spacer 10 is located. The ridges may further be angled to help hold and directionally prevent migration of the spacer 10 relative to the adjacent vertebrae when implanted within the intervertebral space. The upper endplate 14a further includes a leading surface 55 that does not have tooth-like projections. The leading surface 55 is slightly tapered/angled to form a leading ramp-like surface at the distal end for easier penetration and distraction of the disc space as the spacer 10 is inserted. The upper endplate 14a includes at least one endplate opening 52 extending between the bone-engaging surface 46 and the interior surface 48 and opening to the interior of the housing 12. The endplate opening 52 reduces the weight of the spacer 10 and permits bone ingrowth to take place into the endplate 14a. A family of bone graft materials, such as autograft, bone morphogenic protein (BMP), bone marrow aspirate, concentrate, stem cells and the like, may be placed inside the endplate opening 52 and into the interior of the housing 12 to promote bone growth into the spacer 10. The bone-engaging surface 46 of the upper and lower endplates 14a, 14b are substantially flat and parallel to each other when in the collapsed, low-profile unexpanded state as well as when in parallel expansion. The upper endplate 14a has a width and a length that is approximately equal to the overall width and length of the spacer 10 and approximately equal to the width and length of the housing 12. The upper endplate 14a includes a first U-shaped saddle 54a extending from the interior surface 48 for seating the guidepost 28 at the distal end of the housing 12 and a second U-shaped saddle 54b extending from the interior surface 48 for seating the guidepost 28 at the proximal end of the housing 12. A first saddle-receiving location 56a is formed adjacent and proximal to the first saddle 54a on the upper endplate 14a. A second saddle-receiving location 56b is formed adjacent and proximal to the second saddle 54b on the upper endplate 14a. The first and second saddle-receiving locations 56a, 56b of the upper endplate 14a are sized and configured to receive the first and second saddles 54a, 54b of the lower endplate 14b, respectively. The first and second saddles 54a, 54b of the upper endplate 14a are offset from the first and second saddles 54a, 54b of the lower endplate 14b such that they overlap adjacent to each other along the longitudinal axis of the spacer 10. The interior surface 48 includes a concavity 50 on each lateral side of the second saddle 54b. Each concavity 50 is sized and configured to accommodate and allow passage of the cylindrical proximal end of the anterior/posterior drive screws 20, 22 to provide for a low-profile collapsed configuration. The interior surface 48 is slightly concave to accommodate the expanders 21. The upper endplate 14a includes four small apertures 58 extending through the upper endplate 14a from the bone-engaging surface 46 to the interior surface 48. The upper endplate 14a includes four slots 60a, 60b, 60c, 60d sized and configured to receive the projections 72 of the two upper expanders 21a, 21b in order to connect the upper endplate 14a to the upper expanders 21a, 21b. Two slots 60a, 60b are on the anterior side of the spacer 10. The slots 60a, 60b are elongated and extend from near the anterior edge of the upper endplate 14a toward the longitudinal axis to overlap with small apertures 58. Each slot 60 is in communication with the apertures 58. The depth of each slot 60 is approximately equal to the length of each projection on the expander 21. The upper expander 21a is connected to the upper endplate 14a by aligning the projections on both ends of the upper expander 21a with the entryway into slots 60a, 60b along the anterior side of the upper endplate 14a. The upper expander 21a is moved laterally into the slots 60a, 60b toward the longitudinal axis such that the projections 72 reside generally in the location of the apertures 58. Two slots 60c, 60d are on the posterior side of the spacer 10. The slots 60c, 60d are elongated and extend from near the posterior edge of the upper endplate 14a toward the longitudinal axis to overlap with small apertures 58. The upper expander 21b is connected to the upper endplate 14a by aligning the projections on both ends of the upper expander 21b with the entryway into slots 60c, 60d along the posterior side of the upper endplate 14a. The upper expander 21b is moved laterally into the slots 60c, 60d toward the longitudinal axis such that the projections 72 reside generally in the location of the apertures 58.

Figure 8A:
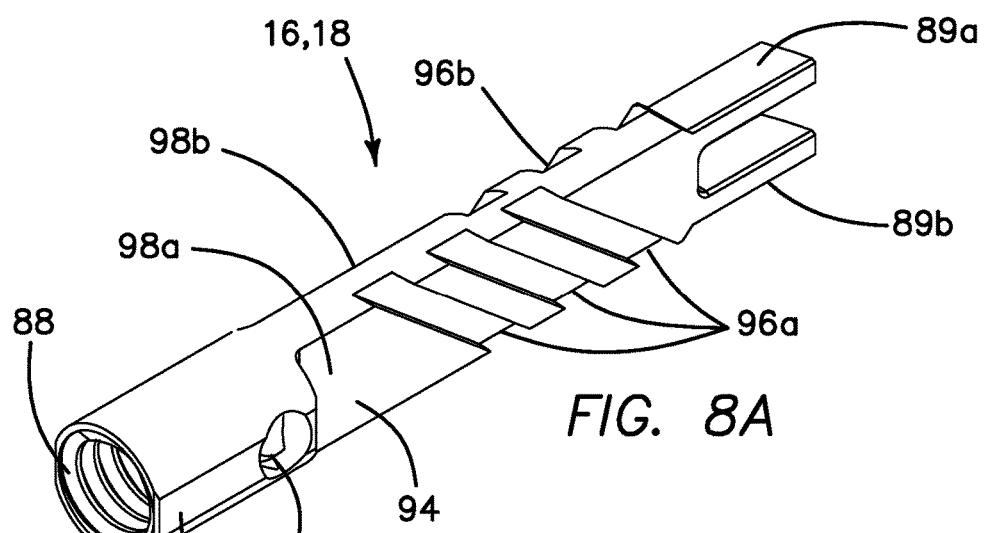
FIG. 8A is a proximal end, top perspective view of a posterior actuator of the expandable interbody spacer according to the present invention.
Figure 8B:
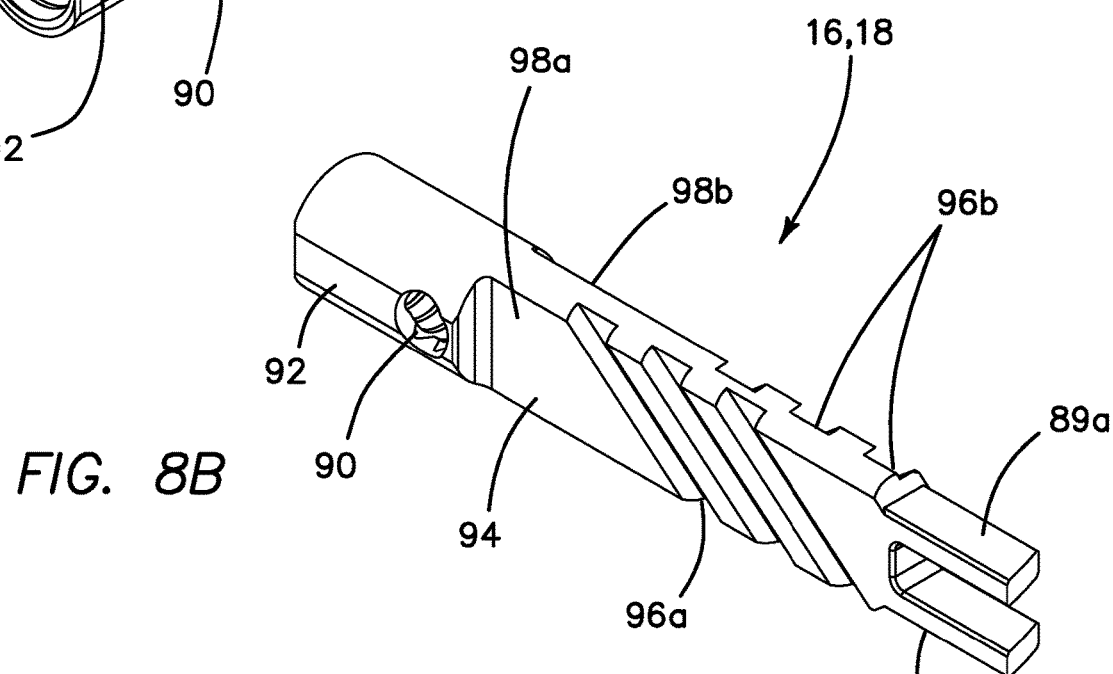
FIG. 8B is a distal end, top perspective view of the posterior actuator of FIG. 8A.
Figure 8C:
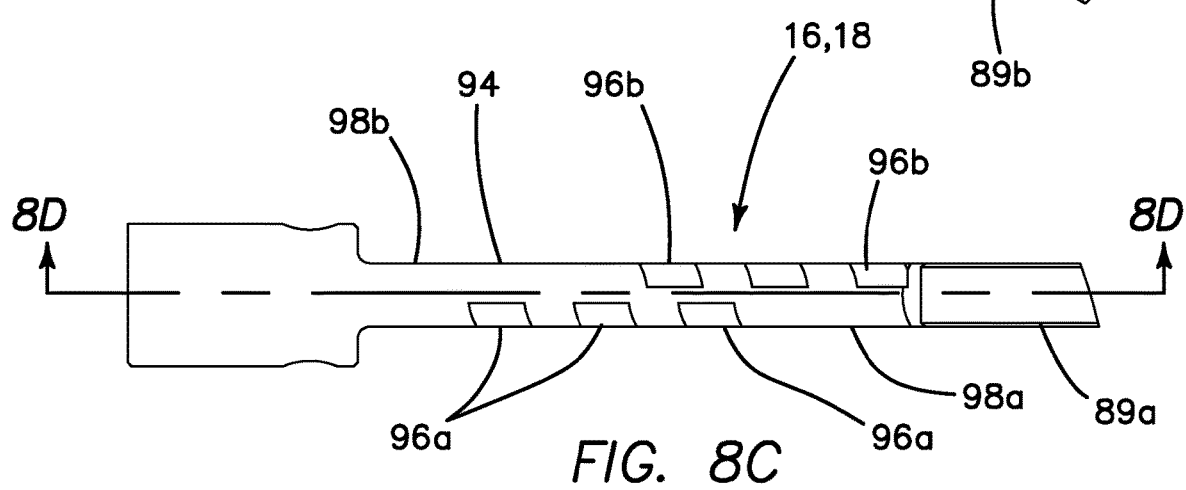
FIG. 8C is a top view of the posterior actuator of FIG. 8A.
Figure 8D:
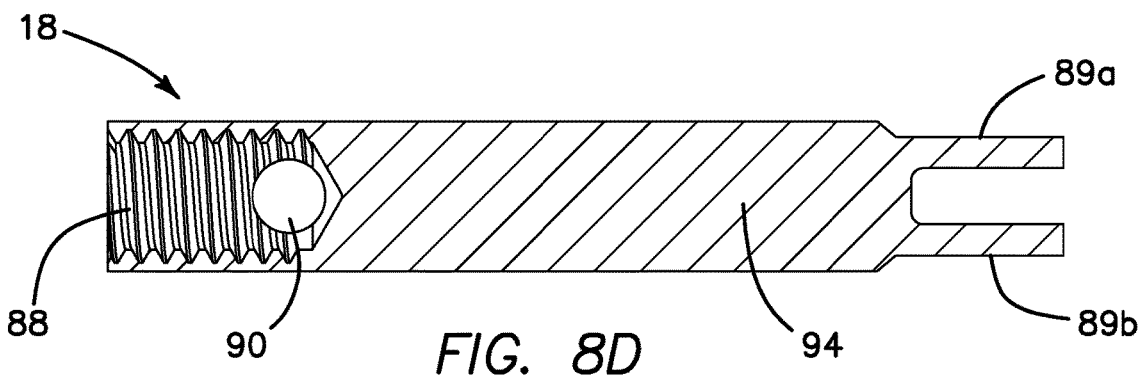
FIG. 8D is a cross-sectional view taken along line 8D-8D of the posterior actuator of FIG. 8C.
Figure 8E:
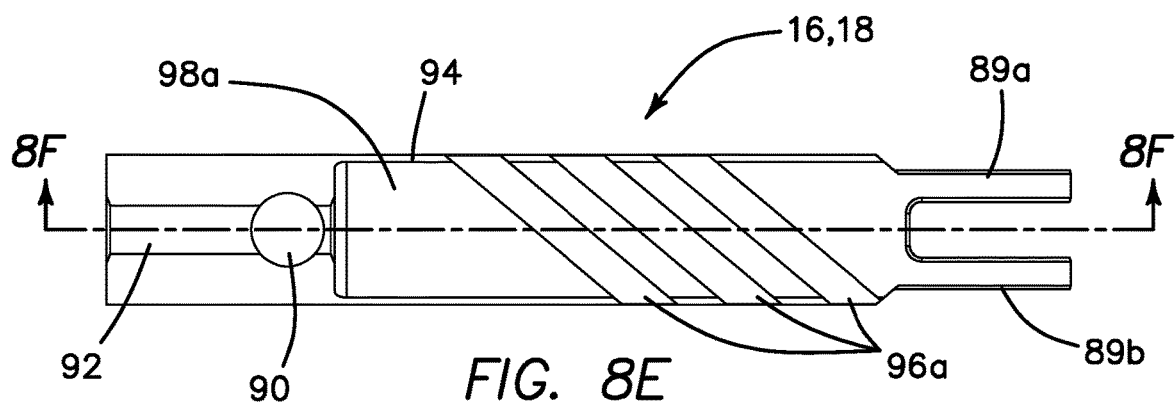
FIG. 8E is a side elevational view of the posterior actuator of FIG. 8A.
Figure 8F:
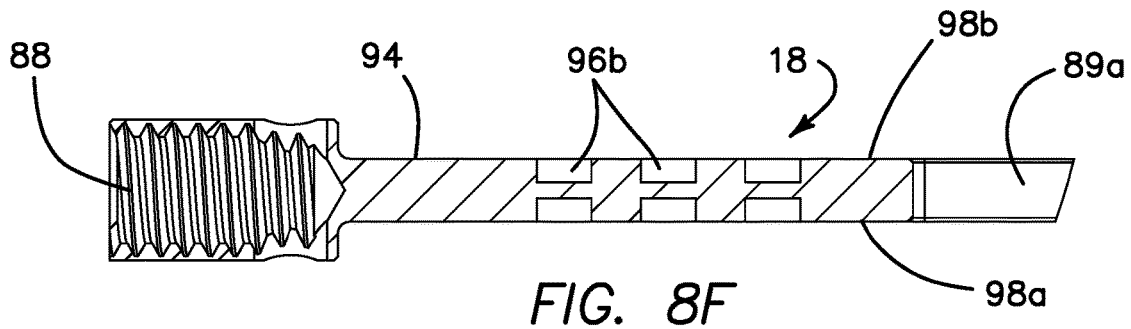
FIG. 8F is a cross-sectional view taken along line 8F-8F of the posterior actuator of FIG. 8E.
Figure 8G:
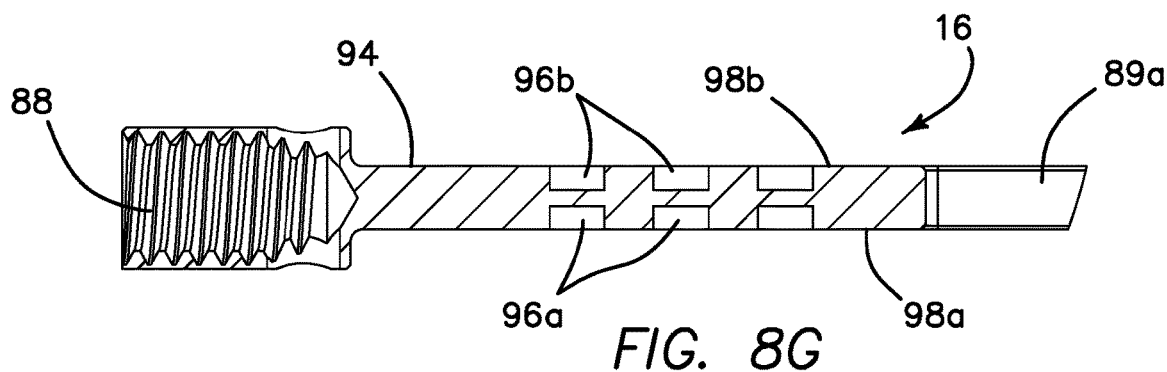
FIG. 8G is a cross-sectional view taken along line 8F-8F of FIG. 8E of an anterior actuator according to the present invention.
Figure 9A:
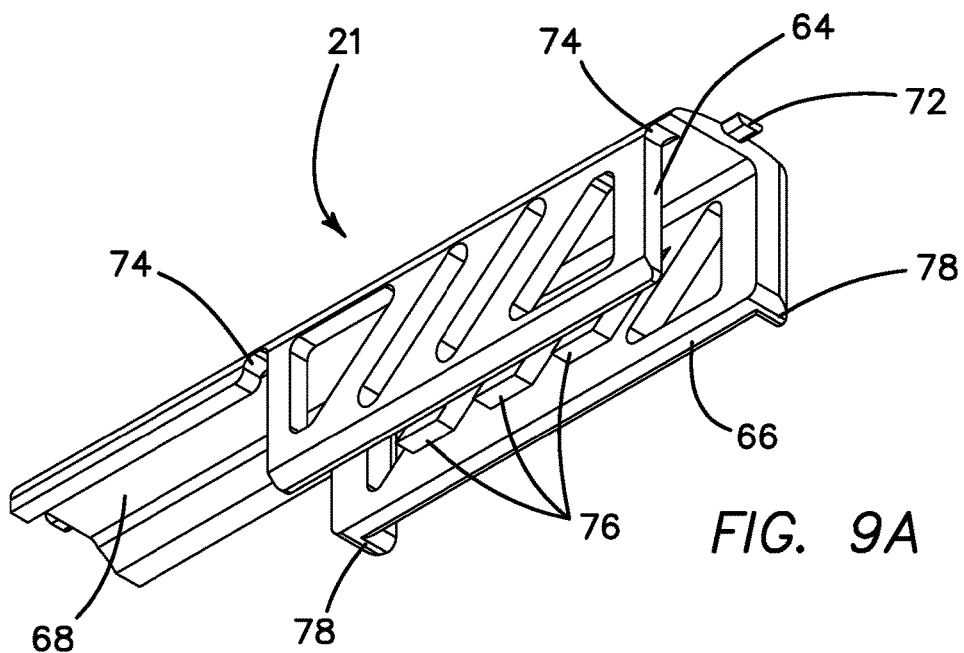
FIG. 9A is a bottom perspective view of an expander of the expandable interbody spacer according to the present invention.
Figure 9B:
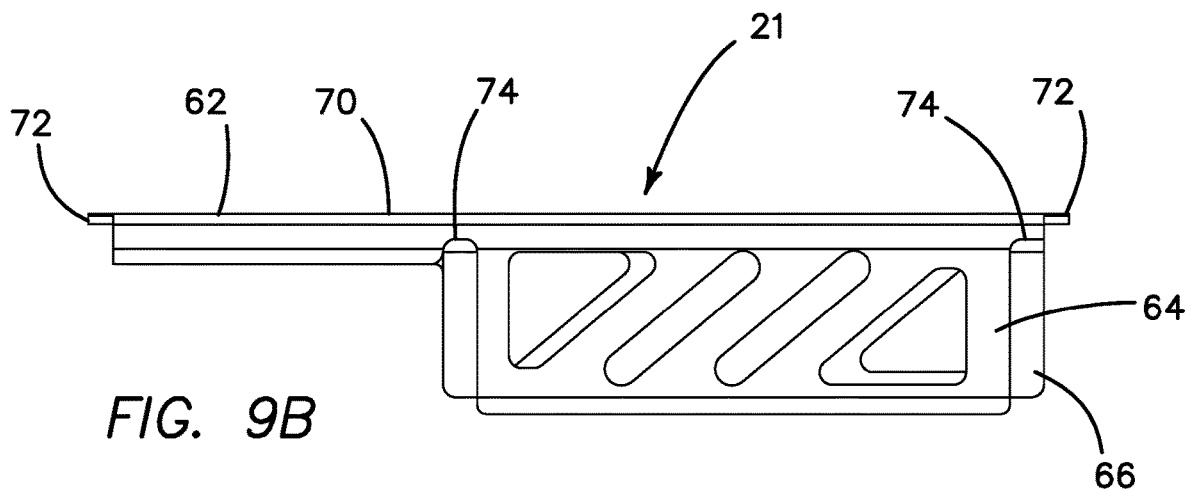
FIG. 9B is an anterior side elevational view of the expander of FIG. 9A.
Figure 9C:
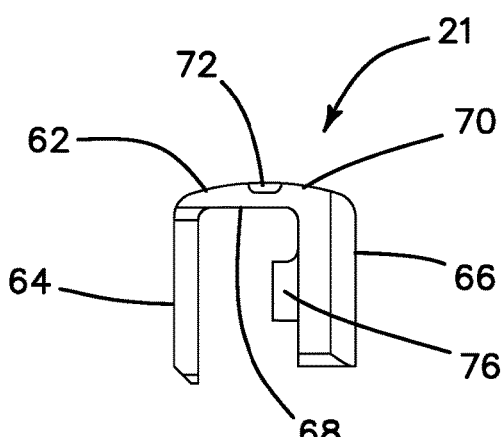
FIG. 9C is a distal end elevational view of the expander of FIG. 9A.
Figure 9D:
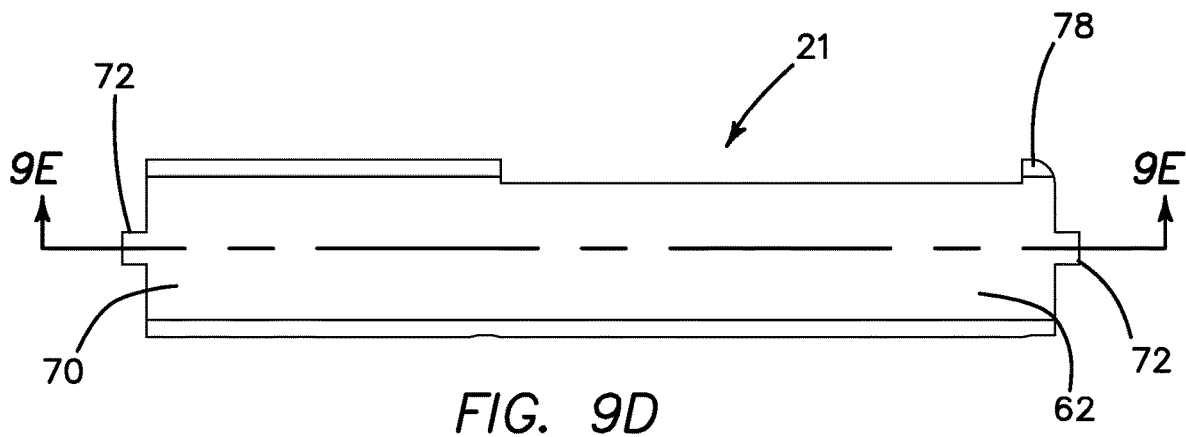
FIG. 9D is a top view of the expander of FIG. 9A.
Figure 9E:
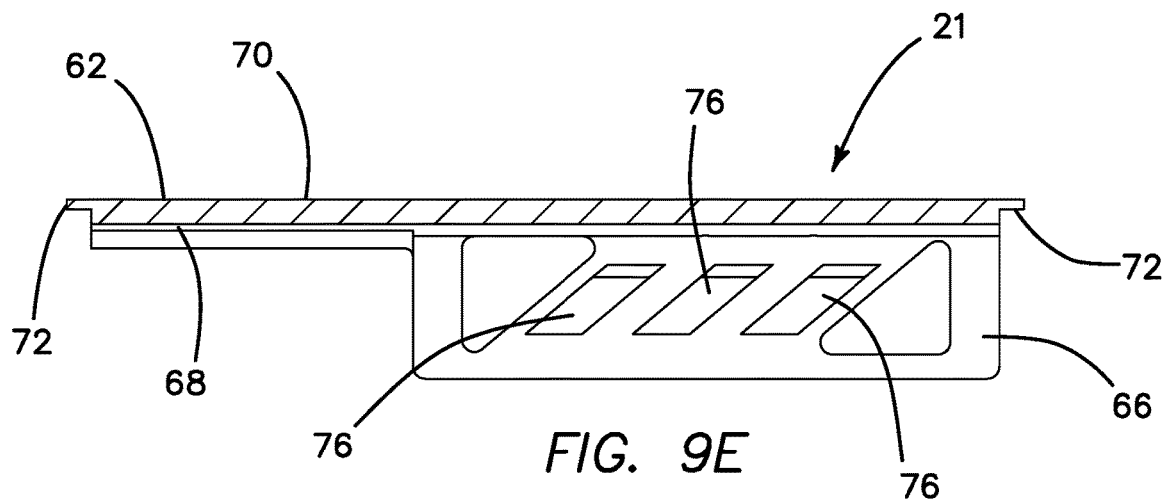
FIG. 9E is a cross-sectional view taken along line 9E-9E of the expander of FIG. 9D.
Figure 9F:
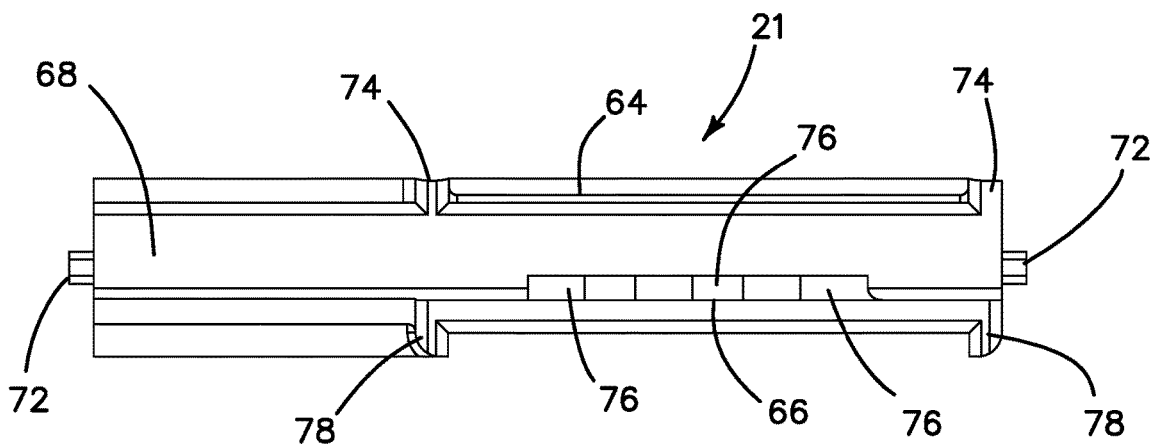
FIG. 9F is a bottom view of the expander of FIG. 9A.
Figure 10A:
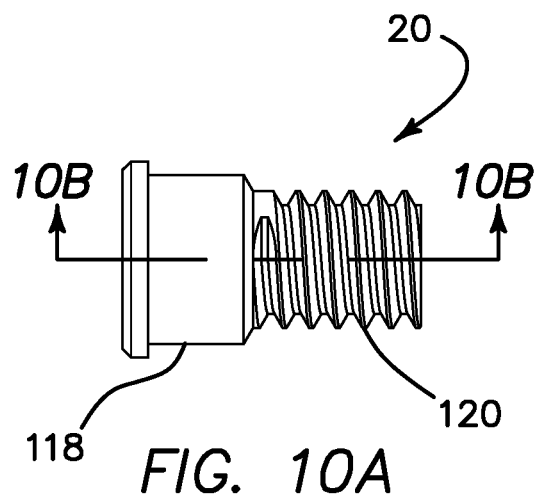
FIG. 10A is a side elevational view of an anterior threaded actuator according to the present invention.
Figure 10B:
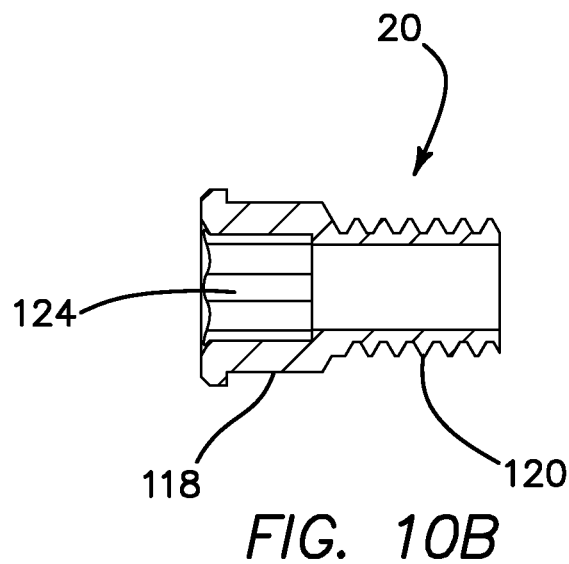
FIG. 10B is a cross-sectional view taken along line 10B-10B of the anterior threaded actuator of FIG. 10A.

Turning now to FIGS. 8A-8G, the anterior actuator 16 and the posterior actuator 18 will now be described in greater detail. The anterior and posterior actuators 16, 18 are elongated members having forked distal ends. Each forked distal end includes two flattened prongs 89, an upper prong 89a and a lower prong 89b, that are parallel to each other. The proximal end of each of the actuators 16, 18 includes a threaded bore 88. The threaded bore 88 of the anterior actuator 16 is sized and configured to receive the anterior drive screw 20 and has a right-handed thread as shown in FIG. 8G. The threaded bore 88 of the posterior actuator 18 is sized and configured to receive the posterior threaded drive screw 22 and has a left-handed thread as shown in FIGS. 8D and 8F. An opening 90 extends laterally through the cylindrical proximal end of each actuator 16, 18 such that the opening 90 is perpendicular to the longitudinal axis of each actuator 16, 18. The opening 90 permits bone graft material to be placed inside or grow into the opening. The cylindrical proximal ends of the actuators 16, 18 include side flats 92 for aligning the actuator 16, 18 within the housing 12. Each actuator 16, 18 includes a flattened middle portion 94 located between the cylindrical proximal end and the forked distal end. The middle portion 94 has a rectangular-like cross-section such that a flat anterior side 98a is vertical and parallel to a flat posterior side 98b. The anterior side 98a of each actuator 16, 18 includes angled grooves 96a sized and configured to engage and mate with corresponding projections on the lower expanders 21c, 21d to translate the lower endplate 14b. The posterior side 98b of each actuator 16, 18 includes angled grooves 96b sized and configured to engage and mate with projections on the upper expanders 21a, 21b to translate the upper endplate 14a. The grooves 96a are angled and extend from the top edge of the actuator 16, 18 distally to the bottom edge of the actuator 16, 18; whereas, the grooves 96b on the posterior side 98b are ramped in the opposite direction. In particular, the grooves 96b are angled and extend from the top edge of the actuator 16, 18 proximally to the bottom edge of the actuator 16, 18.

Turning now to FIGS. 9A-9F, the expanders 21 will now be described in greater detail. The spacer 10 employs four identical expanders 21, two upper expanders 21a, 21b and two lower expanders 21c, 21d. Each expander 21 has a first rail 64 and a second rail 66 parallel to and spaced apart from each other and extending perpendicularly from an inner surface 68 of a base 62. The base 62 has a convex outer surface 70 that conforms to the interior surface 48 of the endplates 14. At the edge of the outer surface 70 at both the distal and proximal ends of the expander 21, a projection 72 is provided for insertion into and connection to the slots 60 on the endplates 14. The first rail 64 is shorter along the longitudinal axis than the second rail 66 and notches 74 are formed at the proximal and distal ends of the first rail 64. These notches 74 are sized and configured to receive the second rail 66 of an upper expander 21. The first rail 64 has a plurality of openings to reduce the weight of the device and to allow for bone ingrowth. The second rail 66 includes three ramped projections 76 on the inner surface of the second rail 66. These ramped projections 76 are sized and configured for mating with the grooves 96 on the actuators 16, 18. The second rail 66 is indented from the edge of the second rail 66 forming perpendicular end portions 78 that seat within the notches 74 at the first rail 64 when the upper expander 21a, 21b is inverted to mate with a corresponding lower expander 21c, 21d. When mated together, the first rail 64 is offset from the second rail 66 with the first rail 64 of a lower expander 21c, 21d being adjacent to the second rail 66 of an upper expander 21a, 21b and the second rail 66 of the lower expander 21c, 21d being adjacent to the first rail 64 of an upper expander 21a, 21b. This arrangement permits an interlocking low profile when the device is in a collapsed configuration. The second rail 66 has a couple of openings to reduce weight and permit bone ingrowth.

Figure 11A:
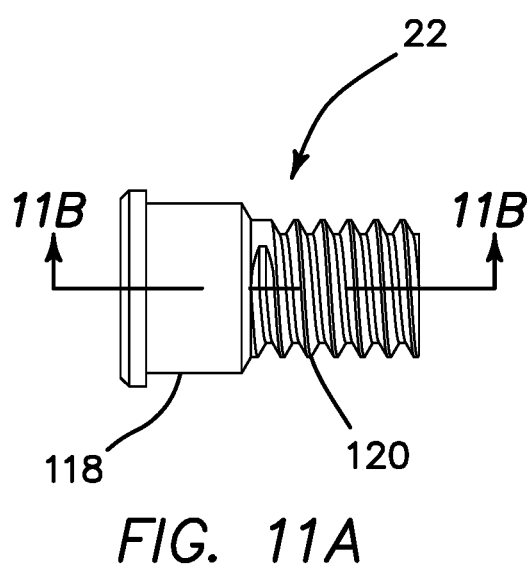
FIG. 11A is a side elevational view of a posterior threaded actuator according to the present invention.
Figure 11B:
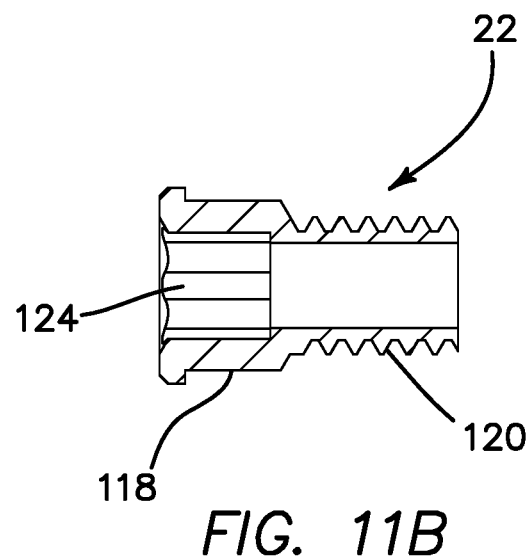
FIG. 11B is a cross-sectional view taken along line 11B-11B of the posterior threaded actuator of FIG. 11A.

Turning now to FIGS. 10A-11B, the anterior and posterior drive screws 20, 22 will now be described. The anterior drive screw 20 will be described in reference to FIGS. 10A-10B. The anterior drive screw 20 includes a head 118 at a proximal end connected to a threaded shank portion 120 that extends toward a distal end. The head 118 has a cylindrical shape. The diameter of the head 118 is larger than the diameter of the threaded shank 120. As can be seen in FIG. 10B, the anterior drive screw 20 includes a drive bore 124 that extends from a proximal opening in the head 118. The drive bore 124 has a hexalobe shape or hexagonal shape in cross-section along the entire length of the bore 124. The drive bore 124 is sized and configured to be engaged to rotate the drive screw 20 by an instrument 23. The bore 124 may have any non-circular cross-sectional shape that corresponds to and is sized and configured to mate with on the drive portion of the instrument 23. The posterior drive screw 22 will be described in reference to FIGS. 11A-11B wherein like reference numbers are used to describe like parts. The posterior drive screw 22 includes a head 118 at a proximal end connected to a threaded shank portion 120 that extends toward the distal end. The head 118 has a cylindrical shape. The diameter of the head 118 is larger than the diameter of the threaded shank 120. As can be seen in FIG. 11B, the posterior drive screw 22 includes a drive bore 124 that extends from an opening at the proximal end toward the distal end. The drive bore 124 has a hexalobe or hexagonal cross-sectional shape. The drive bore 124 is sized and configured to be matingly engaged for rotation by the instrument 23. The bore 124 may have any non-circular cross-sectional shape that corresponds to and is sized and configured to mate with on the drive portion of the instrument 23. The threaded shanks 120 of the anterior and posterior drive screws 20, 22 have the same length, the same size thread and the same number of threads per inch. However, the helical threaded shank 120 of the posterior drive screw 22 has a left-handed thread; whereas, the helical threaded shank 120 of the anterior drive screw 20 has a right-handed thread. Viewing from the proximal end, the direction of translation with respect to the housing 12 of the anterior drive screw 20 is distal when rotated in the clockwise direction and the direction of translation of the posterior drive screw 20 is proximal when rotated in the clockwise direction. In essence, the direction of threads on one of the anterior drive screw and posterior drive screw is opposite to the direction of threads on the other of the one of the anterior drive screw and posterior drive screw such that they correspond to the direction of the threads on the bores 88 of anterior and posterior actuators. The advantage of this difference will be described in greater detail below.

Figure 12A:
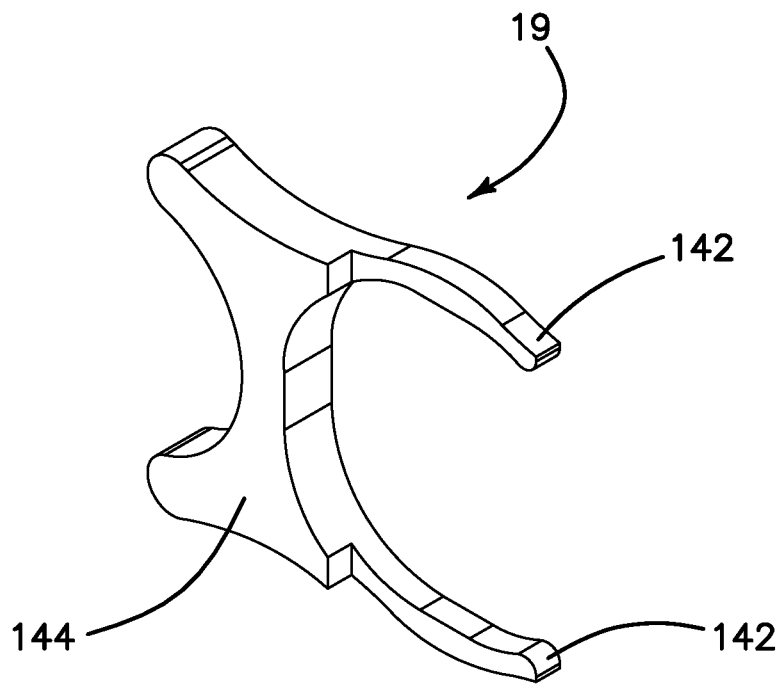
FIG. 12A is a top perspective view of an actuator retainer according to the present invention.
Figure 12B:
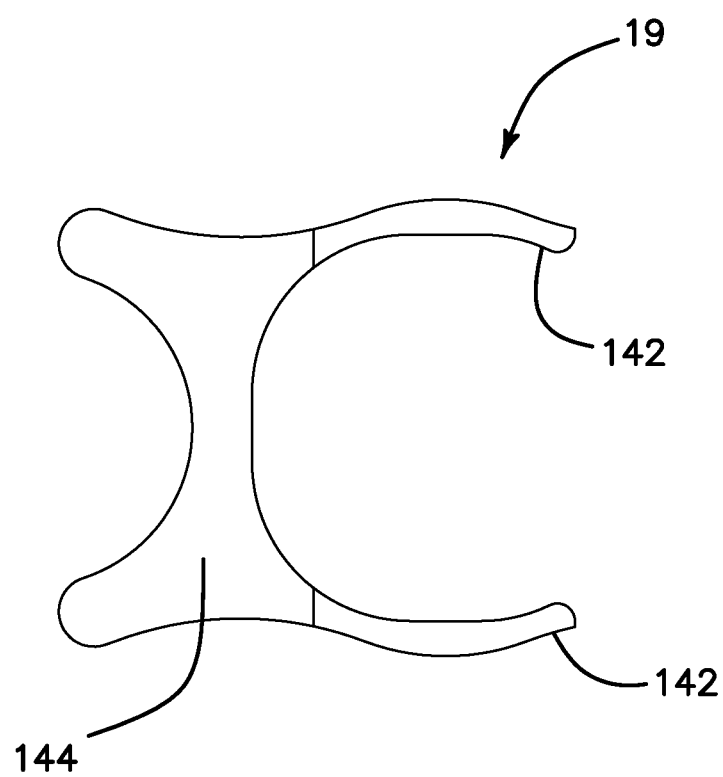
FIG. 12B is a side elevational view of the actuator retainer of FIG. 12A.

Turning now to FIGS. 12A-12B, the anterior and posterior actuator retainers 19a, 19b will now be described in greater detail. The retainers 19a, 19b are identical clips having two curved retainer fingers 142 extending from a retainer body 144. The fingers 142 are in the same plane as the body 144. The thickness of the fingers 142 is approximately half the thickness of the retainer body 144. The fingers 142 of the anterior retainer 19a are configured to overlap with the fingers 144 of the posterior retainer 19b around the collar 34 of the housing 12 and be retained underneath the flange 42 of the collar 34. When overlapped with each other, the thickness of the fingers 142 is approximately equal to the thickness of the retainer body 144 and the length of the collar 34 underneath the flange 42. The retainer fingers 142 are curved to form a partial circle corresponding to at least part of the cross-sectional shape of the collar 34. When moved against the collar 34 the retainer fingers 142 will flex slightly outwardly away from each other and then snap back around which the neck of the collar 34 of the housing 12 and underneath the circumferential flange 42. The length of the collar 34 is at least approximately twice the thickness of the retainer fingers 142 because an anterior retainer 19a and a posterior retainer 19b snap around the neck 40 of the collar 34 in overlapping fashion. The retainer body 144 forms a semi-circular shape and is sized and configured to block and retain the drive screws 20, 22 and associated actuators 16, 18. The body 144 of anterior actuator retainer 19a will extend in the anterior direction away from the collar 34 to block and retain the anterior drive screw 20 and anterior actuator 16 and the body 144 of the posterior actuator retainer 19b will extend in the posterior direction away from the collar 34 to block and retain the posterior drive screw 22 and posterior actuator 18.

The expandable interbody spacer 10 is assembled by orientating the upper endplate 14a such that the interior surface 48 faces upwardly. One upper expander 21a is connected to the upper endplate 14a by inserting the distal and proximal projections 72 of the expander 21a into the distal and proximal anterior slots 60a, 60b and moving the expander 21a medially into position within the slots 60a, 60b. Another upper expander 21b is connected to the upper endplate 14a by inserting the distal and proximal projections 72 of the expander 21b into the distal and proximal posterior slots 60c, 60d and moving the expander 21b medially into position within the slots 60c, 60d. The lower endplate 14b is oriented such that the interior surface 48 faces upwardly. One lower expander 21c is connected to the lower endplate 14b by inserting the distal and proximal projections 72 of the expander 21c into the distal and proximal anterior slots 60a, 60b and moving the expander 21c medially into position within the slots 60a, 60b. Another lower expander 21d is connected to the lower endplate 14b by inserting the distal and proximal projections 72 of the expander 21d into the distal and proximal posterior slots 60c, 60d and moving the expander 21d medially into position within the slots 60c, 60d. The anterior actuator 16 and the posterior actuator 18 are inserted into through the openings 38 of the housing 12 and the upper and lower expander/endplate subassemblies are inserted into the actuators 16, 18 and housing 12. The distal prongs 89 of the actuators 16, 18 are located in the grooves 36 of the housing 12 and the anterior drive screw 20 is threaded into the anterior actuator 16 and the posterior drive screw 22 is threaded into the posterior actuator 18 connecting the expander/endplate subassemblies to the housing 12. The anterior retainer 19a is snapped around the collar 34 of the housing 12 with the retainer body 144 blocking the anterior drive screw 20 preventing it from backing out. The posterior retainer 19b is snapped around the collar 34 of the housing 12 with the retainer body 144 blocking the posterior drive screw 22 preventing it from backing out.

Figure 13:
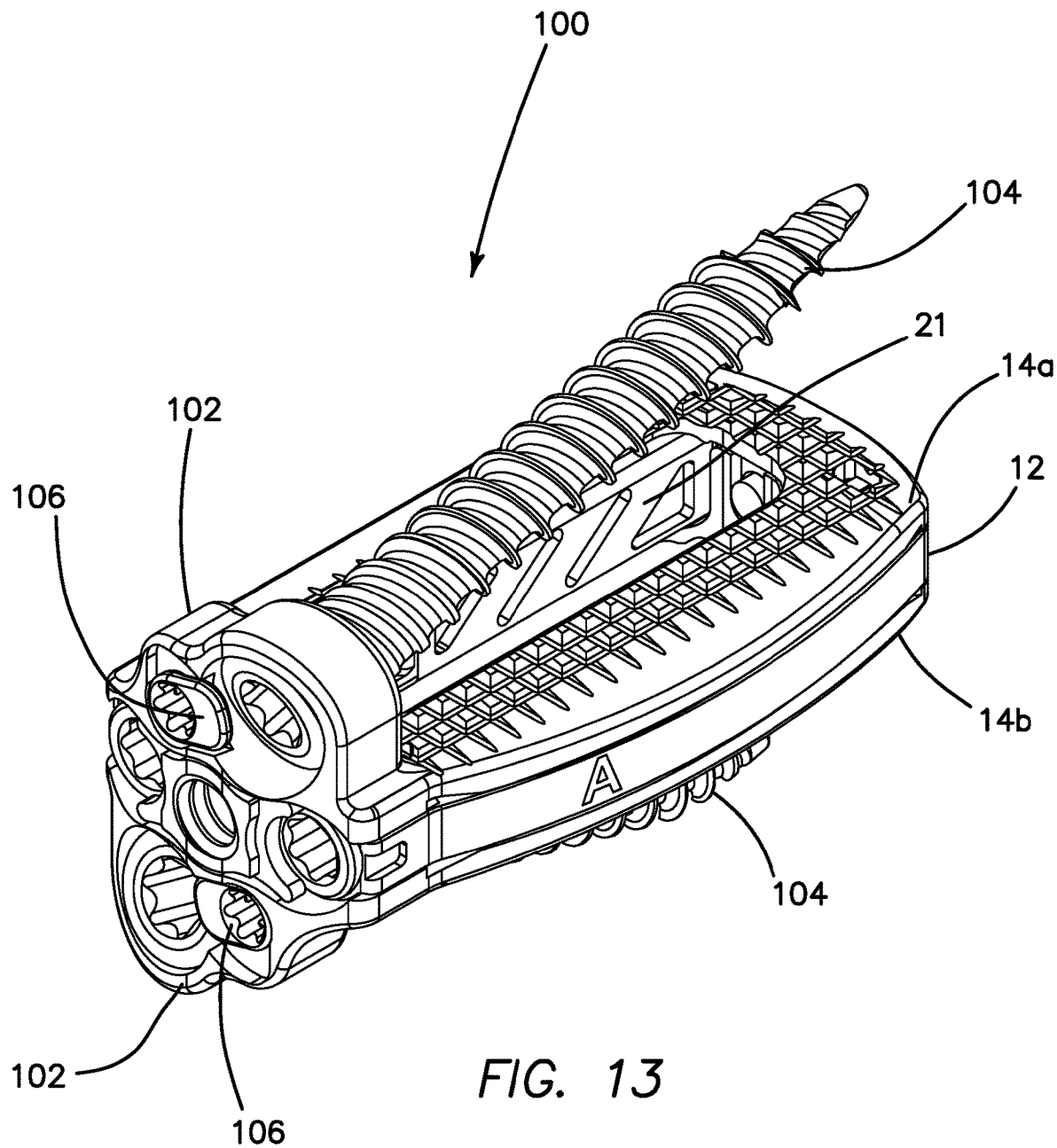
FIG. 13 is a top perspective view of a stand-alone model of an expandable interbody spacer in its low-profile configuration according to the present invention.

Turning now to FIG. 13, there is shown a stand-alone (SA) expandable interbody spacer 100 in a low-profile, collapsed configuration according to the present invention. The stand-alone spacer 100 is identical to the expandable interbody spacer 10 described above with the exception of fixation features integrated into the design. As such, like reference numbers will be used to describe like parts. The fixation features include an expanded/elongated spacer 100 that accommodates a bone screw carriage 102 integrally formed with each of the upper endplate 14a and lower endplate 14b configured to receive and retain a bone screw 104. The carriage 102 further includes an anti-backout system including a bone screw lock 106. Because the stand-alone spacer 100 is longer to accommodate the bone screw carriage 102 while providing the same contact surface on the endplates 14a, 14b compared to the non-SA spacer 10 described above, the actuators 16, 18 and expanders 21 incorporate design changes over the non-SA spacer 10 and will be described hereinbelow.

Figure 14A:
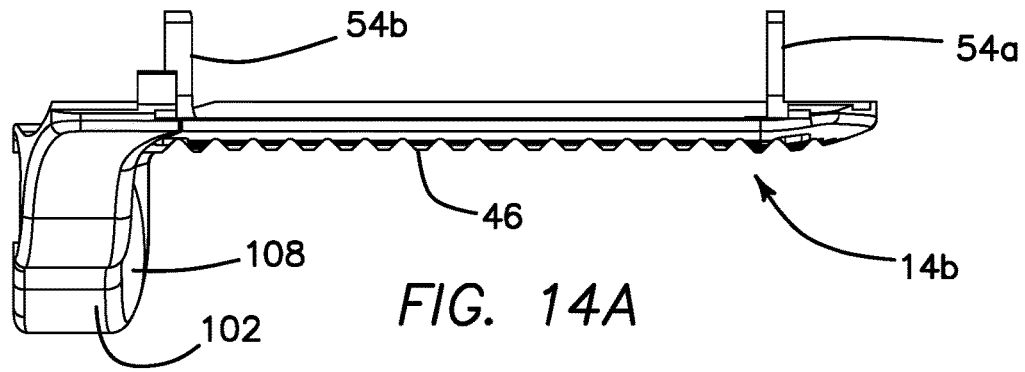
FIG. 14A is a side elevational view of a lower endplate of a stand-alone expandable interbody spacer according to the present invention.
Figure 14B:
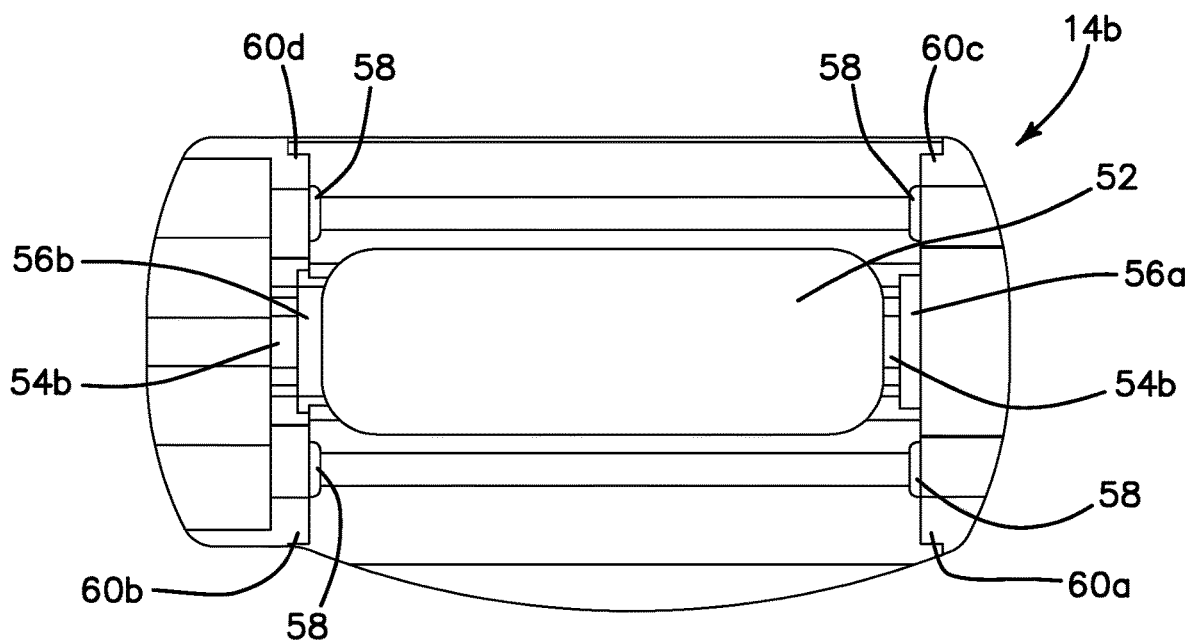
FIG. 14B is a bottom view of the lower endplate of FIG. 14A.
Figure 14C:
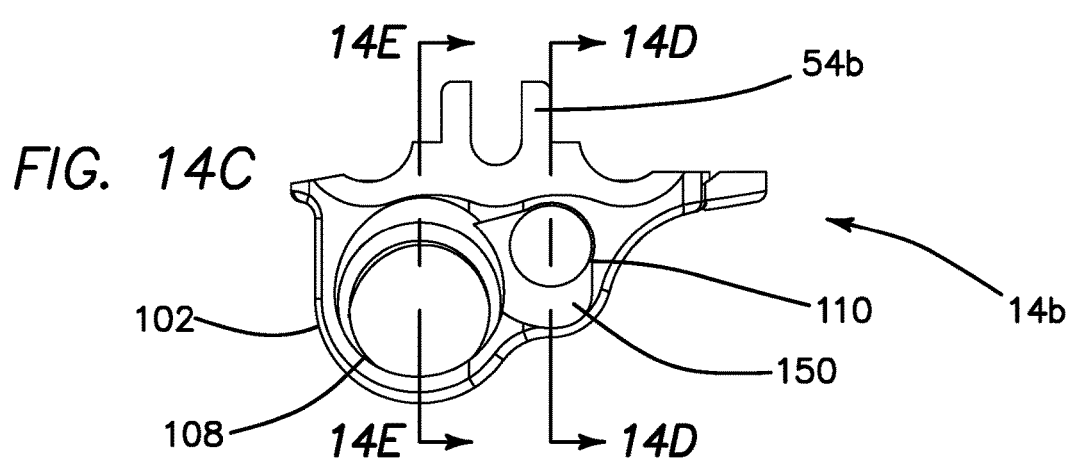
FIG. 14C is a proximal end elevational view of the lower endplate of FIG. 14A.
Figure 14D:
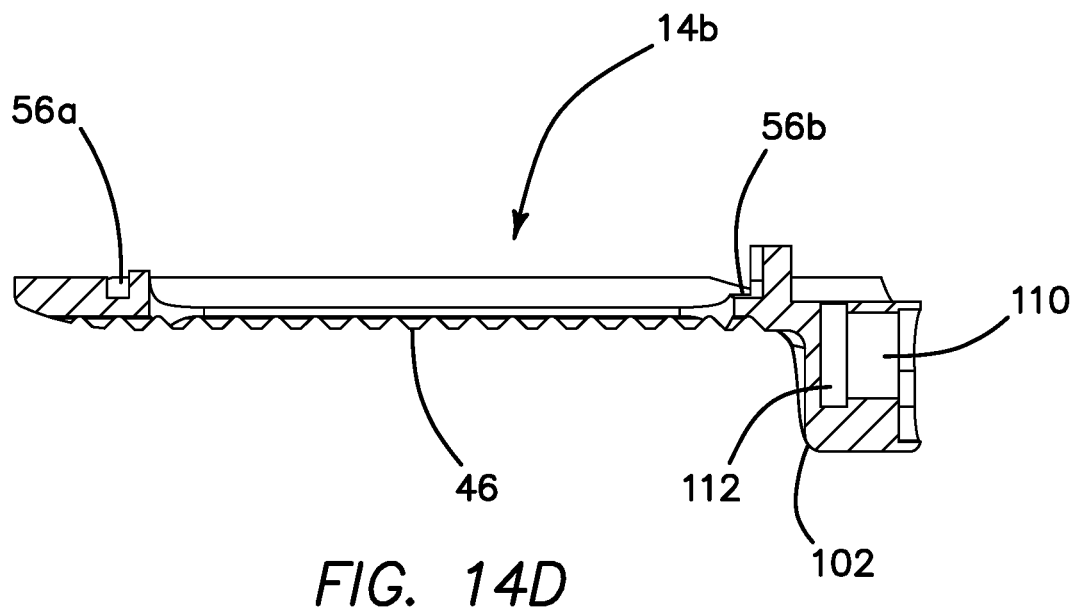
FIG. 14D is a cross-sectional view taken along line 14D-14D of FIG. 14C.
Figure 14E:
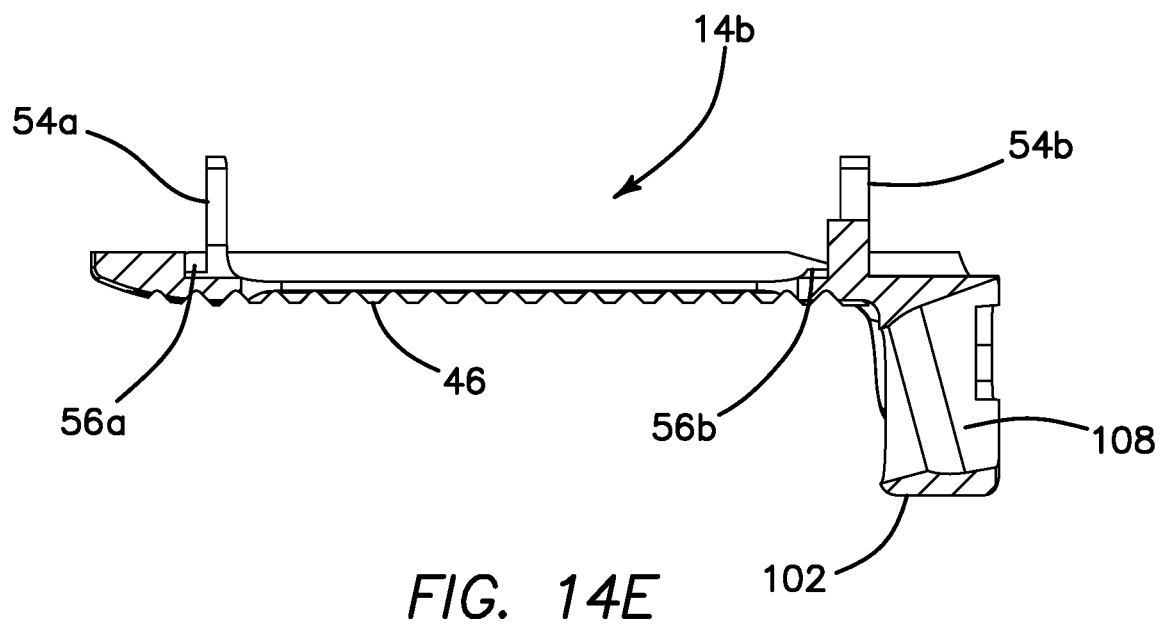
FIG. 14E is a cross-sectional view taken along line 14E-14E of FIG. 14C.

Turning now to FIGS. 14A-14E, the lower endplate 14b will be described in greater detail. The lower endplate 14b includes a bone screw carriage 102 integrally formed at the proximal end of the endplate 14b. The bone screw carriage 102 extends perpendicularly outwardly from the bone engaging surface 46. The carriage 102 includes a bone screw socket 108 and a lock socket 110. The bone screw socket 108 is open at both ends and extends through the carriage 102 from the proximal end to the distal end. The bone screw socket 108 is sized and configured to seat the head of a bone screw 104 such that the bone screw 104 primarily extends through the bone screw socket 108 and distally from the carriage 102 at an angle laterally away from the bone-engaging surface 46 such that the bone screw 104 does not contact and is spaced apart from the upper contact surface 46 of the upper endplate 14a. The socket 108 is configured to permit some polyaxial angulation within the bone screw socket 108 for customized fixation of the bone screw 104 within the vertebrae. The bone screw socket 108 has a smaller distal diameter relative to the proximal diameter in order to allow the larger diameter bone screw head relative to the bone screw shank to polyaxially seat within the socket 108 while preventing the head of the bone screw 104 from passing through the socket 108 and permitting the shank to pass through. The bone screw socket 108 of the lower endplate 14b is near the posterior edge of the lower endplate 14b and is sized and configured to receive a bone screw 104 such that the bone screw 104 does not contact and is spaced apart from the lower contact surface of the lower endplate 14b. The bone screw carriage 102 further includes a lock socket 110 formed laterally, anteriorly adjacent to the bone screw socket 108. The lock socket 110 is sized and configured to receive the bone screw lock 106. The lock socket 110 is open at the proximal end and extends distally to a closed distal end. The distal end of the lock socket 110 forms a larger circumferential diameter well 112, as can be seen in FIG. 14D, relative to the proximal end of the lock socket 110 to accommodate, in snap-fit fashion, the larger diameter distal end of the bone screw lock 106 to secure the lock 106 to the plate 14. A recess 150 is formed around at least part of the perimeter of the proximal opening of the lock socket 110 to accommodate rotation of the lock 106 within the lock socket 110 while still providing a low-profile shape characteristic of a recessed lock 106. The lower endplate 14b of the SA spacer 100 is longer than the non-SA spacer 10. The lower endplate 14b of the SA spacer 100 similarly includes an endplate opening 52 and distal and proximal saddles 54a, 54b for seating the guideposts 28 and distal and proximal saddle receiving locations 56a, 56b for receiving the saddles 54a, 54b of the upper endplate 14b in an adjacent overlapping fashion, small apertures 58, and slots 60a, 60b, 60c, 60d as described above with respect to the non-SA device.

Figure 15A:
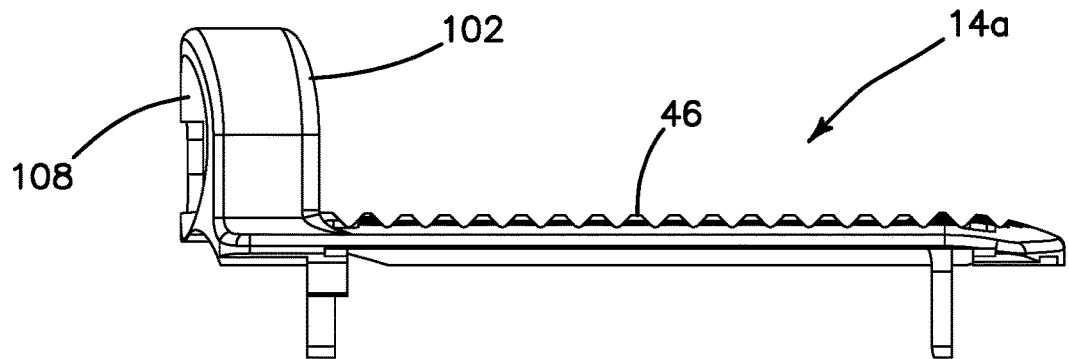
FIG. 15A is a side elevational view of an upper endplate of a stand-alone expandable interbody spacer according to the present invention.
Figure 15B:
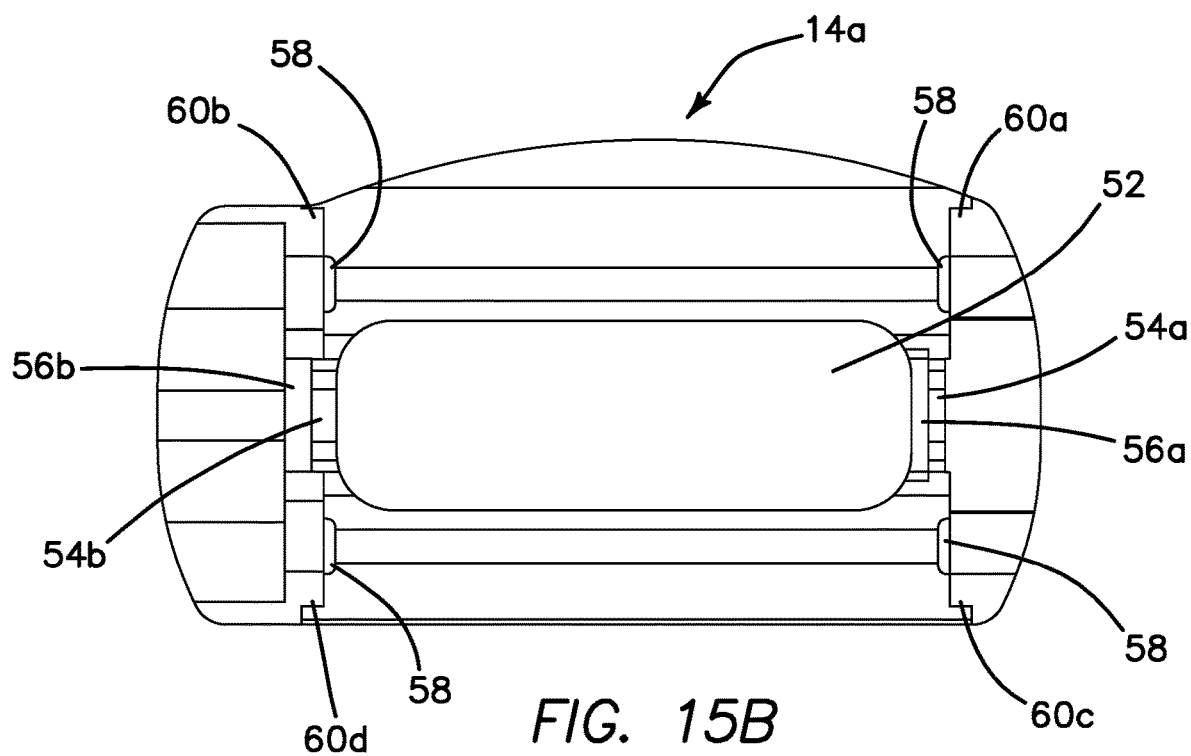
FIG. 15B is a bottom view of the upper endplate of FIG. 15A.
Figure 15C:
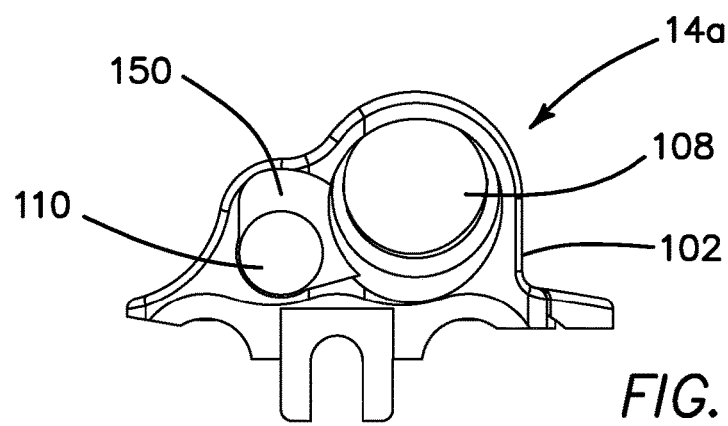
FIG. 15C is a proximal end elevational view of the upper endplate of FIG. 15A.

Turning now to FIGS. 15A-15C, the upper endplate 14a will be described in greater detail. The upper endplate 14a includes a bone screw carriage 102 at the proximal end of the upper endplate 14a. The bone screw carriage 102 extends perpendicularly outwardly from the bone engaging surface 46. The carriage 102 includes a bone screw socket 108 and a lock socket 110. The bone screw socket 108 is open at both ends and extends through the carriage 102 from the proximal end to the distal end. The bone screw socket 108 is sized and configured to seat the head of a bone screw 104 such that the bone screw 104 primarily extends through the bone screw socket 108 and distally from the carriage 102 at an angle laterally away from the bone-engaging surface 46 such that the bone screw 104 does not contact and is spaced apart from the upper contact surface of the upper endplate 14a. The socket 108 is configured to permit some polyaxial angulation within the bone screw socket 108 for customized fixation of the bone screw 104 within the vertebrae. The bone screw socket 108 has a smaller distal diameter relative to the proximal diameter in order to allow the larger diameter bone screw head relative to the bone screw shank to polyaxially seat within the socket 108 while preventing the head of the bone screw 104 from passing through the socket 108 and permitting the shank to pass through. The bone screw socket 108 seats the head of the bone screw in a recessed fashion such that the head does not project proximally from endplate in order to give the implant a low-profile. The bone screw socket 108 is near the anterior edge of the upper endplate 14a. The bone screw carriage 102 further includes a lock socket 110 formed laterally, posteriorly adjacent to the bone screw socket 108. The lock socket 110 is sized and configured to receive the bone screw lock 106. The lock socket 110 is open at the proximal end and extends distally to a closed distal end. The distal end of the lock socket 110 forms a larger circumferential diameter well 112 relative to the proximal end of the socket 110 to accommodate, in snap-fit fashion, the larger diameter distal end of the bone screw lock 106. A recess 150 is formed around at least part of the perimeter of the proximal opening of the lock socket 110 to accommodate rotation of the lock 106 within the lock socket 110. The upper endplate 14a of the SA spacer 100 is longer than the non-SA spacer 10. The upper endplate 14 of the SA spacer 100 similarly includes an endplate opening 52 and distal and proximal saddles 54a, 54b for seating the guideposts 28 and distal and proximal saddle receiving locations 56a, 56b for receiving the saddles 54a, 54b of the lower endplate 14b in an adjacent overlapping fashion, small apertures 58, and slots 60a, 60b, 60c, 60d as described above with respect to the non-SA device.

Figure 16A:
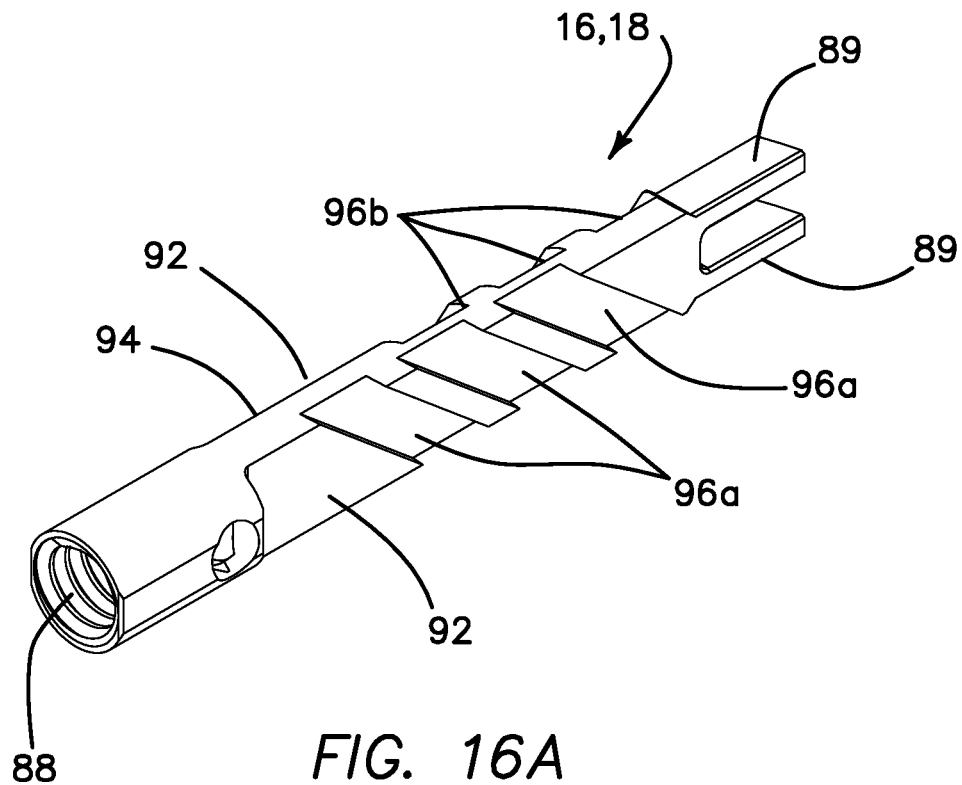
FIG. 16A is a top perspective view of an actuator according to the present invention.
Figure 16B:
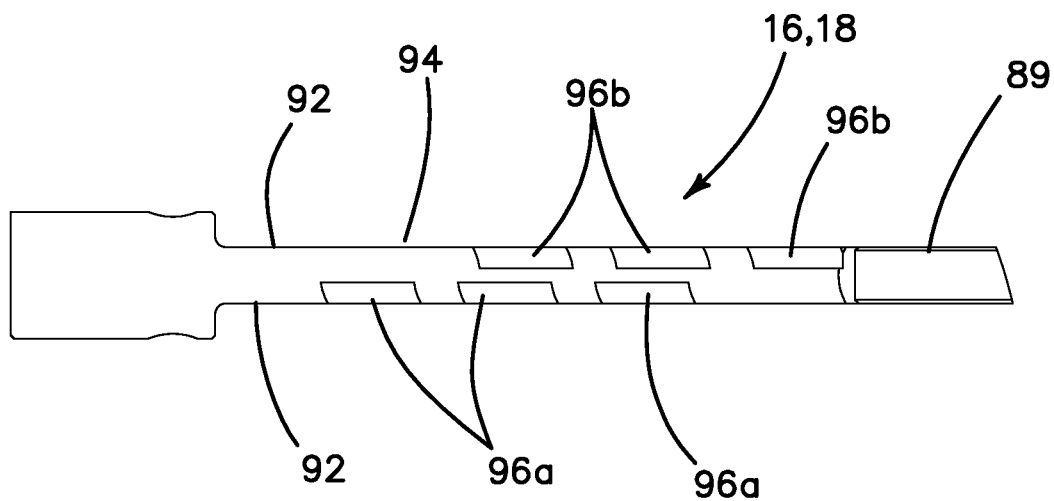
FIG. 16B is a top view of the actuator of FIG. 16A.
Figure 17A:
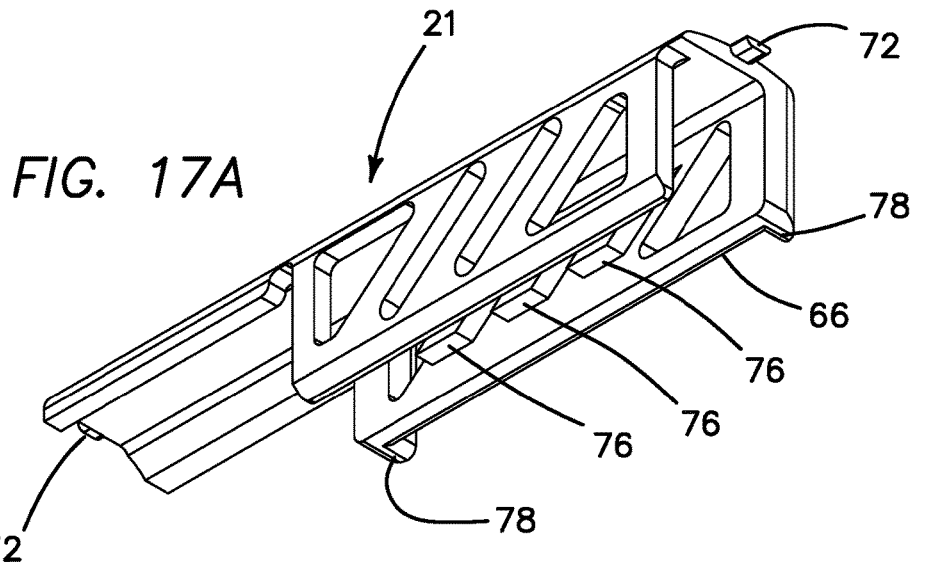
FIG. 17A is a bottom perspective view of an expander according to the present invention.
Figure 17B:
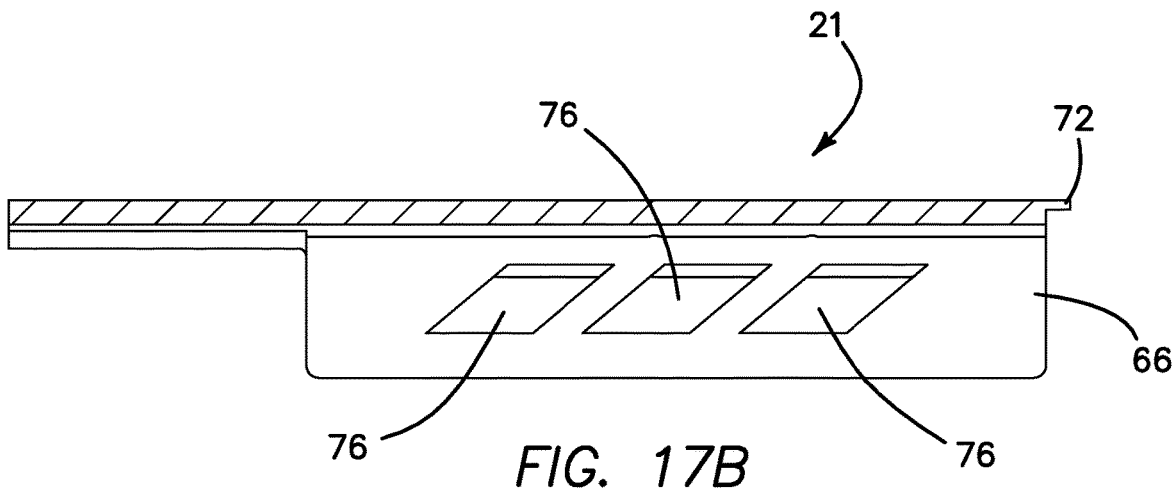
FIG. 17B is a cross-sectional view of the expander of FIG. 17A.
Figure 17C:
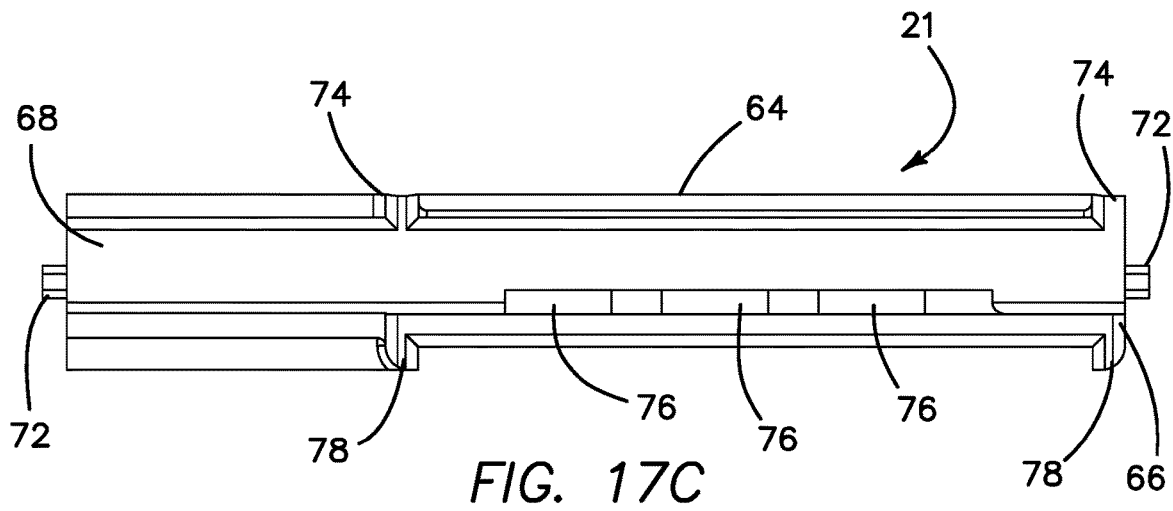
FIG. 17C is a bottom view of the expander of FIG. 17C.

Turning now to FIGS. 16A-16B, the anterior and posterior actuators 16, 18 of the SA spacer 100 will now be described in greater detail. The anterior and posterior actuators 16, 18 are identical to each other and have a proximal bore 88, distal prongs 89, a middle portion 94 with flat sides 92, and grooves 96a formed in anterior side of the actuator 16, 18 and grooves 96b formed in the posterior side of the actuator 16, 18. The actuators 16, 18 of the SA spacer 100 have wider grooves 96 than the non-SA spacer 100 because the SA spacer has longer actuators 16, 18 due to the SA spacer 100 being longer in length along the longitudinal axis. Accordingly, the expanders 21 of SA spacer 100 have correspondingly wider projections 72 formed in the second rail 66 of expander 21 as shown in FIGS. 17A-17C for mating inside the wider grooves 96. Otherwise, the expanders 21 and actuators 16, 18 of the SA device are the same as the non-SA device described above.

Figure 18A:
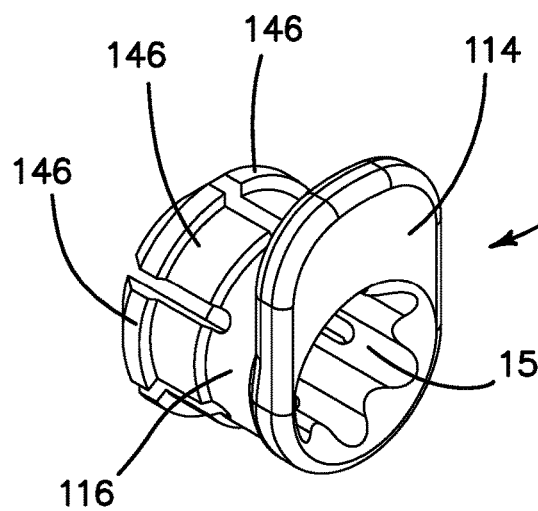
FIG. 18A is a top perspective view of a bone screw lock according to the present invention.
Figure 18B:
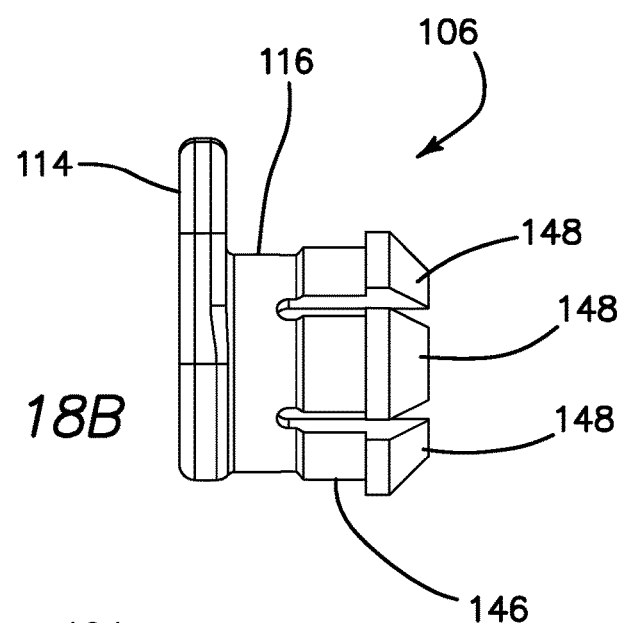
FIG. 18B is a side elevational view of the bone screw lock of FIG. 18A.

Turning now to FIGS. 18A-18B, the bone screw lock 106 will now be described in greater detail. The bone screw lock 106 includes a blocking flange 114 connected to a cylindrical-like post 116. The post 116 extends from the bottom surface 52 of the flange 114 in perpendicular fashion to the flange 114. The post 116 has a diametrically enlarged distal end than include a plurality of circumferentially-arranged flexible fingers 146 having a ramped distal edge 148. The post 116 is configured to be inserted into the lock socket 110 of the endplate 14 such that the fingers 146 are flexed inwardly toward each other before snapping back outwardly to a normal unflexed position when the diametrically enlarged distal edge 148 moves into the well 112 of the lock socket 110 and retained therein. The lock 106 is connected to the endplate 14 such that the lock 106 can rotate relative to the endplate 14 about the longitudinal axis of the post 116.

When the lock 106 is inserted into the lock socket 110, the blocking flange 114 of the lock 106 resides within the lock recess 150 of the endplate 14 adjacent to the bone screw socket 108 and is rotatable between a locked position such that at least part of the blocking flange 114 is above bone screw socket 108 in the pathway of insertion/removal of the bone screw 104 as shown in FIG. 13 and an unlocked position away from the bone screw socket 108 in which insertion/removal of a bone screw 104 is not blocked by the blocking flange 114. The recess 150 prevents the lock 106 from extending proximally beyond the profile of the endplate 14. The lock 106 includes an instrument socket 152 extending from the proximal end of the lock 106 and into the post portion 116. The instrument socket 152 is sized and configured for engaging an instrument having a complementary shaped tip for rotating the lock 106 between an unlocked position and a locked position.

Figure 19:
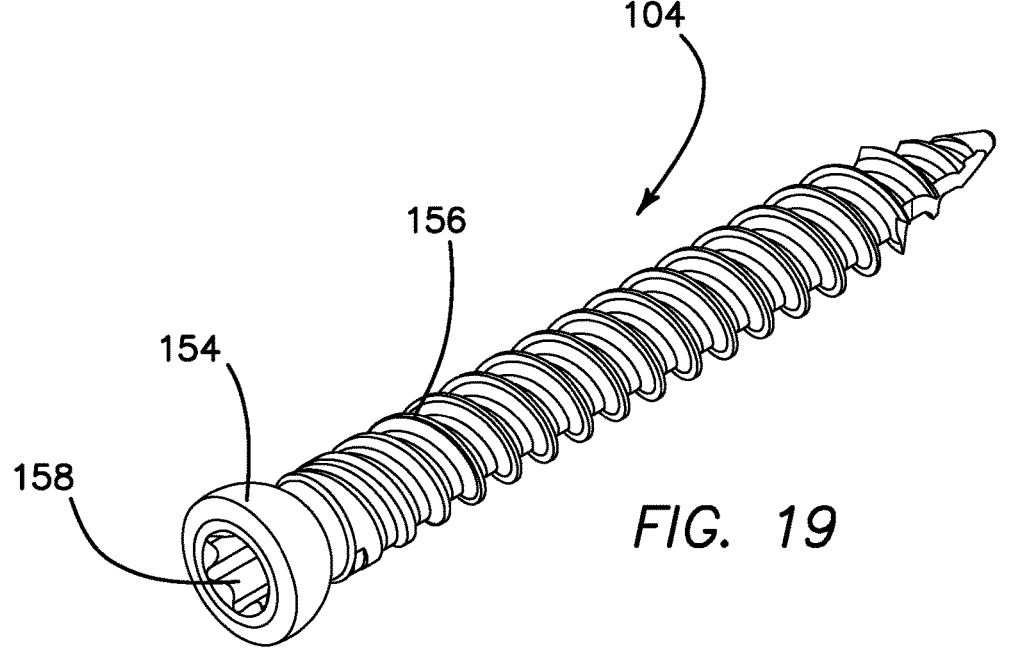
FIG. 19 is a top perspective view of a bone screw according to the present invention.

Turning now to FIG. 19, an exemplary orthopedic fastener or bone screw 104 that is preferably used with the SA expandable spacer 100 of the present invention will now be described. The bone screw 104 includes a screw head 154 and threaded shank 156. The head 40 includes an instrument socket 158 for receiving a complementary tip of a surgical tool. The instrument socket 158 allows a surgical tool to drive the bone screws 104 into the vertebral column. The head 154 of the bone screw 104 corresponds to the shape of the bone screw socket 108 on the housing 12. Various bone screws 104 may be employed including ones capable of poly-axial, variable angle or fixed angled orientation with respect to the endplate 14. The bone screws 104 are preferably self-tapping, however, other screws requiring holes to be drilled or pre-tapped can also be employed with the spacer 100.

The SA expandable interbody spacer 100 is assembled by placing the upper endplate 14a such that the interior surface 48 faces upwardly. One upper expander 21a is connected to the upper endplate 14a by inserting the distal and proximal projections 72 of the expander 21a into the distal and proximal anterior slots 60a, 60b and moving the expander 21a medially into position within the slots 60a, 60b. Another upper expander 21b is connected to the upper endplate 14a by inserting the distal and proximal projections 72 of the expander 21b into the distal and proximal posterior slots 60c, 60d and moving the expander 21b medially into position within the slots 60c, 60d. The lower endplate 14b is oriented such that the interior surface 48 faces upwardly. One lower expander 21c is connected to the lower endplate 14b by inserting the distal and proximal projections 72 of the expander 21c into the distal and proximal anterior slots 60a, 60b and moving the expander 21c medially into position within the slots 60a, 60b. Another lower expander 21d is connected to the lower endplate 14b by inserting the distal and proximal projections 72 of the expander 21d into the distal and proximal posterior slots 60c, 60d and moving the expander 21d medially into position within the slots 60c, 60d. The anterior actuator 16 and the posterior actuator 18 are inserted into through the openings 38 of the housing 12 and the upper and lower expander/endplate subassemblies are inserted into the actuators 16, 18 and housing 12. The distal prongs 89 of the actuators 16, 18 are located in the grooves 36 of the housing 12 and the anterior drive screw 20 is threaded into the anterior actuator 16 and the posterior drive screw 22 is threaded into the posterior actuator 18 connecting the expander/endplate subassemblies to the housing 12. The anterior retainer 19a is snapped around the collar 34 of the housing 12 with the retainer body 144 blocking the anterior drive screw 20 preventing it from backing out. The posterior retainer 19b is snapped around the collar 34 of the housing 12 with the retainer body 144 blocking the posterior drive screw 22 preventing it from backing out. A bone screw lock 106 is inserted into the bone screw socket 108 of each endplate 14a, 14b and connected thereto.

Figure 20:
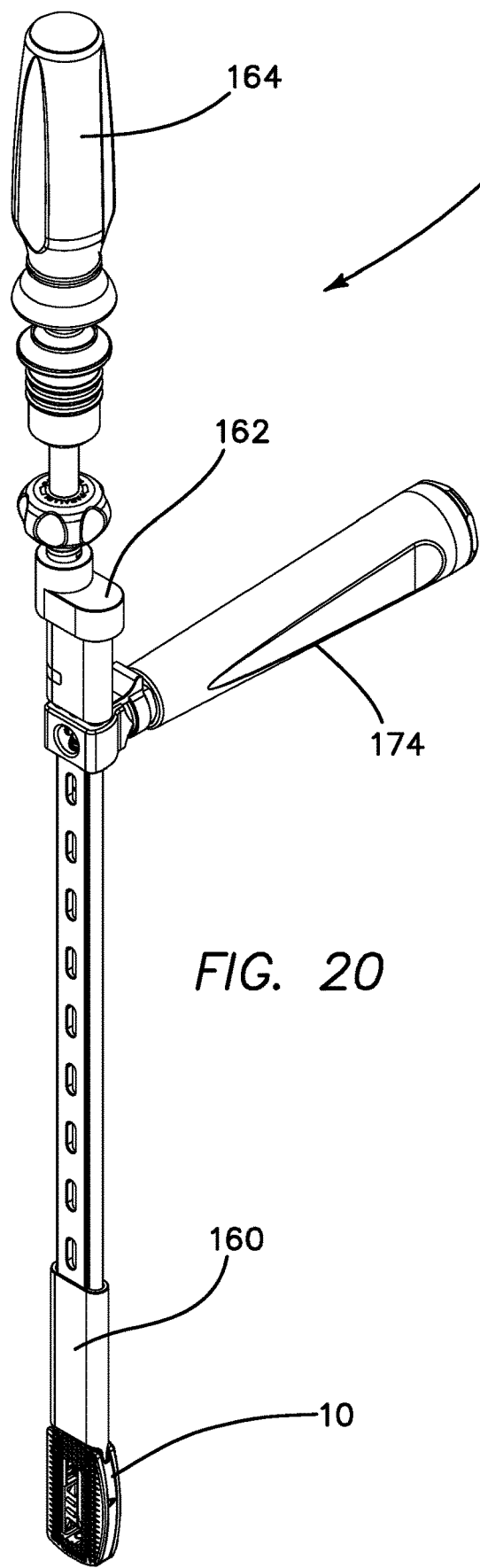
FIG. 20 is a top perspective view of an instrument connected to a spacer according to the present invention.

Turning now to FIG. 20, the instrument 23 will now be described. The instrument 23 includes an inserter 160 connectable to a driver 162. The instrument 23 is shown in FIG. 20 to be connected to the expandable interbody spacer 10; however, the invention is not so limited and the instrument 23 may also be employed with an SA spacer 100 as well.

Figure 21C:
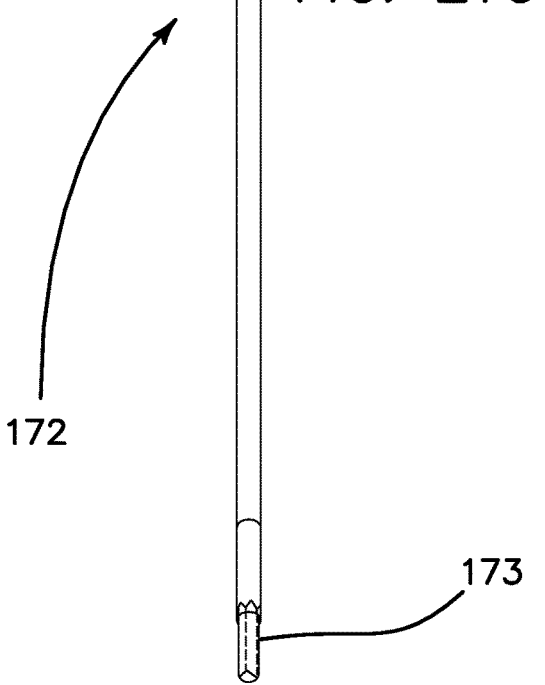
FIG. 21C is a bottom perspective view of an attachment rod according to the present invention.
Figure 21A:
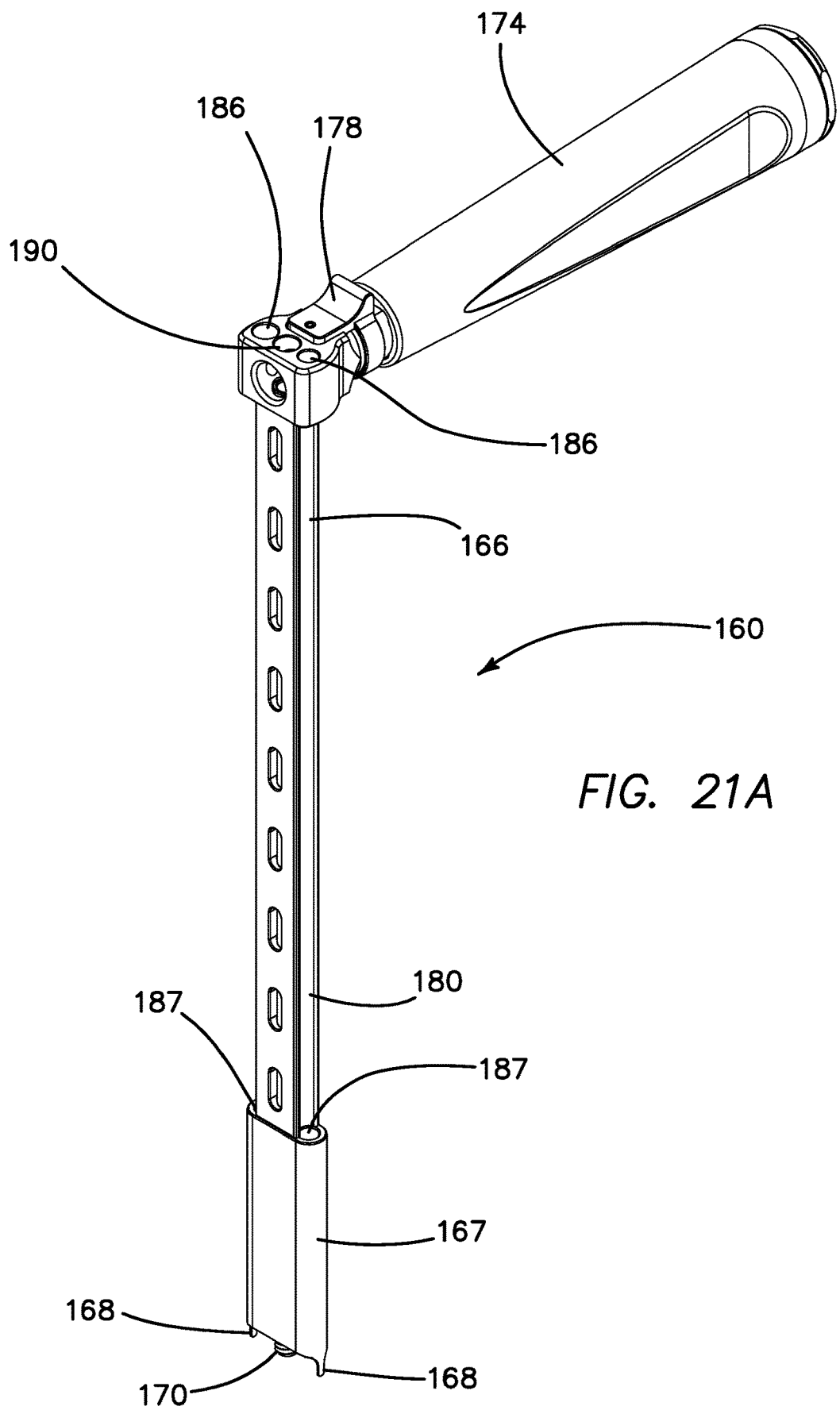
FIG. 21A is a top perspective view of an inserter according to the present invention.
Figure 21B:
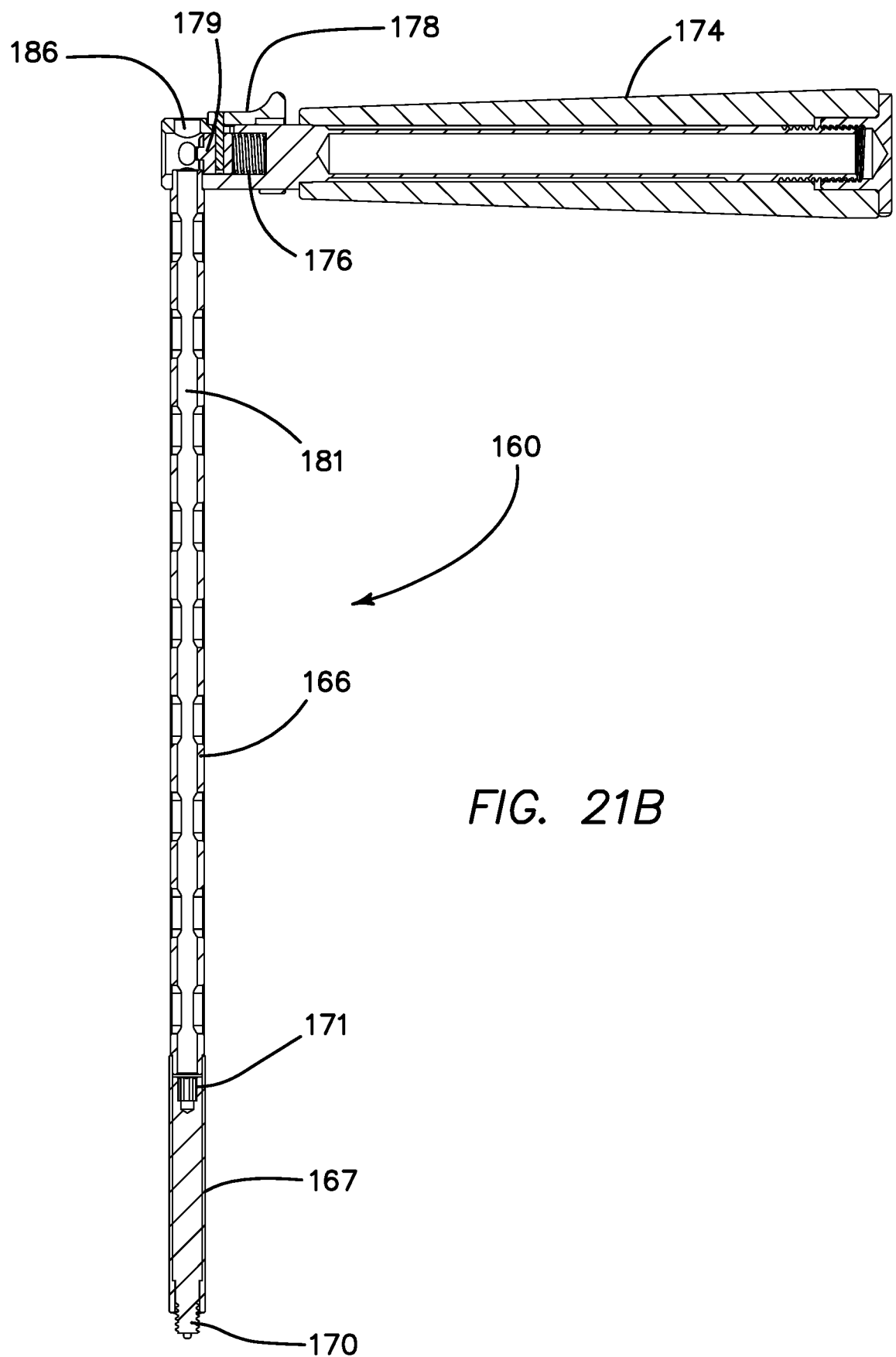
FIG. 21B is a cross-sectional view of the inserter of FIG. 21A according to the present invention.

Turning now to FIGS. 21A-21C, the inserter 160 of the instrument 23 will now be described. The inserter 160 includes a frame 166 extending between a proximal end and a distal end. At the distal end of the frame 166 a distal guide member 167 is provided. The distal guide member 167 includes lateral prongs 168 for engaging the notches 44 on the housing 12. The connection of the lateral prongs 168 to the notches 44 assists in aligning the instrument 23 to the spacer 10, 100 and keeping it stabilized. The distal guide member 167 further includes a central engagement screw 170 having a threaded projection at the distal end for threaded attachment to the rear threaded opening 32 on the housing 12. The proximal end of the elongated central engagement screw 170 includes a hexalobe socket 171 for connecting with a rod 172 having a hexalobe-shaped distal end 173. The rod 172 is shown in FIG. 21C and is used for threading the inserter 160 to the spacer 10, 100. The proximal end of the rod 172 is configured to serve as a handle and/or configured to connect with a handle. The rod 172 further includes a circumferential neck 175 of reduced diameter near the proximal end of the rod 172. The frame 166 includes a central channel 181 for receiving the rod 172 and two concave side channels 180 extending from the proximal end and the distal end of the frame and sized and configured to receive the cylindrical anterior rod 182 and the cylindrical posterior rod 184 of the driver 162 and to guide them into corresponding guide bores 187 in the distal guide member 167. The handle system 174 also includes proximal guide bores 186 for guiding the anterior and posterior rods 182, 184 into the channels 180 and into the distal guide bores 187 and a proximal central guide bore 190 for guiding the attachment rod 172 into the frame 166 and into the socket 171.

Still referencing FIGS. 21A-21C, the inserter 160 includes a handle 174 connectable to the proximal end of the frame 166. The handle 172 includes a spring 176 configured to bias a thumb slider 178 that is movably connected around the handle 172 and pinned to a bit 179 that is sized and configured to engage the neck 175 of the rod 172 and also to engage the driver 162 as will be explained in greater detail below. When the rod 172 or driver 162 is inserted into the central guide bore 190 of the inserter 160, the bit 179 will be deflected away from the longitudinal axis of the inserter 160. With further distal insertion of the inserter 160 and when the bit 179 is aligned with the neck 175 of the rod 172 or inserter 160, the bit 179 will spring into a locking position inside the circumferential groove of the neck 175 to lock the rod 172 or driver 162 to the inserter 160. Moving the thumb slider 178 in a direction away from the longitudinal axis of the inserter 160, moves the bit 176 out of the engagement of the neck 175 to unlock the rod 172 or driver 162 to free it for removal from the inserter 160 in the proximal direction.

Figure 22A:
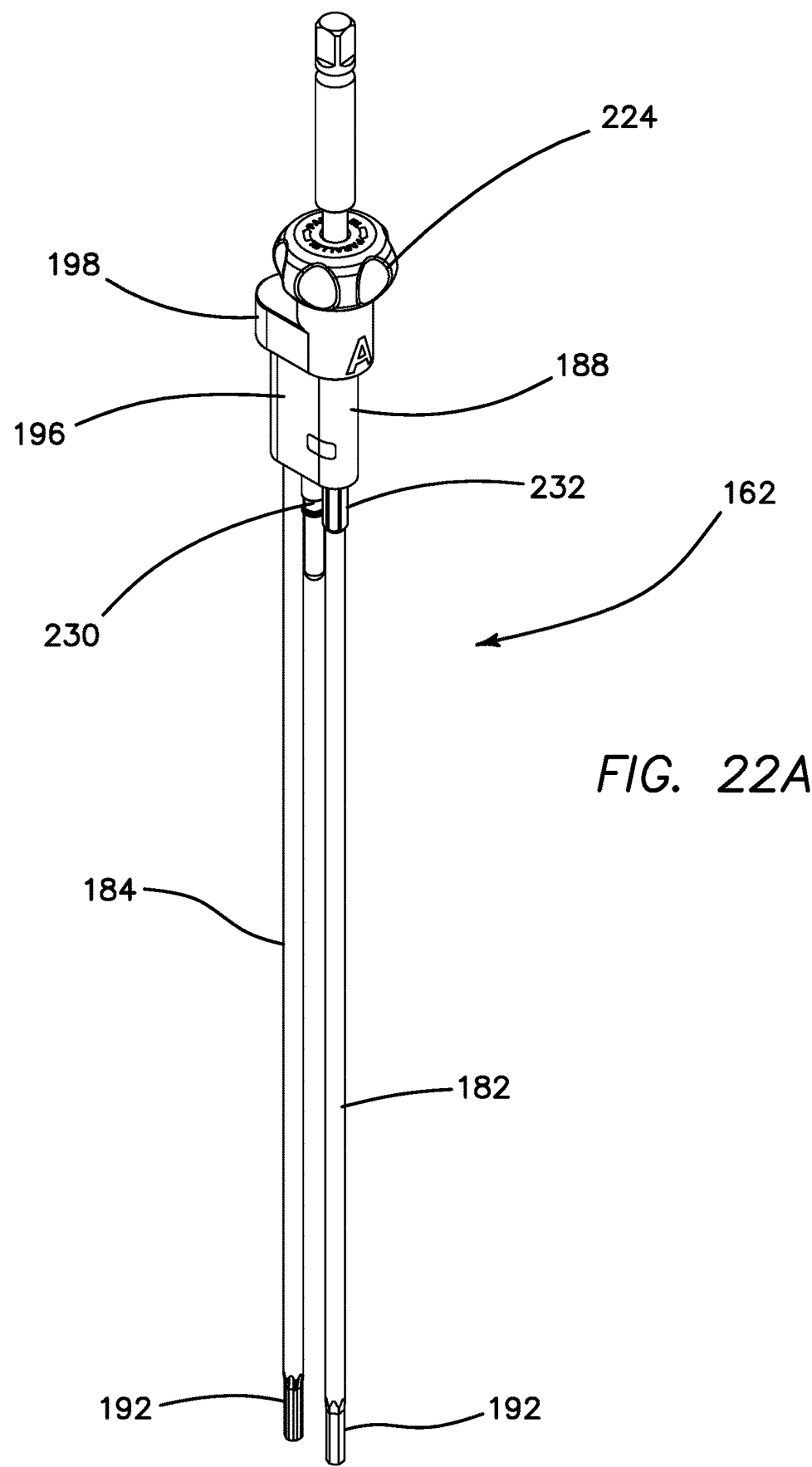
FIG. 22A is a top perspective view of a driver according to the present invention.
Figure 23A:
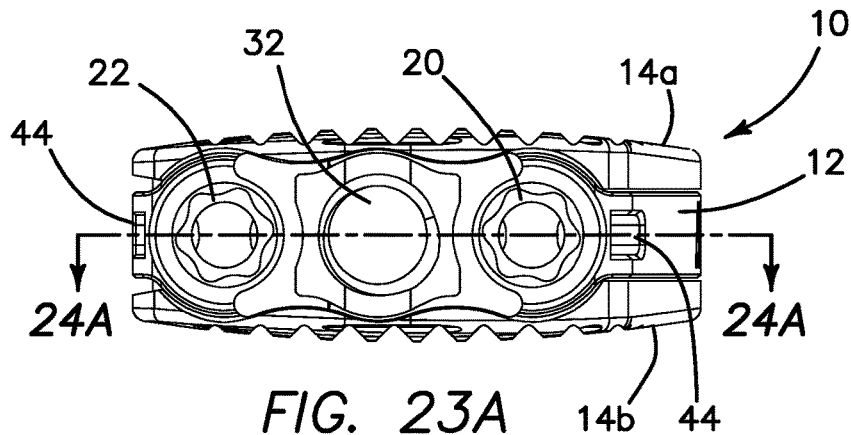
FIG. 23A is a proximal end elevational view of an expandable interbody spacer in a low-profile, unexpanded configuration according to the present invention.
Figure 23B:
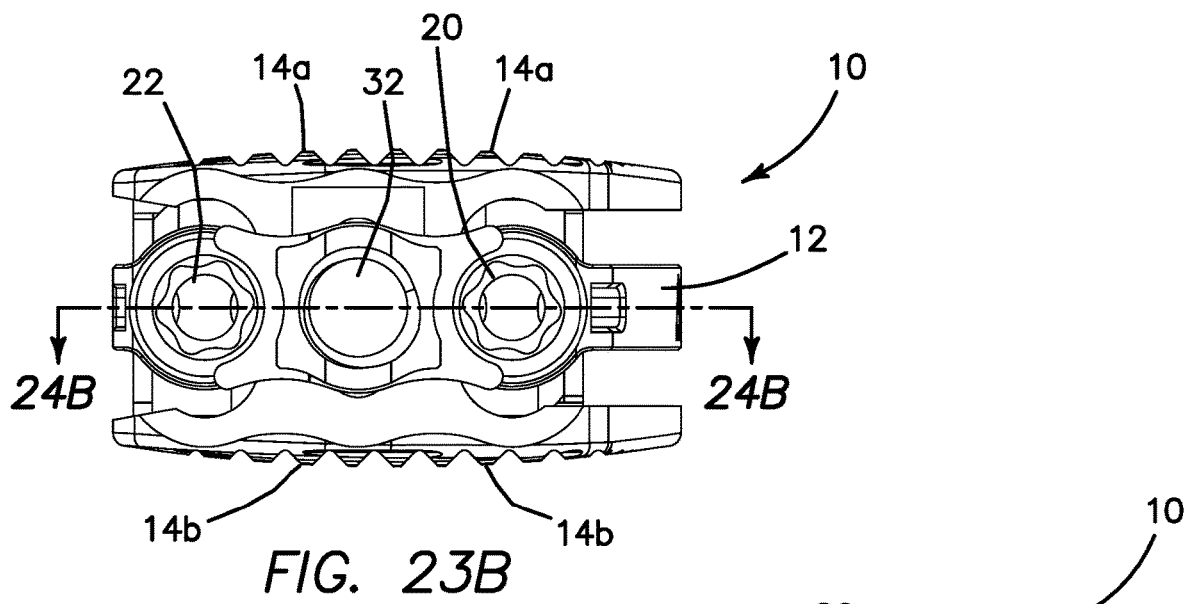
FIG. 23B is a proximal end elevational view of an expandable interbody spacer in parallel expansion according to the present invention.
Figure 23C:
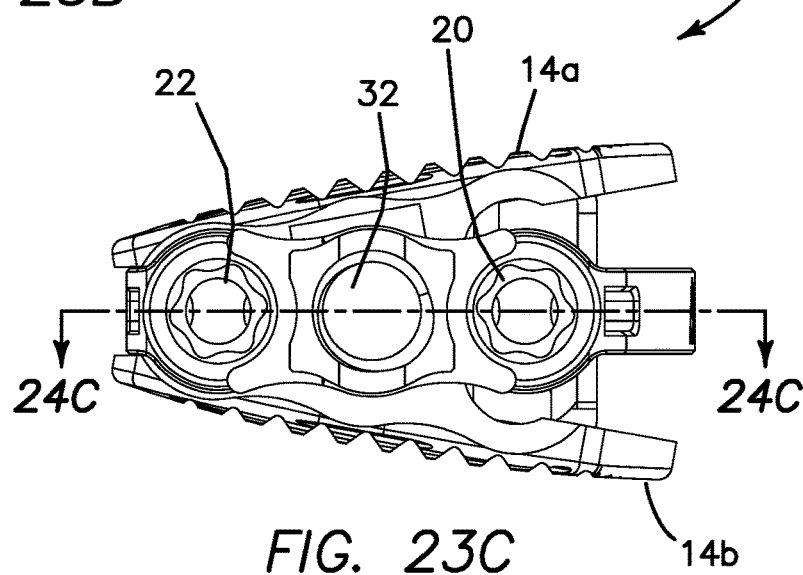
FIG. 23C is a proximal end elevational view of an expandable interbody spacer in anterior-only expansion/angulation according to the present invention.
Figure 24A:
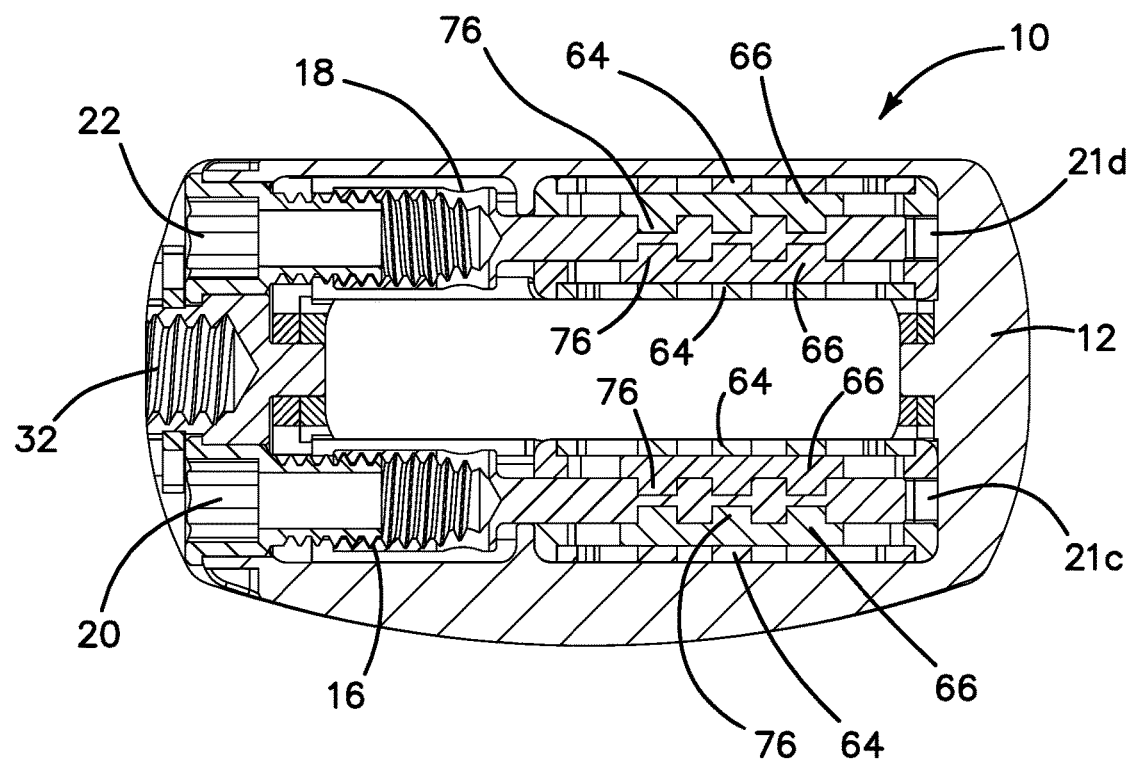
FIG. 24A is a cross-sectional view taken along line 24A-24A of FIG. 23A.
Figure 24B:
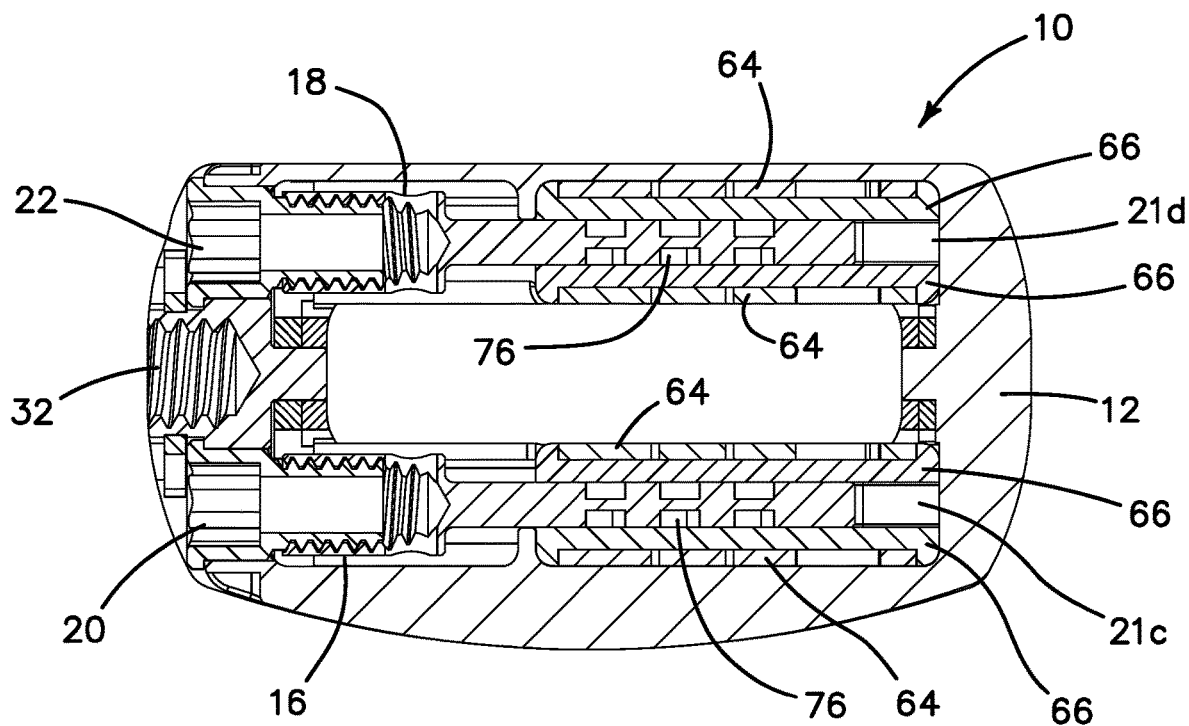
FIG. 24B is a cross-sectional view taken along line 24B-24B of FIG. 23B.
Figure 24C:
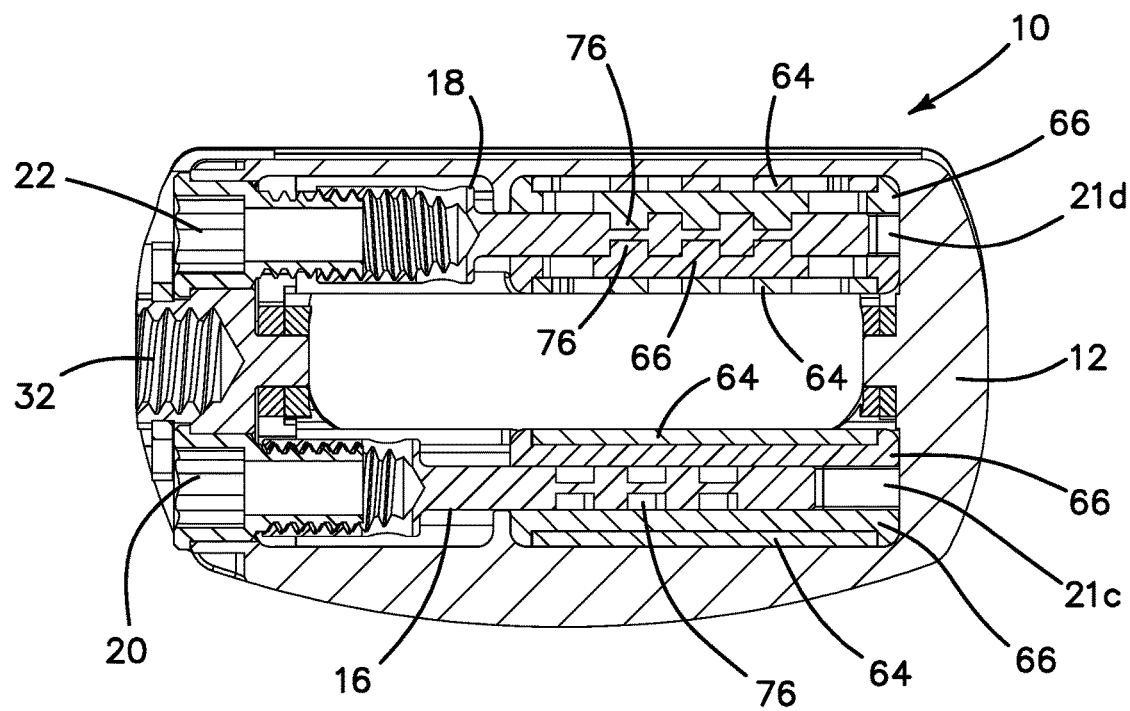
FIG. 24C is a cross-sectional view taken along line 24C-24C of FIG. 23C
Figure 26A:
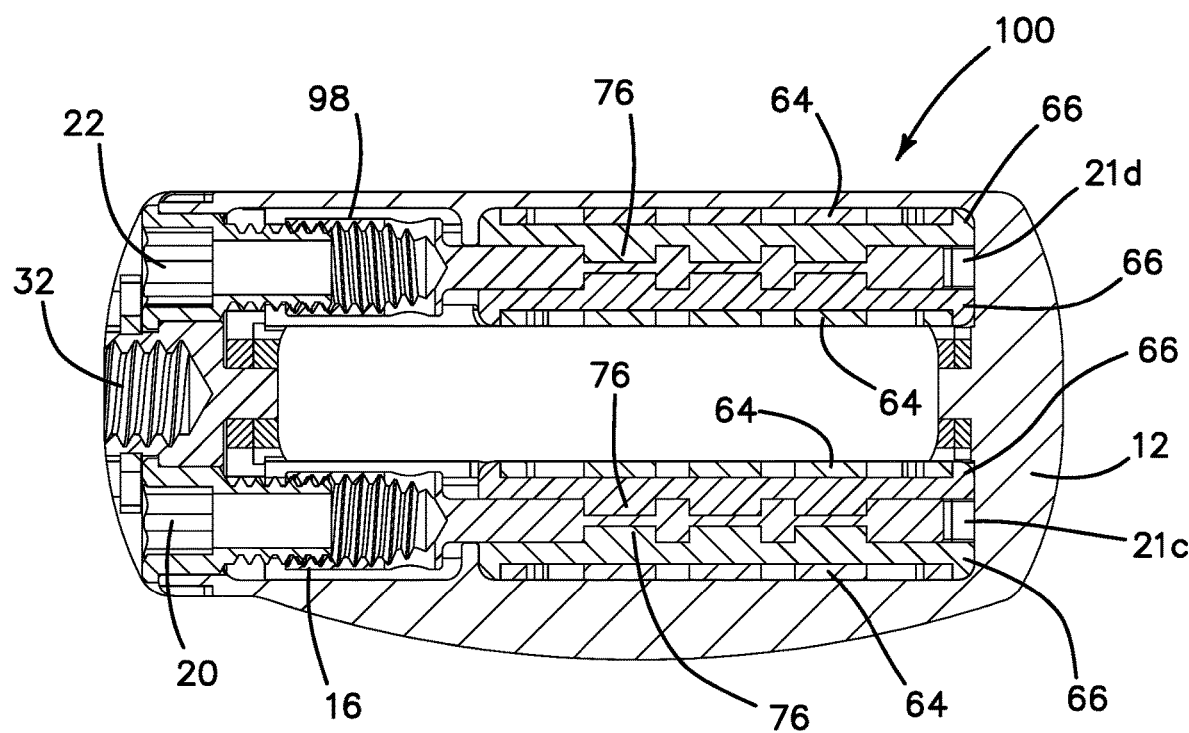
FIG. 26A is a cross-sectional view taken along line 26A-26A of FIG. 25A.
Figure 25C:
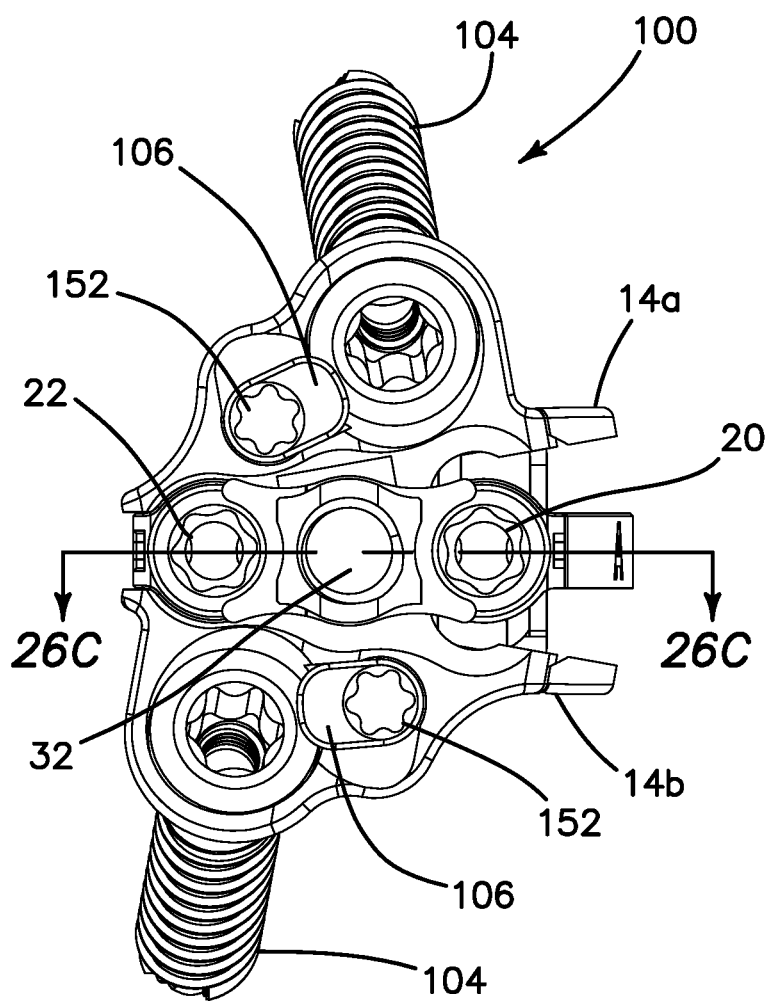
FIG. 25C is a proximal end elevational view of a stand-alone expandable interbody spacer in anterior-only expansion/angulation according to the present invention.
Figure 26B:
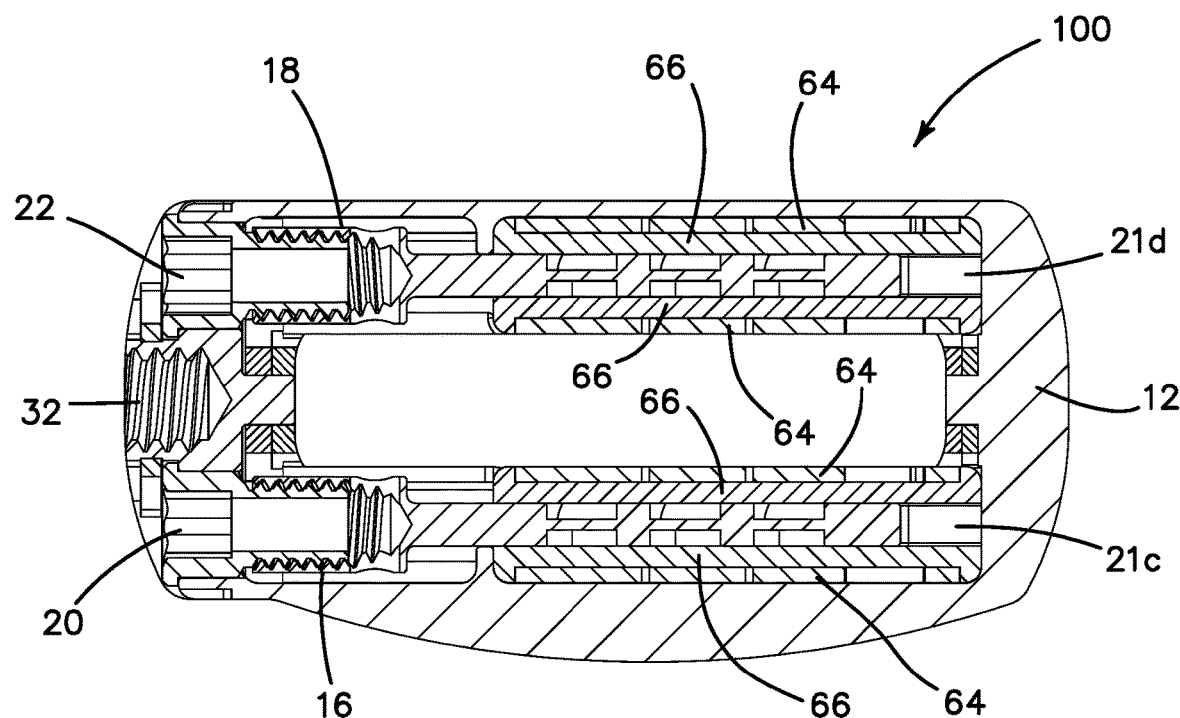
FIG. 26B is a cross-sectional view taken along line 26B-26B of FIG. 25B.
Figure 26C:
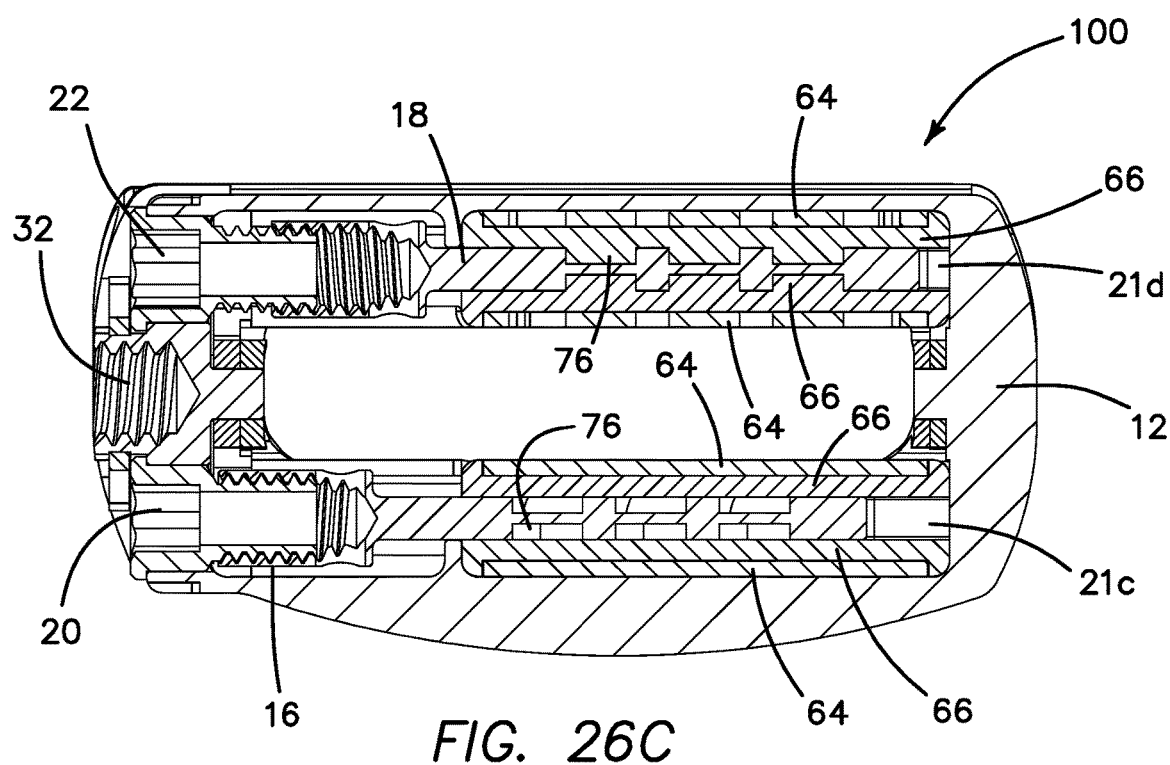
FIG. 26C is a cross-sectional view taken along line 26C-26C of FIG. 25C.
Figure 27:
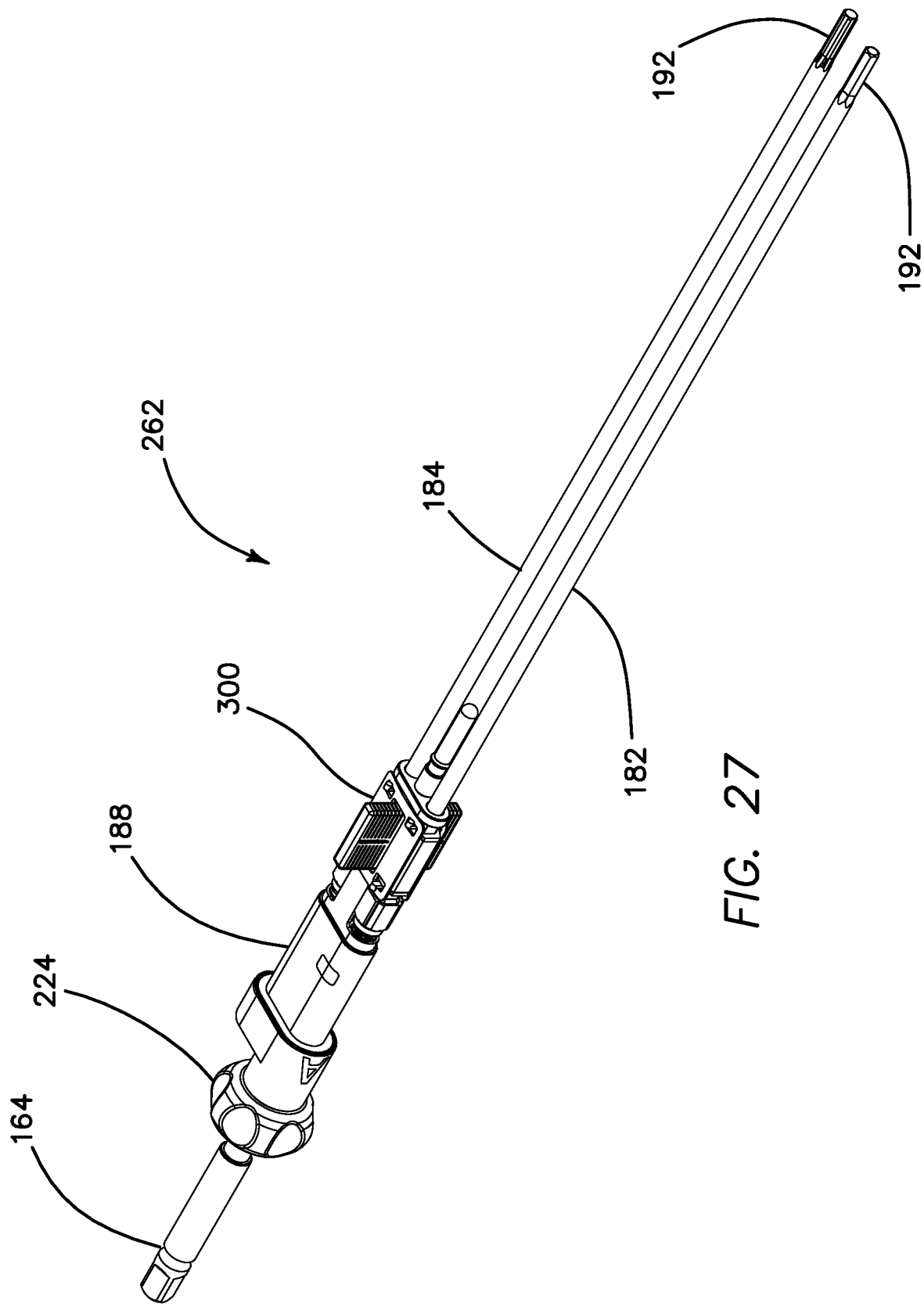
FIG. 27 is a top perspective view of a driver with a gauge according to the present invention.

Turning now to FIG. 22A-22C, the instrument driver 162 will now be described. The driver 162 includes an anterior rod 182 and a posterior rod 184. The anterior rod 182 is longer than the posterior rod 184 and extends proximally to a proximal end where the anterior rod 182 is configured to serve as a handle and/or configured to connect with a handle 164 as shown in FIG. 20. The distal end of the both the anterior rod 182 and posterior rod 184 has a tip 192 with a cross-section sized and configured to engage the drive bores 124 of the drive screws 20, 22. The distal ends 192 are aligned to engage with both the anterior drive screw 16 and posterior drive screw 18 simultaneously. The driver 162 further includes a housing 188 comprising a lower 196 housing connected to an upper housing 198. The anterior rod 182 extends proximally from the housing 188 while the posterior rod 184 does not. The anterior rod 182 and the posterior rod 184 are parallel and spaced apart from each other. The upper housing 198 includes an externally threaded post 200 that is concentric with the anterior rod 182. The housing 188 defines an interior anterior gear chamber 202, a spring chamber 204, and a lock chamber 206 and an anterior rod channel 208 concentric about the anterior rod 182 and extending from a proximal opening in the upper housing 198 to a distal opening in the lower housing 196. The housing 188 further defines an interior posterior gear chamber 210 and an interior posterior rod channel 212 concentric about the posterior rod 184. The posterior rod channel 212 extends from the posterior gear chamber 210 to a distal opening in the lower housing 196.

Figure 33:
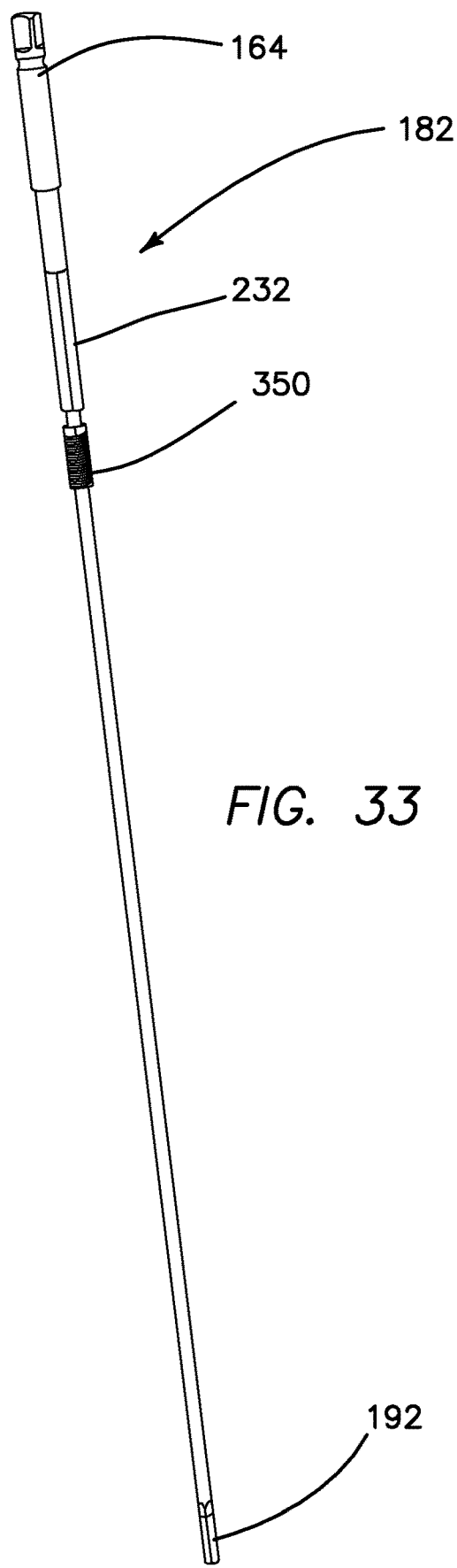
FIG. 33 is a top perspective view of an anterior rod according to the present invention.
Figure 34:
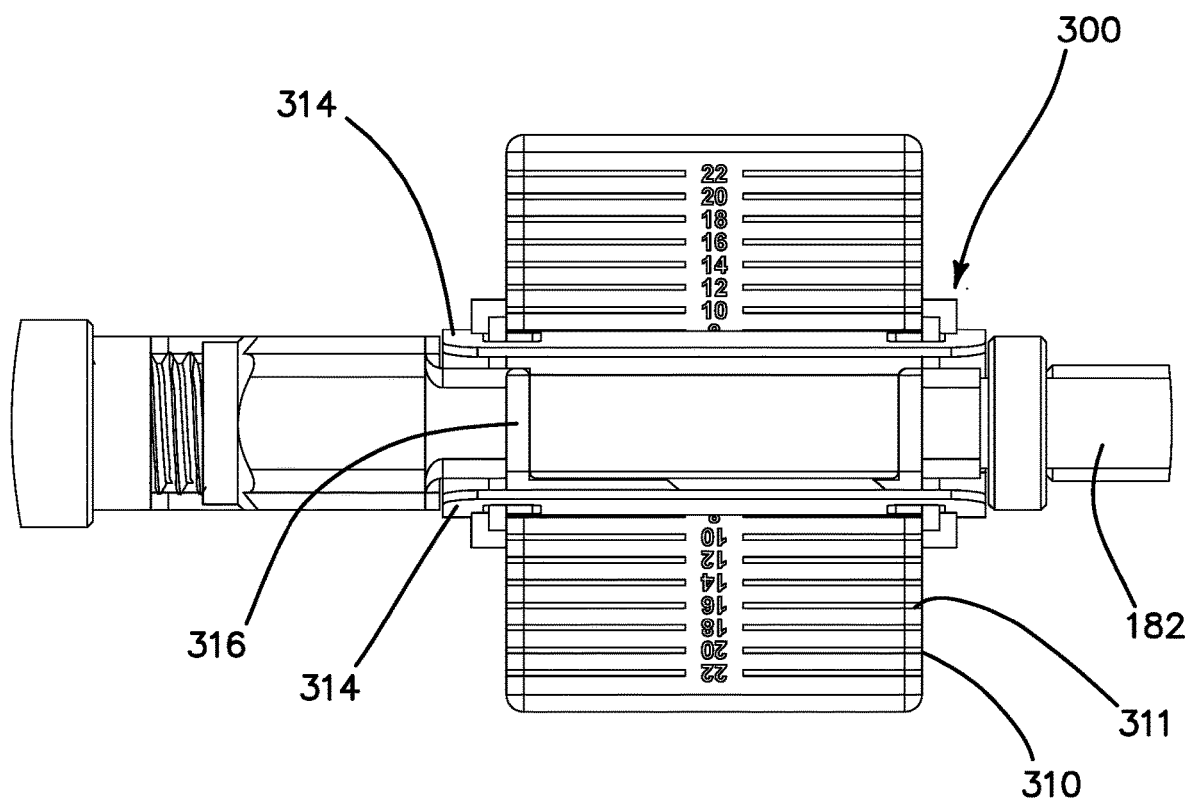
FIG. 34 is a sectional view of a driver with a gauge according to the present invention.

A posterior gear 194 is fixedly connected to the proximal end of the posterior rod 184. The posterior gear 194 gear resides inside the posterior gear chamber 210 and extends into the anterior gear chamber 202. The posterior gear 194 and posterior rod 184 can rotate with respect to the housing 188. An anterior gear 214 is provided with a central opening having a non-circular cross-sectional shape such as a hex-alobe, hexagon, square or other shape through which the anterior rod 182 is inserted. As can be seen in FIGS. 22A and 33, the anterior rod 182 includes a gear-engaging portion 232 along its longitudinal axis that has a cross-sectional shape that corresponds to the cross-sectional shape of the central opening on the anterior gear 214 so as to be capable of engaging the anterior gear 214 for rotation. The anterior gear 214 rotates together with respect to the anterior rod 182 when it is engaged with the gear-engaging portion 232. The anterior gear 214 is not restrained along the longitudinal axis and is movable with respect to the anterior rod 182. The anterior gear 214 resides inside the anterior gear chamber 200 and extends into the posterior gear chamber 210 such that the teeth of the anterior gear 214 is capable of engaging the teeth of the posterior gear 194 when aligned in the same plane perpendicular to the longitudinal axis of the driver 162. A spring 216 is located inside the spring chamber 214 and configured to bias the anterior gear 214 and move the gear 214 toward the proximal end of the anterior gear chamber 202 as shown in FIG. 22B. A two-piece lock 220 is located inside the lock chamber 206 and connected therein with respect to lower housing 196. The lock 220 encompasses the anterior rod 182 in a lock-receiving location 222 of reduced diameter along the anterior rod 182. The lock 220 is configured to prevent the anterior rod 182 from moving longitudinally with respect to the housing 188. A cylindrical actuator or knob 224 having a threaded central bore extending from a proximal opening to a relatively larger distal opening is configured to threadingly engage externally threaded post 200 of the upper housing 198. The central bore includes an inner circumferential ledge 226 creating a reduced diametrical opening at the proximal end of the actuator 224 compared to the distal opening of the central bore. A cylindrical collar 218 that is coaxial with the anterior rod 182 is placed around the anterior rod 182 and seated against the ledge 226 and connected to the actuator 224 such that the actuator 224 can move the collar 218 in a distal direction along the longitudinal axis of the anterior rod 182. The driver 162 further includes a locking rod 228 located between the anterior rod 182 and the posterior rod 184 and extending distally from lower housing 198 in parallel fashion to the anterior and posterior rods 182, 184. The locking rod 228 includes a neck portion 230 having a reduced diameter sized to engage with and be captured by the thumb release/lock bit 179 of the inserter handle 174 to connect the driver 162 to the inserter 160. FIG. 20 shows the handle 164 of the driver 162 to be a torque limiting handle connected to the proximal end of the anterior rod 182. The torque limiting handle is configured to prevent too much force from being applied to the anterior rod 182 as well as inform the user if not enough force has been applied.

In use, the present expandable interbody spacer 10, 100 is inserted into the disc space between adjacent vertebral bodies. The spacers 10 of FIGS. 1-29 are generally configured for use as a TLIF cage in spinal surgical procedures. It is understood that novel features of the present invention can find application in different types of spacers including but not limited to interbody spacers for ALIF, PLIF, TLIF, XLIF surgical procedures as well as other types of orthopedic implants.

Implanting the interbody spacer 10, 100 involves removal, in whole or in part, of the disc material from the intervertebral space at the target vertebral level where the interbody spacer 10, 100 will be implanted. The patient is oriented to provide some distraction of the disc space and to provide access to the spine. Additional distraction of the disc space and surrounding tissues may be needed to decompress the nerve roots, realign the anatomical axis of the spine, and restore disc space height at the particular target level. After disc material is removed, a clean space is achieved in which to place the device. The vertebral endplates may be further prepared using burrs, curettes and the like to abrade and clean the endplates to encourage bone regeneration.

A user will connect the spacer 10, 100 to the instrument 23. In particular, the user will align the prongs 168 on the inserter 160 with notches 44 on the spacer 10, 100. The rod 172 is inserted into the proximal guide bore 186 of the inserter 160 until the distal end 173 of the rod 172 engages the proximal end of the distal guide member 167. The distal end 173 of the rod 172 is threaded to connect with the threaded socket 171 of the distal guide member 167. The rod 172 is inserted until the neck 175 of the rod 172 clicks with the bit 179 of the thumb slider 178 and is, thereby, locked in position. The rod 172 is rotated about its longitudinal axis to thread the engagement screw 170 at the distal end of the guide member 167 into the rear threaded opening 32 of the housing 12 of the spacer 10, 100. After the inserter 160 is connected to the spacer 10, 100, the thumb slider 178 is pulled back by the user to disengage the bit 179 from the neck 175 of the rod 172 to free the rod 172 for removal in the proximal direction. After the rod 172 is removed from the inserter 160, the driver 162 is inserted into the inserter 160 by aligning the anterior rod 182 and posterior rod 184 with the proximal guide bores 186 on the inserter 160 and sliding the anterior and posterior rods 182, 184 into their respective side channels 180 on the inserter and into their respective guide bores 187 in the distal guide member 167. The tips 192 of the anterior and posterior rods 182, 184 will be positioned and aligned with the bores 88 of both the anterior actuator 16 and posterior actuator 18. The inserter 162 is inserted until the neck portion 230 of the locking rod 228 clicks past the spring-biased bit 179 to lock and prevent proximal removal of the driver 162 from the inserter 160.

The surgeon uses the instrument 23 to move the spacer 10, 100 and place it at the mouth of the intervertebral space in its low-profile configuration. The spacer 10, 100 is moved and orientated into its proper location within the intervertebral space. Bone graft or other material may be placed inside the interior of the spacer 10, 100 through the endplate openings 52 prior the insertion of the spacer 10, 100 into the disc space. The bone graft material promotes ingrowth and improves blood supply in order to grow active and live bone from the adjacent spinal vertebrae to inter-knit with the spacer 10, 100 and, thereby, eventually immobilize and fuse the adjunct spinal vertebrae. The spacer 10, 100 is placed such that the upper endplate 14a contacts the lower endplate of the upper vertebral body and the lower endplate 14b of the spacer 10, 100 contacts the upper endplate of the lower vertebral body on either side of the target intervertebral space. The geometry of the teeth on the bone-engaging surface 46 provides resistance to migration of the spacer 10, 100 while inside the target space. Other coatings and surface textures may also be provided on the spacer 10, 100. When the spacer 10, 100 is in position, the user decides the best deployment of the spacer 10, 100 from its low-profile configuration for the given patient anatomy. The user may select uniform parallel expansion in which the both the upper endplate 14a and lower endplate 14b are expanded away from each other in a uniform fashion such that the upper endplate 14a and lower endplate 14b remain parallel yet the distance between them is increased uniformly on both the upper and lower sides of the spacer 10, 100. The user may select angular expansion in which only the anterior side of the spacer 10, 100 on both the upper and lower sides of the spacer 10, 100 is expanded to increase the distance between the upper endplate 14a and the lower endplate 14b while the distance between the upper and lower endplates 14a, 14b along the posterior side of the spacer 10, 100 is not increased, thus angulating the spacer 10, 100 such that the endplates 14a, 14b angulate into expansion with only anterior side increasing in height into expansion. The degree of angular or uniform expansion may be varied as need and the user need not max out the expansion. The user may also return the spacer expansion toward the unexpanded state by any degree by incremental rotation of the instrument 23 to fine tune the expansion as needed.

FIGS. 23A, 24A, 25A and 26A show the spacer 10, 100 in a low-profile, unexpanded configuration. It is in this low-profile configuration that the spacer 10, 100 is inserted into the disc space with the instrument 23 connected to the spacer 10, 100 as shown in FIG. 20. To effect a condition of uniform parallel expansion of the spacer 10, 100, which is shown in FIGS. 23B, 24B, 25B and 26B, the user will rotate the actuator 224 on the driver 162 in a clockwise direction which will move the actuator knob 224 distally as it is threaded downwardly along the post 200 of the housing 188. The collar 218 is connected to the actuator 224 and it will move distally together with the actuator 224. Because the collar 218 is sized and configured with a larger diameter than the anterior rod 182 and a larger outer diameter than the diameter on the central opening of the anterior gear 214, the collar 218 will contact the floating anterior gear 214 which is spring biased by the spring 216 in a proximal direction and with distal translation of the actuator 224, the collar 218 will push the anterior gear 214 distally inside the anterior gear chamber 202 compressing the spring 216 and the teeth of the anterior gear 214 will engage the teeth of the posterior gear 194. When the actuator 224 is completely threaded in a distal direction until abutment with the upper housing 198 is made, the anterior gear 214 will be fully engaged with the posterior gear 194. The lock 220 prevents the anterior rod 182 from moving distally with respect to the driver housing 188. With the locking rod 228 engaged with lock bit 179 of the handle 174, the distal tips 192 of the anterior rod 182 and posterior rod 184 will be in position within the drive bores 124 of the drive screws 20, 22, respectively. The user then rotates the handle 164 which may include an attached torque limiting handle 164 as shown in FIG. 20. Rotation of the handle 164 in a clockwise direction rotates the anterior rod 182 clockwise which in turn rotates the anterior drive screw 20 with which it is engaged in a clockwise direction and will result in the anterior actuator 16 threading proximally into the anterior drive screw 20 because of the right-handed thread on the anterior drive screw 20 that is complementary with the right-handed thread inside the bore 88 of the anterior actuator 16. Thus, rotation of the anterior rod 182 in a clockwise direction will move the anterior actuator 16 in a proximal direction relative to the housing 12 because the anterior drive screw 20 is fixed with respect to the housing 12 and the anterior actuator 16 is free to translate along the longitudinal axis of the spacer 10, 100. With proximal movement of the anterior actuator 16, the upper and lower anterior expanders 21a, 21c, will move outwardly into simultaneous upper and lower expansion on the anterior side as the ramped projections 76 on the upper and lower expanders 21a, 21c slide along the ramped grooves 96b, 96a, respectively, on the anterior actuator 16 moving the respective endplates 14b, 14a along with them. With clockwise rotation of the anterior rod 182, the anterior gear 214 will rotate the posterior gear 194 in a counter-clockwise direction. Because the posterior gear 194 is fixed to the posterior rod 184, the posterior rod 184 will rotate in a counter-clockwise direction turning the posterior drive screw 22 in a counter-clockwise direction. Because the posterior drive screw 22 has a left-handed threaded shank 120 and because the posterior actuator bore 88 has a complementary left-handed thread, the posterior actuator 18 will move proximally relative to the posterior drive screw 22 into the posterior actuator bore 88. Because the posterior drive screw 22 is fixed with respect to the housing 12, rotation of the posterior rod 184 in a counter-clockwise direction will move the posterior actuator 18 in a proximal direction relative to the housing 12. With proximal movement of the posterior actuator 18 relative to the posterior drive screw 22, the upper and lower posterior expanders 21b, 21d, will move outwardly into simultaneous upper and lower expansion on the posterior side as the ramped projections 76 on the upper and lower expanders 21b, 21d slide along the ramped grooves 96b, 96a, respectively, on the posterior actuator 18 moving the respective endplates 14b, 14a along with them into a parallel expanded state. Hence, clockwise rotation of the anterior rod 182 translates into counter-clockwise rotation of the posterior rod 184 and because of their respective right-handed and left-handed threads at the drive screw/actuator interface, both the anterior and posterior sides of the spacer 10, 100 will move into uniform activation achieving an expanded state as shown in FIGS. 23B, 24B, 25B and 26B. Of course, rotation of the handle 164 and, hence, rotation of the anterior rod 182 in a counter-clockwise direction will result in collapsing the expanded state and as the actuators 16, 18 and expanders 21 move in opposite directions. Custom expansion is possible by rotating the anterior rod 182 in a clockwise or counter-clockwise direction incrementally as need to achieve a custom height of the spacer 10, 100.

To effect a condition of angular expansion of the spacer 10, 100, which is shown in FIGS. 23C, 24C, 25C and 26C, the user will rotate the actuator 224 on the driver 162 in a counter-clockwise direction from its distal position for parallel expansion as shown in FIG. 22C which will move the actuator 224 proximally as it is threaded upwardly along the post 200 of the housing 188 into a proximal position as shown in FIG. 22B. Because the anterior gear 214 is floating that is movable with respect to the anterior rod 182 along the longitudinal axis and biased towards the proximal position by the spring 216, the anterior gear 214 will be pushed by the spring 216 in the proximal direction as the actuator 224 is moved proximally into a position for angular expansion. When in the actuator 224 is in the proximal position as shown in FIG. 22B, the anterior gear 214 will be disengaged from the posterior gear 194 and, therefore, rotation of the anterior rod 102 will not translate rotation via the anterior and posterior gears 194, 214 to the posterior rod 184. Hence, rotation of the handle 164 will result in rotation of the anterior rod 182 only. Rotation of the handle 164 in a clockwise direction rotates the anterior rod 182 clockwise which in turn rotates the anterior drive screw 20 with which it is engaged in a clockwise direction and will result in the anterior drive screw 20 threading distally into and relative to the anterior actuator 16 because of the right-handed thread on the anterior drive screw 22 that is complementary with the right-handed thread inside the bore 88 of the anterior actuator 16. Thus, rotation of the anterior rod 182 in a clockwise direction will move the anterior actuator 16 in a proximal direction relative to the housing 12 because the anterior drive screw 20 is fixed with respect to the housing 12. With proximal movement of the anterior actuator 16, the upper and lower anterior expanders 21a, 21c, will ramp outwardly into simultaneous upper and lower expansion on the anterior side as the ramped projections 76 on the upper and lower expanders 21a, 21c slide along the ramped grooves 96b, 96a, respectively, on the anterior actuator 16 gradually moving their respective endplates 14b, 14a along with them into an angularly expanded condition. With clockwise rotation of the anterior rod 182, the anterior gear 214 will not rotate the posterior gear 194 in a counter-clockwise direction because the gears 214, 194 are disengaged from each other in the anterior-only expansion mode. Of course, rotation of the handle 164 and, hence, rotation of the anterior rod 182 in a counter-clockwise direction will result in collapsing the anterior side of the spacer 10, 100 from an angular expanded state as the actuators 16, 18 and expanders 21 move in opposite directions. Custom expansion is possible by rotating the anterior rod 182 in a clockwise or counter-clockwise direction as needed to achieve a custom angulation as only the anterior height of the spacer 10, 100 is adjusted with the incremental rotation.

After the spacer 10, 100 is expanded as desired, the instrument 23 is removed. The thumb slider 178 is pulled to disengage the bit 179 from the neck portion 230 of the locking rod 228 of the driver 162 freeing the driver 162 which can then be withdrawn in the proximal direction from the inserter 160. Next, the rod 172 is inserted into the proximal central guide bore 190 on the inserter 160 and threadingly engaged with the distal guide member 167 and rotated to disengage the engagement screw 170 from the spacer 10, 100. The rod 172 may be withdrawn and with the inserter 160 disconnected from the spacer 10, 100, the inserter 160 may be withdrawn. This completes the implantation of the non-SA spacer 10. For the SA spacer 100, bone screws 104 are delivered into the bone screw sockets 108 of the upper and lower endplates 14a, 14b and driven into the upper and lower adjacent vertebral bodies of the spine using a bone screw driver (not shown). After the bone screws 104 are implanted, a lock driver (not shown) is inserted into the instrument socket 152 of the bone screw lock 106 and the bone screw lock 106 is rotated such that the blocking flange 114 covers the bone screw socket 108 to block proximal movement of the bone screws 104 preventing them from backing out with respect to the endplates 14a, 14b.

Turning now to FIGS. 27-34, there is shown another variation of an instrument driver 262 according to the present invention. The driver 262 will be described using like reference numbers for like parts. The driver 262 includes an anterior rod 182 and a posterior rod 184 interconnected via gears at a housing 188 such that rotation of the anterior rod 182 at the handle 164 translates rotational motion to the posterior rod 184 when the actuator 224 is selected for parallel expansion of the spacer 10, 100. When the actuator 224 is selected for angulation of the spacer 10, 100, rotation of the anterior rod 182 at the handle 164 only rotates the anterior rod 182 and does not rotate the posterior rod 184, thereby, only changing the height of the spacer 10, 100 along one side, the anterior side, of the spacer 10, 100. To assist the user in ascertaining the degree and condition of expansion or angulation of the spacer 10, 100 at the distal end which is obscured by anatomy in-situ, the instrument driver 262 is provided with a gauge 300. The gauge 300 mimics the spacer 10, 100 at the distal end and includes indicia to provide a user quantitative and qualitative information whether the spacer 10, 100 is in parallel expansion or angulation and to what degree.

Figure 28:
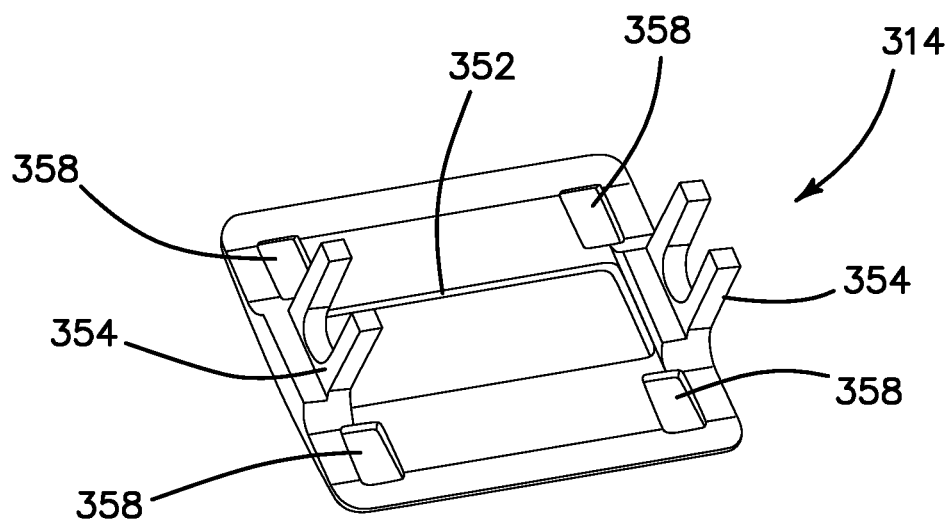
FIG. 28 is a bottom perspective view of a gauge endplate according to the present invention.
Figure 29:
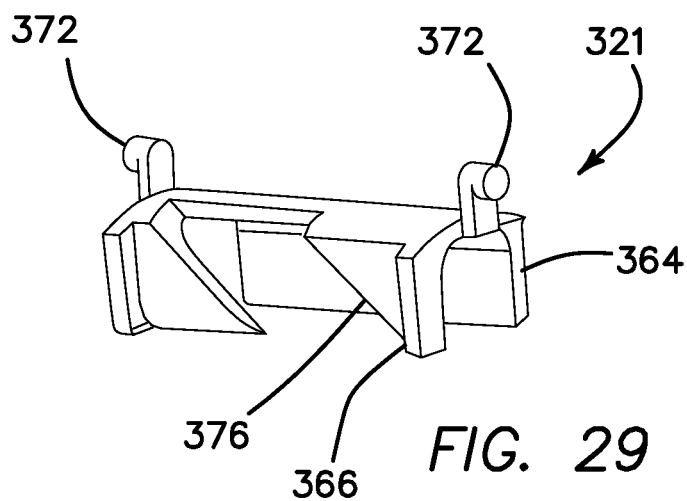
FIG. 29 is a top perspective view of a gauge expander according to the present invention.
Figure 30:
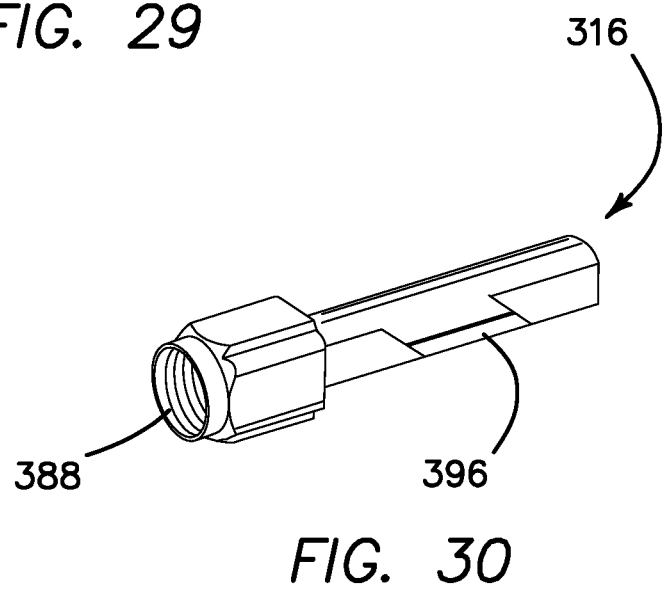
FIG. 30 is a top perspective view of a gauge actuator according to the present invention.

The gauge 300 is constructed similarly to the spacer 10, 100 of the present invention and is located distal to the driver housing 188. The gauge 300 includes upper and lower endplates 314 as shown in FIG. 28. The endplate 314 includes a central opening 352 that is sized and configured to receive a gauge indicia 310 of FIG. 31. The endplate 314 further includes small apertures 358 sized and configured to receive the prongs 372 of the expanders 321 of FIG. 29 in order to connect the endplates 314 to the expanders 321. The endplate 314 includes proximal and distal saddles 354 for mounting on the post 328 of a gauge housing 312.

The expanders 321 include a first rail 364 parallel to a second rail 366. The second rail 366 includes at least one ramp 376. The first and second rails 364, 366 of the upper expander 321 are configured to interdigitate with the first and second rails 364, 366 of an inverted lower expander 321 along the anterior side to achieve a low-profile when in an unexpanded configuration. The same is true for the expanders 321 along the posterior side. The at least one ramp 376 of a lower expander 321 is sized and configured to engage a ramp portion 396 on the anterior side of the actuator 316 and the at least one ramp 376 of an upper expander 321 is sized and configured to engage a ramp portion 396 on the posterior side of the actuator 316. The same is true for expanders 321 and actuators 316 along the anterior side and posterior side of the gauge 300.

The posterior and anterior actuator 316 include a central bore 388 extending between an opening at the proximal and an opening at the distal end. The central bore 388 is sized and configured to receive and allow passage of the anterior rod 182 and posterior rod 184. The proximal end of the central bore 388 is threaded to engage with a threaded portion 350 on the anterior rod 182 and posterior rod 184. An exemplary threaded portion 250 on the anterior rod 182 is shown in FIG. 33. The posterior rod 184 similarly includes a threaded portion 350 configured to threadingly engage with the threaded bore 388 of the posterior actuator 316. The anterior and posterior actuator 316 is configured to encompass and translate with respect to the anterior rod 182 and posterior rod 184, respectively.

Figure 31:
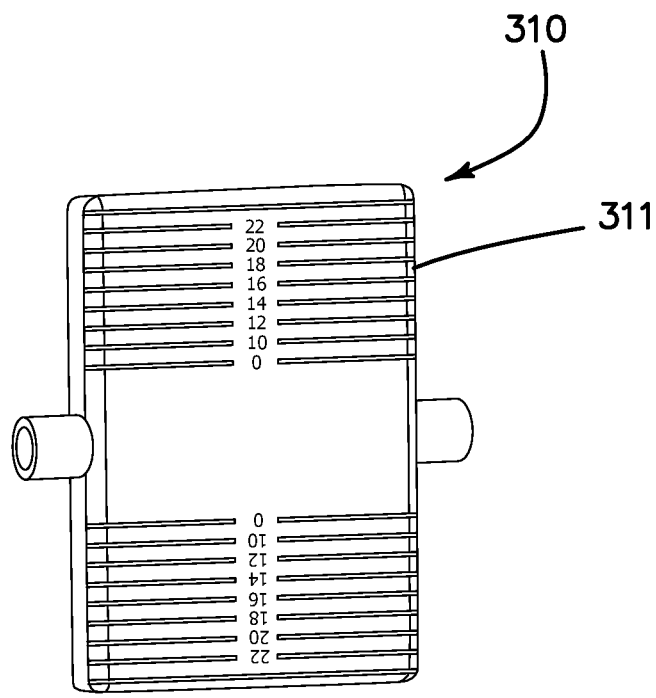
FIG. 31 is a top perspective view of a gauge dial according to the present invention.
Figure 32:
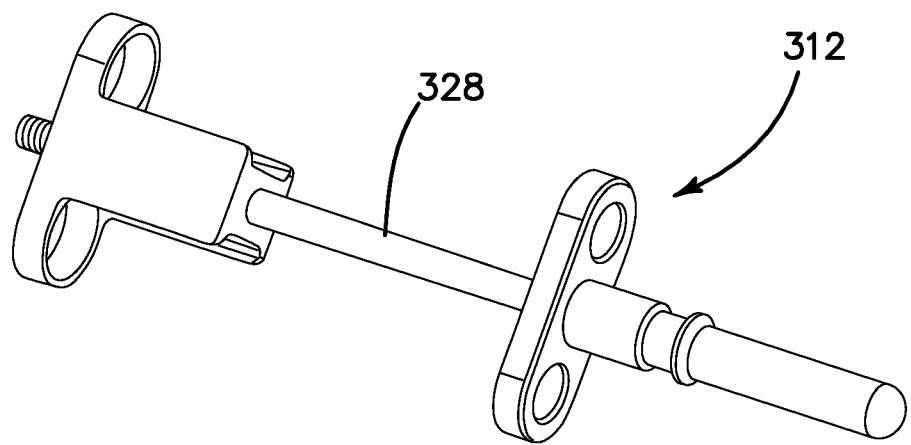
FIG. 32 is a top perspective view of a gauge housing according to the present invention.

The gauge indicia 310 is shown in FIG. 31. The gauge indicia 310 is rectangular in shape and includes a bore for mounting the gauge indicia 310 on the post 328 of the housing 312 shown in FIG. 32. The gauge 310 includes graduated indicia or gauge lines 311 on both the anterior and posterior faces of the gauge 310 that are divided into groups of indicia or gauge lines 311 on the upper and lower sides. The gauge face includes numbers indicating the distance or height of the spacer 10, 100 endplates 14.

The gauge 300 is assembled by sliding the rectangular gauge 310 onto the central post 328 of the gauge housing 312. The anterior actuator 316 is located between two inverted expanders 321 and a posterior actuator 316 between two inverted expanders 321. The rectangular gauge indicia 310 is passed through the endplate openings 352 of the upper and lower endplates 314. The anterior actuator 316 and associated expanders 321 are connected to the upper and lower endplates 14 along the anterior side by passing the projections 372 into respective apertures 358 in the endplates 14. The anterior rod 182 is passed through proximal apertures on the housing 312 and into the bore 388 of the anterior actuator 316 and the threaded portion 350 on the anterior rod 182 is threaded into the proximal end of the bore 388 and the anterior rod 182 is passed through distal apertures of the housing 312. The posterior rod 184 is passed through proximal apertures on the housing 312 and into the bore 388 of the posterior actuator 316 and the threaded portion 350 on the posterior rod 184 is threaded into the proximal end of the bore 388 and the posterior rod 184 is further passed through distal apertures of the housing 312 to connect the gauge 300 to the driver 262. The anterior and posterior actuators 316 are permitted to move threadingly along the anterior and posterior rods 182, 184, respectively.

In use, the instrument 23 is used as described above. When the actuator knob 224 is selected for parallel expansion the anterior rod 182 and posterior rod 184 will be rotating in directions opposite from each other; however, because of the opposite direction threadings on the posterior actuator 316, both the anterior rod 182 and posterior rod 184 will move the anterior and posterior actuators 316, respectively, in the same direction along the longitudinal axis of the gauge 300 and ramp against the expanders moving them along an axis transverse to the longitudinal axis to increase or decrease the distance between the gauge endplates 314 uniformly along the anterior and posterior sides of the gauge 300. This expansion of the gauge 300 is visible to the user who can ascertain and confirm the type of expansion, parallel or angular, as well as the degree of expansion by reading the gauge lines 311 on the gauge faces at the location of the endplates 314. The endplates 314 will point to the gauge lines 311 corresponding to the spacer expansion. When the actuator knob 224 is selected for angular expansion the anterior rod will only be rotating and hence, only the anterior actuator 316 will be threadingly moved with respect to the anterior rod 182 to ramp against the expanders 321 along the anterior side of the gauge 300 moving them along an axis transverse to the longitudinal axis to increase or decrease the distance between the gauge endplates 314 only along the anterior and posterior sides of the gauge 300 to angulate the gauge 300. This expansion of the gauge 300 is visible to the user who can ascertain and confirm the type of expansion, parallel or angular, as well as the degree of angulation by reading the gauge lines 311 on the gauge faces at the endplates 314. The position of the endplates 314 is read by the user against the gauge indicia 311. Thereby, the gauge 300 mimics the action of the spacer 10, 100 that is connected at the distal end to advantageously give the user a visual and quantified information as to the status of the spacer 10, 100.

It is understood that various modifications may be made to the embodiments of the expandable interbody spacer disclosed herein. Therefore, the above description should not be construed as limiting, but merely as exemplifications of preferred embodiments. Those skilled in the art will envision other modifications within the scope and spirit of the present disclosure.

We claim:

1. An expandable interbody spacer having a longitudinal axis, a proximal end and a distal end, and an anterior side and a posterior side, comprising:
    a housing;
    an upper endplate having an upper contact surface;
    a lower endplate having a lower contact surface;
    an upper anterior expander connected to the upper endplate; the upper anterior expander having at least one lower ramp;
    a lower anterior expander connected to the lower endplate; the lower anterior expander having at least one upper ramp;
    an upper posterior expander connected to the upper endplate; the upper posterior expander having at least one lower ramp;
    a lower posterior expander connected to the lower endplate; the lower posterior expander having at least one upper ramp;
    an anterior actuator including at least one upper ramp portion for engaging the at least one lower ramp of the upper anterior expander and at least one lower ramp portion for engaging the at least one upper ramp of the lower anterior expander; the anterior actuator having a threaded bore;
    a posterior actuator including at least one upper ramp portion for engaging the at least one lower ramp of the upper posterior expander and at least one lower ramp portion for engaging the at least one upper ramp of the lower posterior expander; the posterior actuator having a threaded bore;
    an anterior drive screw threadably engaged with the threaded bore of the anterior actuator; the anterior drive screw laterally and longitudinally fixed and rotatable with respect to the housing; whereby rotation of the anterior drive screw causes the anterior actuator to move along the longitudinal axis and the at least one lower ramp of the upper anterior expander slideable against the at least one upper ramp portion of the anterior actuator to cause the upper anterior expander and connected upper endplate to move along an axis transverse to the longitudinal axis and the at least one upper ramp of the lower anterior expander slideable against the at least one lower ramp portion of the anterior actuator to cause the lower anterior expander and connected lower endplate to move along an axis transverse to the longitudinal axis; and
    a posterior drive screw threadably engaged with the threaded bore of the posterior actuator; the posterior drive screw laterally and longitudinally fixed and rotatable with respect to the housing; whereby rotation of the posterior drive screw causes the posterior actuator to move along the longitudinal axis and the at least one lower ramp of the upper posterior expander slideable against the at least one upper ramp portion of the posterior actuator to cause the upper posterior expander and connected upper endplate to move along an axis transverse to the longitudinal axis and the at least one upper ramp of the lower posterior expander slideable against the at least one lower ramp portion of the posterior actuator to cause the lower anterior expander and connected lower endplate to move along an axis transverse to the longitudinal axis.

2. The expandable interbody spacer of claim 1 wherein rotation of the anterior drive screw in a first direction causes the anterior actuator to move along the longitudinal axis in a first direction to increase the separation between the upper endplate and the lower endplate along the anterior side; and wherein rotation of the posterior drive screw in a second direction opposite to the first direction causes the posterior actuator to move along the longitudinal axis in the first direction to increase the separation between the upper endplate and the lower endplate along the posterior side.

3. The expandable interbody spacer of claim 1 wherein the anterior drive screw and the threaded bore of the anterior actuator have right-handed threads and the posterior drive screw and the threaded bore of the posterior actuator have left-handed threads.

4. The expandable interbody spacer of claim 1 wherein rotation of the anterior drive screw in a first direction increases the separation between the upper endplate and the lower endplate from an unexpanded configuration to an expanded configuration along the anterior side and rotation of the anterior drive screw in a second direction decreases the separation between the upper endplate and the lower endplate from an expanded configuration to an unexpanded configuration along the anterior side.

5. The expandable interbody spacer of claim 1 wherein rotation of the posterior drive screw in a first direction increases the separation between the upper endplate and the lower endplate from an unexpanded configuration to an expanded configuration along the posterior side and rotation of the posterior drive screw in a second direction decreases the separation between the upper endplate and the lower endplate from an expanded configuration to an unexpanded configuration along the posterior side.

6. The expandable interbody spacer of claim 1 further including an anchor socket and a lock socket integrally formed with the upper endplate and the lower endplate; the anchor socket being configured to receive a bone anchor; and a lock rotatably received in the lock socket and configured to cover the anchor socket.

7. An instrument for an expandable interbody spacer having an anterior side and a posterior side comprising:
a housing having an anterior gear chamber interconnected to a posterior gear chamber;
an anterior rod extending from a proximal end to a distal end and rotatably connected to the housing; the anterior rod having a spacer-engaging tip at the distal end and a handle at the proximal end;
a posterior rod extending from a proximal end to a distal end and spaced apart from the anterior rod; the posterior rod being rotatably connected to the housing; the posterior rod having a spacer-engaging tip at the distal end aligned with the spacer-engaging tip of the anterior rod;
a posterior gear fixed to the proximal end of the posterior rod and located inside the posterior gear chamber;
an anterior gear connected concentrically to the anterior rod; the anterior gear located inside the anterior gear chamber and movable longitudinally with respect to the anterior rod; and
an actuator configured to move the anterior gear along the anterior rod between a disengaged position in which the anterior gear is disengaged from the posterior gear and an engaged position in which the anterior gear is engaged with the posterior gear;
wherein the actuator is threaded to the housing and connected to a collar configured to engage the anterior gear; and
wherein rotation of the handle causes rotation of both the anterior rod and the posterior rod when in the engaged position.

8. The instrument of claim 7 wherein when in the disengaged position rotation of the handle causes rotation only of the anterior rod.

9. The instrument of claim 7 wherein when in the engaged position rotation of the handle in a first direction causes rotation of the anterior rod in a first direction and rotation of the posterior rod in a second direction opposite to the first direction.

10. The instrument of claim 7 further including a spring located inside a spring chamber formed in the housing; the spring being concentric with the anterior rod and configured to bias the anterior gear proximally.

11. The instrument of claim 7 wherein the anterior rod and the posterior rod are laterally and longitudinally fixed to the housing.

12. The instrument of claim 7 further including an inserter having a proximal end and a distal end; the anterior rod and the posterior rod insertable into the inserter at the proximal end; the inserter configured to connect to the housing.

13. The instrument of claim 7 wherein rotation of the anterior rod rotates the anterior gear.

14. An expandable spacer and instrument system; comprising:
an expandable spacer having an anterior side and a posterior side along a longitudinal axis; an upper endplate and a lower endplate on either side of a housing; an anterior drive screw longitudinally fixed to the housing and threadingly connected to an anterior actuator located along the anterior side such that rotation of the anterior drive screw moves the anterior actuator along the longitudinal axis which moves the upper endplate and the lower endplate along an axis transverse to the longitudinal axis to increase or decrease a height of the expandable spacer along the anterior side; and a posterior drive screw longitudinally fixed to the housing and threadingly connected to a posterior actuator along the posterior side such that rotation of the posterior drive screw moves the posterior actuator along the longitudinal axis which moves the upper endplate and the lower endplate along an axis transverse to the longitudinal axis to increase or decrease a height of the expandable spacer along the posterior side;
an instrument including an anterior rod connected to an instrument housing, the anterior rod having a handle at a proximal end and a tip at a distal end for engaging the anterior drive screw, wherein rotation of the anterior rod in a first direction rotates the anterior drive screw in the first direction; an anterior gear connected to and rotatable with the anterior rod; a posterior rod connected to the instrument housing; a posterior gear connected to the posterior rod; the anterior gear movable to engage or disengage the posterior gear;

wherein, when the anterior gear is engaged with the posterior gear, rotation of the anterior rod in a first direction rotates the anterior gear in the first direction and the posterior gear and the posterior rod in a second direction opposite to the first direction to increase the distance between the upper and lower endplates along both the anterior and posterior sides; and wherein, when the anterior gear is not engaged with the posterior gear, rotation of the anterior rod in the first direction rotates the anterior gear in the first direction to increase the distance between the upper and lower endplates along only the anterior side to angulate the upper and lower endplates.

15. The system of claim 14 wherein, when the anterior gear is not engaged with the posterior gear, the posterior rod does not rotate with rotation of the posterior rod.

16. The system of claim 15 wherein the gauge includes an anterior side and a posterior side along a longitudinal axis; an upper gauge endplate and a lower gauge endplate; an anterior gauge actuator connected to upper and lower anterior gauge expanders that are connected to the upper and lower gauge endplates along the anterior side; the anterior gauge actuator having a central bore extending between a proximal bore opening and a distal bore opening sized and configured to receive the anterior rod; a posterior gauge actuator connected to upper and lower posterior gauge expanders that are connected to the upper and lower gauge endplates along the posterior side; the posterior gauge actuator having a central bore extending between a proximal bore opening and a distal bore opening sized and configured to receive the posterior rod; the anterior rod having a threaded portion configured to threadingly engage a thread inside the central bore of the anterior gauge actuator; the posterior rod having a threaded portion configured to threadingly engage a thread inside the central bore of the posterior gauge actuator; wherein rotation of the anterior rod moves the anterior gauge actuator along the longitudinal axis with respect to the anterior rod and moves the upper and lower gauge endplates along an axis transverse to the longitudinal axis to increase or decrease a height of the gauge along the anterior side; and wherein rotation of the posterior rod moves the posterior gauge actuator along the longitudinal axis with respect to the posterior rod and moves the upper and lower gauge endplates along an axis transverse to the longitudinal axis to increase or decrease a height of the gauge along the posterior side.

17. The system of claim 16 wherein the upper and lower gauge endplates include openings and the gauge includes a face with graduated markings located within the openings of the upper and lower gauge endplates.

18. The system of claim 14 wherein the instrument further includes a gauge configured to mimic the configuration of the expandable spacer.

19. The system of claim 14 wherein the instrument further includes an inserter including a proximal end and a distal end, the inserter configured to receive the anterior and posterior rods at the proximal end thereof and to connect to the expandable spacer at the distal end thereof.

* * * * *